(12) United States Patent
Brockunier et al.

(10) Patent No.: US 8,741,910 B2
(45) Date of Patent: Jun. 3, 2014

(54) SOLUBLE GUANYLATE CYCLASE ACTIVATORS

(75) Inventors: Linda L. Brockunier, Orange, NJ (US); Jian Guo, Scotch Plains, NJ (US); Emma R. Parmee, Scotch Plains, NJ (US); Subharekha Raghavan, Teaneck, NJ (US); Keith Rosauer, Laurence Harbor, NJ (US); Darby Schmidt, Arlington, MA (US); John E. Stelmach, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 308 days.

(21) Appl. No.: 13/127,334

(22) PCT Filed: Nov. 16, 2009

(86) PCT No.: PCT/US2009/064570
§ 371 (c)(1),
(2), (4) Date: May 3, 2011

(87) PCT Pub. No.: WO2010/065275
PCT Pub. Date: Jun. 10, 2010

(65) Prior Publication Data
US 2011/0218202 A1    Sep. 8, 2011

Related U.S. Application Data

(60) Provisional application No. 61/200,221, filed on Nov. 25, 2008.

(51) Int. Cl.
*A61K 31/519* (2006.01)
*C07D 471/04* (2006.01)
*C07D 487/04* (2006.01)
*A61P 9/12* (2006.01)
*A61P 9/04* (2006.01)

(52) U.S. Cl.
USPC ............ 514/264.11; 514/265.1; 544/279; 544/280

(58) Field of Classification Search
USPC ............ 544/279, 280; 514/264.11, 265.1
See application file for complete search history.

(56) References Cited

U.S. PATENT DOCUMENTS

| | | | |
|---|---|---|---|
| 5,665,732 | A | 9/1997 | Baker et al. |
| 6,162,819 | A | 12/2000 | Schindler et al. |
| 6,166,027 | A | 12/2000 | Straub et al. |
| 6,613,772 | B1 | 9/2003 | Schindler et al. |
| 6,693,102 | B2 | 2/2004 | Stasch et al. |
| 6,743,798 | B1 | 6/2004 | Straub et al. |
| 6,844,347 | B1 | 1/2005 | Schindler et al. |
| 6,958,344 | B2 | 10/2005 | Bonnert et al. |
| 7,045,526 | B2 | 5/2006 | Schindler et al. |
| 7,115,599 | B2 | 10/2006 | Stasch et al. |
| 7,138,402 | B2 | 11/2006 | Kasibhatla et al. |
| 7,173,037 | B2 | 2/2007 | Alonso-Alija et al. |
| 7,666,867 | B2 | 2/2010 | Makriyannis et al. |
| 7,674,825 | B2 | 3/2010 | Alonso-Alija et al. |
| 7,985,876 | B2 | 7/2011 | Hahn et al. |
| 8,114,400 | B2 | 2/2012 | Schirok et al. |
| 8,183,271 | B2 | 5/2012 | Bartel et al. |
| 8,217,063 | B2 | 7/2012 | Hahn et al. |
| 8,222,262 | B2 | 7/2012 | Eriksen et al. |
| 8,309,551 | B2 | 11/2012 | Schirok et al. |
| 2004/0048866 | A1 | 3/2004 | Kolasa et al. |
| 2004/0053915 | A1 | 3/2004 | Geiss et al. |
| 2005/0222170 | A1 | 10/2005 | Weigand et al. |
| 2006/0014915 | A1 | 1/2006 | Ahn et al. |
| 2006/0052397 | A1 | 3/2006 | Alonso-Alija et al. |
| 2006/0106041 | A1 | 5/2006 | Kuo et al. |

(Continued)

FOREIGN PATENT DOCUMENTS

| | | |
|---|---|---|
| DE | 19744027 A1 | 4/1999 |
| EP | 0908456 A1 | 4/1999 |

(Continued)

OTHER PUBLICATIONS

Boerrigter et al., Handbook of Experimental Pharmacology, (2009), vol. 191, "Modulation of cGMP in Heart Failure: A New Therapeutic Paradigm", pp. 485-506.

(Continued)

*Primary Examiner* — Susanna Moore
(74) *Attorney, Agent, or Firm* — Kenrick L. Vidale; Carol S. Quagliato

(57) ABSTRACT

Compounds of Formula I are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of the Formula I, to their use for the therapy and prophylaxis of the abovementioned diseases and for preparing pharmaceuticals for this purpose, and to pharmaceutical preparations which comprise compounds of the Formula I.

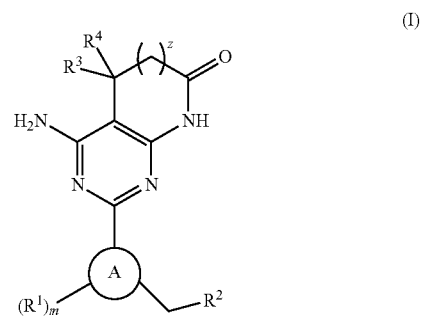

20 Claims, No Drawings

(56) References Cited

U.S. PATENT DOCUMENTS

| | | |
|---|---|---|
| 2008/0027092 A1 | 1/2008 | Bonnert et al. |
| 2008/0188666 A1 | 8/2008 | Berger et al. |
| 2012/0029002 A1 | 2/2012 | Straub et al. |

FOREIGN PATENT DOCUMENTS

| | | |
|---|---|---|
| EP | 1339717 B1 | 9/2001 |
| EP | 1390365 B1 | 4/2002 |
| EP | 1509228 B1 | 5/2003 |
| WO | 01/83490 A1 | 11/2001 |
| WO | 02/42299 A1 | 5/2002 |
| WO | 02/42300 A1 | 5/2002 |
| WO | 02/059083 A2 | 8/2002 |
| WO | 03/095451 A1 | 11/2003 |
| WO | WO2005046725 A1 | 5/2005 |
| WO | WO2007009607 A1 | 1/2007 |
| WO | WO2007003435 A2 | 1/2007 |
| WO | WO2007124854 A1 | 8/2007 |
| WO | WO2008031513 A1 | 3/2008 |
| WO | WO2008061657 A1 | 5/2008 |
| WO | 2011/019581 A1 | 2/2011 |
| WO | 2011/149921 A1 | 12/2011 |

OTHER PUBLICATIONS

Ghofrani et al., Eur. Respiratory Rev. (2009), vol. 18, "Soluble guanylate cyclase stimulation: an emerging option in pulmonary hypertension therapy" pp. 35-41.

Frey et al., BMC Pharmacology, (2007) "BAY 58-2667, a soluble guanylate cyclase activator, has a favourable safety profile and reduces peripheral vascular resistance in healthy male volunteers" pp. 1-2.

Bayer AG Investor Conference Call (edited transcript), (2012) pp. 1-19.

International Search Report of PCT/US2009/064570 dated Jan. 27, 2010.

Supplementary European Search Report of EP 09830834 dated Feb. 8, 2013.

International Preliminary Report on Patentability PCT/US2009/064570 dated May 31, 2011.

English translation of DE19,744,027 abstract, Aug. 4, 1999.

Hering, K.W., et. al., "The design and synthesis of YC-1 analogues as probes for soluble guanylate cyclase"; Bioorg. Med. Chem. Lett, 2006, vol. 16, pp. 618-621.

Hoenicka, M.J., "Purified soluble guanylyl cyclase expressed in baculovirus/sf9 system: stimulation by YC-1, nitric oxide and carbon monoxide"; J. Mol. Med., 1999, vol. 77, pp. 14-23.

Mulsch, a., et. al., "Effect of YC-1, an NO-independent, super-oxide sensitive stimulator of soluble guanylyl cyclase, on smooth muscle responsiveness to nitrovasodilators", British Journal of Pharmacology, 1997, vol. 120, pp. 681-689.

Stasch, et. al., "Pharmacological actions of a novel NO-independent guanylyl cyclase stimulator, BAY 41/8543: in vitro studies", British Journal of Pharmacology, vol. 135, 2002, pp. 333-343.

Stasch, J. P., et. al., "NO-independent regulatory site on soluble guanylate cyclase"; Nature, vol. 410, 2001, pp. 212-215.

Stasch, J.P., et. al., "Cardiovascular actions of a novel No-independent guanylyl cyclase stimulator, BAY 41/8543: in vivo studies", British Journal of Pharmacology, vol. 135, 2002, pp. 344-355.

Straub, A., et. al., "Metabolites of Orally Active No-independent Pyrazolopyridine Stimulators of Soluble Guanylate Cyclase", Bioorg. Med. Chem., vol. 10, 2002, pp. 1711-1717.

Straub, A., et. al., "NO Independent stimulators of Soluble Guanylate Cyclase"; Bioorg. Med.Chem.Lett, vol. 11, 2001, pp. 781-784.

SOLUBLE GUANYLATE CYCLASE ACTIVATORS

CROSS REFERENCE TO RELATED APPLICATIONS

This application is a 35 U.S.C. §371 filing from International Application No. PCT/US2009/064570, filed Nov. 16, 2009, which claims priority to U.S. Provisional Application No. 61/200,221, filed Nov. 25, 2008.

Cyclic GMP is an important intracellular messenger which triggers a multitude of different effects via the modulation of cGMP-dependent protein kinases, phosphodiesterases and ion channels. Examples are the relaxation of smooth muscles, the inhibition of thrombocyte activation and the inhibition of the proliferation of smooth-muscle cells and of leukocyte adhesion. cGMP is produced by particulate and soluble guanylate cyclases as a response to a number of extracellular and intracellular stimuli. In the case of the particulate guanylate cyclases, stimulation is essentially effected by peptidic messengers, such as the atrial natriuretic peptide or the cerebral natriuretic peptide. The soluble guanylate cyclases ("sGC"), which are cytosolic heterodimeric heme proteins, in contrast, are essentially regulated by a family of low-molecular-weight factors which are formed enzymatically. The most important stimulant is nitrogen monoxide ("NO") or a closely related species. The function of other factors such as carbon monoxide or the hydroxyl radical is still largely unclear. The binding of NO to the heme with formation of a penta-coordinate heme-nitrosyl complex is proposed as the mechanism of the activation by NO. The associated release of the histidine which is bound in the basal state to the iron converts the enzyme into the active conformation.

Active soluble guanylate cyclases are composed of an α and a β subunit each. Several subunit subtypes have been described which differ from one another with respect to sequence, tissue-specific distribution and expression in different development stages. The subtypes $α_1$ and $β_1$ are mainly expressed in brain and lung, while $β_2$ is found in particular in liver and kidney. The subtype $α_2$ was shown to be present in human fetal brain. The subunits referred to as $α_3$ and $β_3$ were isolated from human brain and are homologous to $α_1$ and $β_1$. More recent works indicate an $α_{2i}$ subunit which contains an insert in the catalytic domain. All subunits show great homologies in the region of the catalytic domain. The enzymes presumably contain one heme per heterodimer, which is bound via $β_1$-Cys-78 and/or $β_1$-His-105 and is part of the regulatory center.

Under pathologic conditions, the formation of guanylate-cyclase-activating factors can be reduced, or their degradation may be promoted owing to the increased occurrence of free radicals. The resulting reduced activation of the sGC leads, via a weakening of the respective cGMP-mediated cellular response, for example to an increase of the blood pressure, to platelet activation or to increased cell proliferation and cell adhesion. As a consequence, formation of endothelial dysfunction, atherosclerosis, hypertension, stable or unstable angina pectoris, thromboses, myocardial infarction, strokes or erectile dysfunction results. Pharmacological stimulation of sGC offers a possibility to normalize cGMP production and therefore makes possible the treatment and/or prevention of such disorders.

For the pharmacological stimulation of the sGC, use has been made of compounds whose activity is based on an intermediate NO release, for example organic nitrates. The drawback of this treatment is the development of tolerance and a reduction of activity, and the higher dosage which is required because of this.

Various sGC stimulators which do not act via NO release were described by Vesely in a series of publications. However, the compounds, most of which are hormones, plant hormones, vitamins or natural compounds such as, for example, lizard poisons predominantly only have weak effects on the cGMP formation in cell lysates. D. L. Vesely, Eur. J. Clin. Invest., vol. 15, 1985, p. 258; D. L. Vesely, Biochem. Biophys. Res. Comm., vol. 88, 1979, p. 1244. A stimulation of heme-free guanylate cyclase by protoporphyrin IX was demonstrated by Ignarro et al., Adv. Pharmacol., vol. 26, 1994, p. 35. Pettibone et al., Eur. J. Pharmacol., vol. 116, 1985 p. 307, described an antihypertensive action of diphenyliodonium hexafluorophosphate and attributed this to a stimulation of sGC. According to Yu et al., Brit. J. Pharmacol, vol. 114, 1995, p. 1587, isoliquiritigenin, which has a relaxing action on isolated rat aortas, also activates sGC. Ko et al., Blood vol. 84, 1994, p. 4226, Yu et al., Biochem. J. vol. 306, 1995, p. 787, and Wu et al., Brit. J. Pharmacol. vol. 116, 1995, p. 1973, demonstrated a sGC-stimulating activity of 1-benzyl-3-(5-hydroxymethyl-2-furyl)indazole and demonstrated an antiproliferative and thrombocyte-inhibiting action. Pyrazoles and fused pyrazoles which exhibit a sGC-stimulating activity are described in European Patent Application No. 908,456 and German Patent Application No. 19,744,027.

A series of 2-sulfonylaminobenzoic acid N-arylamides, the N-aryl group of which carries a thio substituent, have been mentioned in the literature. These compounds in which the N-aryl group generally carries as further substituents groups which are readily oxidizable such as, for example, two hydroxy groups being in para position with respect to one another and which in this case can be regarded as hydroquinone derivatives, are auxiliaries for the preparation of photographic materials (see, for example, Chemical Abstracts 119, 105757; 120, 41858; 123, 70224; or 126, 257007). British patent publication No. 876,526 (Chemical Abstracts 56, 15432e) discloses 3,5-dichloro-2-methylsulfonylaminobenzoic acid N-(5-chloro-2-(4-chlorophenylmercapto)-phenyl)-amide which can be used for the protection of wool against moths.

It has now been found that the compounds of the present invention effect a strong activation of guanylate cyclase and are therefore suitable for the therapy and prophylaxis of disorders which are associated with a low cGMP level.

SUMMARY OF THE INVENTION

The present invention relates to compounds which activate soluble guanylate cyclase which are valuable pharmaceutically active compounds for the therapy and prophylaxis of diseases, for example for cardiovascular diseases such as hypertension, heart failure, pulmonary hypertension, angina pectoris, diabetes, cardiac insufficiency, thromboses or atherosclerosis. The compounds of the Formula I

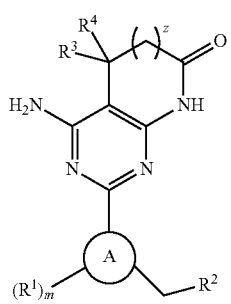

I are capable of modulating the body's production of cyclic guanosine monophosphate ("cGMP") and are generally suitable for the therapy and prophylaxis of diseases which are associated with a disturbed cGMP balance. The invention furthermore relates to processes for preparing compounds of the Formula I, to their use for the therapy and prophylaxis of the above-mentioned diseases and for preparing pharmaceuticals for this purpose, and to pharmaceutical preparations which comprise compounds of Formula I.

DETAILED DESCRIPTION OF THE INVENTION AND PREFERRED EMBODIMENTS

The invention concerns compounds of Formula I which activate soluble guanylate cyclase:

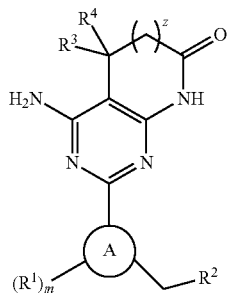

I and pharmaceutically acceptable salts thereof, wherein

is an 8- or 9-membered heteroaryl;
$R^a$ and $R^b$ are independently selected at each occurrence from the group consisting of —H and —$C_1$-$C_6$ alkyl;
$R^c$ is independently selected at each occurrence from the group consisting of —$C_1$-$C_6$ alkyl, —$CF_3$, and aryl;
$R^1$ is independently selected at each occurrence from the group consisting of —H, halo, aryl, heteroaryl, —$C_1$-$C_6$ alkyl, —$C_{3-10}$ cycloalkyl, —OR, —$NO_2$, —CN, —$CO_2R^a$, —$NR^aR^b$, —$S(O)_pR^c$, thioxo, azido, —C(=O)$R^a$, —OC(O)$_nR^a$, —OC(=O)O$R^a$, —OC(=O)N$R^aR^b$, —$SO_2NR^aNR^b$, —$NR^a(C=O)_nR^b$, —$NR^aSO_2R^b$, —$NR^aC(=O)OR^b$, —$NR^aC(O)NR^aR^b$, —$NR^aSO_2NR^aR^b$, —$C_{2-10}$alkenyl, and —$C_{2-10}$alkynyl, said aryl, heteroaryl, alkyl, cycloalkyl, alkenyl and alkynyl optionally being substituted with one to three substituents selected from halo, —$C_1$-$C_6$ alkyl, —OR, oxo, aryl, heteroaryl, —$C_{3-10}$ cycloalkyl, —$NO_2$, —CN, —$CO_2R^a$, $NR^aR^b$, —$S(O)_pR^c$, thioxo, azido, —C(=O)$R^a$, —O(C=O)$_nR^a$, —OC(=O)O$R^a$, —OC(=O)N$R^aR^b$, —$SO_2NR^aNR^b$, —$NR^a(C=O)_nR^b$, —$NR^aSO_2R^b$, —$NR^aC(=O)OR^b$, —$NR^aC(=O)NR^aR^b$, —$NR^aSO_2NR^aR^b$ and —$CF_3$;
$R^2$ is selected from the group consisting of —$C_1$-$C_6$ alkyl, —$(CR^a_2)_rOR$, —$(CR^a_2)_rS(O)_pR^c$, —$(CR^a_2)_rCF_3$, —$(CR^a_2)_r$—$C_{3-10}$cycloalkyl, —$(CR^a_2)_r$aryl, —$(CR^a_2)_r$heteroaryl, —$(CR^a_2)_r$—$C_{2-10}$alkenyl, —$(CR^a_2)_r$—$C_{2-10}$alkyl, and —$(CR^a_2)_rC(O)Oalkyl$, said alkyl, cycloalkyl, aryl, heteroaryl, alkenyl and alkynyl being optionally substituted with one to three substituents selected from halo, —$C_1$-$C_6$ alkyl, —$CF_3$, —CN and —OR;
R is independently selected at each occurrence from the group consisting of —H, —$C_1$-$C_6$ alkyl, —$CF_3$, and aryl;
$R^3$ and $R^4$ are independently selected from the group consisting of —H and —$C_1$-$C_6$ alkyl; when $R^3$ and $R^4$ are $C_1$-$C_6$ alkyl they may optionally be joined to form a cycloalkyl;
m is 0 (zero), 1, 2, or 3;
p is 0 (zero), 1 or 2;
r is 0 (zero), 1, 2, 3, 4, 5, or 6; and
z is 0 (zero) or 1.

In a further embodiment, the invention is directed to compounds of Formula II:

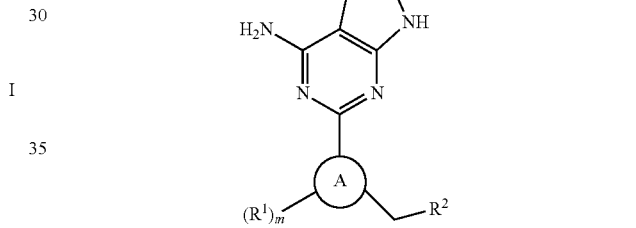

II and pharmaceutically acceptable salts thereof, wherein

is an 8- or 9-membered heteroaryl;
$R^a$ is independently selected at each occurrence from the group consisting of —H and —$C_1$-$C_6$ alkyl;
$R^1$ is independently selected at each occurrence from the group consisting of —H, halo, aryl, heteroaryl, —$C_1$-$C_6$ alkyl and —$C_{3-10}$ cycloalkyl, said aryl, heteroaryl, alkyl and cycloalkyl optionally being substituted with one to three substituents selected from halo, —$C_1$-$C_6$ alkyl, and —$CF_3$;
$R^2$ is selected from the group consisting of —$C_1$-$C_6$ alkyl, —$(CR^a_2)_rCF_3$, —$(CR^a_2)_rC_{3-10}$cycloalkyl, —$(CR^a_2)_r$aryl, —$(CR^a_2)_r$heteroaryl, —$(CR^a_2)_r$alkenyl, —$(CR^a_2)_r$alkynyl, and —$(CR^a_2)_rC(O)Oalkyl$, said alkyl, cycloalkyl, aryl, heteroaryl, alkenyl and alkynyl being optionally substituted with one to three substituents selected from halo, —$C_1$-$C_6$ alkyl, —$CF_3$, —CN, and —OR;
R is independently selected at each occurrence from the group consisting of —H, —$C_1$-$C_6$ alkyl and aryl;
$R^3$ and $R^4$ are independently selected from the group consisting of H and $C_1$-$C_6$ alkyl; when $R^3$ and $R^4$ are $C_1$-$C_6$ alkyl they may optionally be joined to form a cycloalkyl;
m is 0, 1, 2 or 3; and
r is 0, 1, 2, 3, 4, 5, or 6.

In another embodiment,

is

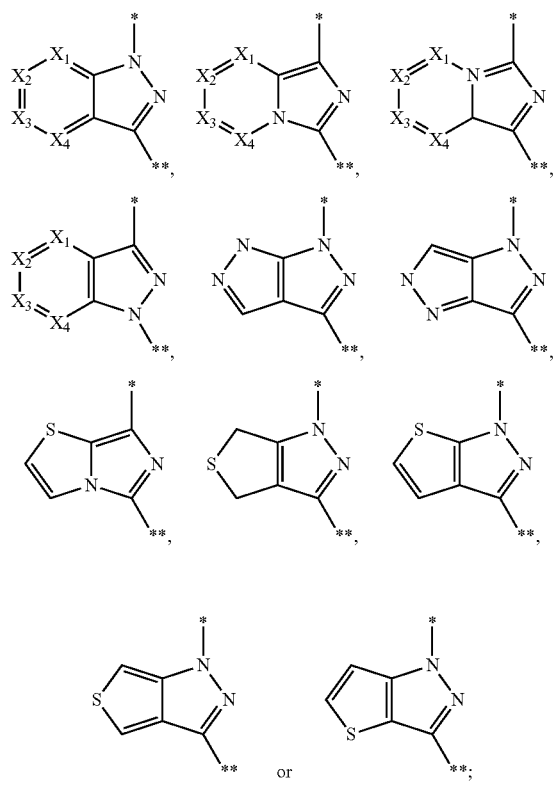

where * indicates attachment to the pyrmidinyl ring and ** indicates attachment to the —CH$_2$—R$^2$ of structural Formula I or II;

X$^1$, X$^2$, X$^3$ and X$^4$ are independently selected from N or CH, provided that no more than one of X$^1$, X$^2$, X$^3$ and X$^4$ is N; and all other variables are as previously defined.

In another embodiment,

is

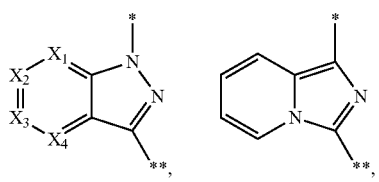

-continued

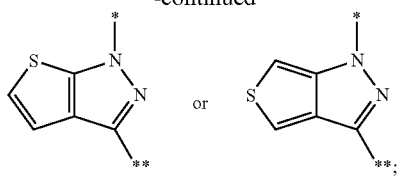

where * indicates attachment to the pyrmidinyl ring and ** indicates attachment to the —CH$_2$—R$^2$ of structural Formula I or II;

X$^1$, X$^2$, X$^3$ and X$^4$ are independently selected from N or CH, provided that no more than one of X$^1$, X$^2$, X$^3$ and X$^4$ is N; and all other variables are as previously defined.

In an embodiment, R$^3$ is —C$_1$-C$_6$ alkyl. In an embodiment, R$^4$ is —C$_1$-C$_6$ alkyl. In a further embodiment, R$^3$ and R$^4$ are methyl.

In a further embodiment, the invention is directed to compounds of Formula II:

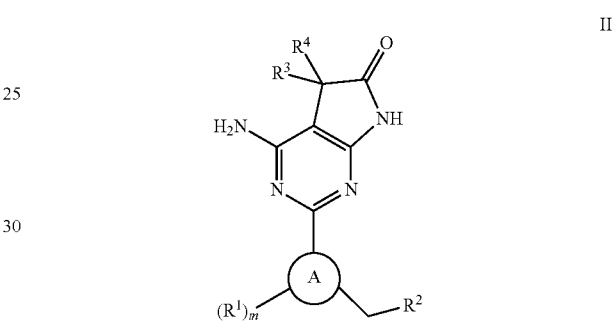

II and pharmaceutically acceptable salts thereof, wherein

is

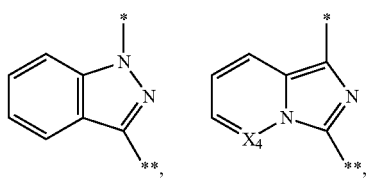

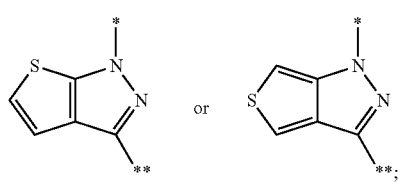

X$^4$ is selected from the group consisting of CH and N;

R$^a$ is independently selected at each occurrence from the group consisting of —H and —C$_1$-C$_6$ alkyl;

R$^1$ is independently selected at each occurrence from the group consisting of —H, halo and —C$_1$-C$_6$ alkyl, said alkyl optionally being substituted with one to three substituents selected from halo, —$C_1$-$C_6$ alkyl, and —$CF_3$;

$R^2$ is selected from the group consisting of —$C_1$-$C_6$ alkyl, —$(CR^a{}_2)_rCF_3$, —$(CR^a{}_2)_rC_{3-10}$cycloalkyl, and —$(CR^a{}_2)_r$aryl, said alkyl, cycloalkyl and aryl being optionally substituted with one to three substituents selected from halo, —$C_1$-$C_6$ alkyl and —$CF_3$;

R is independently selected from —H, —$C_1$-$C_6$ alkyl and aryl;

$R^3$ and $R^4$ are each $C_1$-$C_6$ alkyl;

M is 0, 1, 2 or 3; and r is 0, 1, 2, or 3.

In another embodiment, compounds of the invention are selected from the group consisting of

| Example | IUPAC NAME |
|---|---|
| 1 | 4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one |
| 2 | 4-amino-5,5-dimethyl-2-[3-(3,3,3-trifluoropropyl)-1H-indazol-1-yl]-5,7-dihydro-6H-pyrrolo[2,3-d]pyrimidin-6-one |
| 3 | 4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one |
| 4 | 4-amino-5,5-dimethyl-2-[3-(2,3,6-trifluorobenzyl)-1H-indazol-1-yl]-5,7-dihydro-6H-pyrrolo[2,3-d]pyrimidin-6-one |
| 5 | 4-amino-2-(5-fluoro-3-hexyl-1H-indazol-1-yl)-5,5-dimethyl-5,7-dihydro-6H-pyrrolo[2,3-d]pyrimidin-6-one |
| 6 | 4-amino-2-[5-bromo-3-(2,3,6-trifluorobenzyl)-1H-indazol-1-yl]-5,5-dimethyl-5,7-dihydro-6H-pyrrolo[2,3-d]pyrimidin-6-one |
| 7 | 4-amino-5,5-dimethyl-2-[5-pyridin-4-yl-3-(2,3,6-trifluorobenzyl)-1H-indazol-1-yl]5,7-dihydro-6H-pyrrolo[2,3-d]pyrimidin-6-one |
| 8 | 4-amino-5,5-dimethyl-2-[3-(4,4,4-trifluorobutyl)-1H-thieno[3,4-c]pyrazol-1-yl]-5,7-dihydro-6H-pyrrolo[2,3-d]pyrimidin-6-one |
| 9 | 4-amino-5,5-dimethyl-2-[3-(2,3,6-trifluorobenzyl)-1H-thieno[3,4-c]pyrazol-1-yl]-5,7-dihydro-6H-pyrrolo[2,3-d]pyrimidin-6-one |
| 10 | 4-amino-5,5-dimethyl-2-[3-(2,3,6-trifluorobenzyl)-4,6-dihydro-1H-thieno[3,4-c]pyrazol-1-yl]-5,7-dihydro-6H-pyrrolo[2,3-d]pyrimidin-6-one |
| 11 | 4-amino-2-[3-(2-cyclopentylethyl)-1H-indazol-1-yl]-5,5-dimethyl-5,7-dihydro-6H-pyrrolo[2,3-d]pyrimidin-6-one |
| 12 | 4-amino-2-[3-(2-fluorobenzyl)-1H-indazol-1-yl]-5,5-dimethyl-5,7-dihydro-6H-pyrrolo[2,3-d]pyrimidin-6-one |
| 13 | 4-amino-2-[5-chloro-3-(2-fluorobenzyl)-1H-indazol-1-yl]-5,5-dimethyl-5,7-dihydro-6H-pyrrolo[2,3-d]pyrimidin-6-one |
| 14 | 4-amino-2-[5-fluoro-3-(2-fluorobenzyl)-1H-indazol-1-yl]-5,5-dimethyl-5,7-dihydro-6H-pyrrolo[2,3-d]pyrimidin-6-one |
| 15 | 4-amino-2-[5-chloro-3-(2,3-difluorobenzyl)-1H-indazol-1-yl]-5,5-dimethyl-5,7-dihydro-6H-pyrrolo[2,3-d]pyrimidin-6-one |
| 16 | 4-amino-2-[3-(2,3-difluorobenzyl)-5-fluoro-1H-indazol-1-yl]-5,5-dimethyl-5,7-dihydro-6H-pyrrolo[2,3-d]pyrimidin-6-one |
| 17 | 4-amino-2-[3-(2,3-difluorobenzyl)-1H-indazol-1-yl]-5,5-dimethyl-5,7-dihydro-6H-pyrrolo[2,3-d]pyrimidin-6-one |
| 18 | 4-amino-2-[3-(2-fluorobenzyl)-5-phenyl-1H-indazol-1-yl]-5,5-dimethyl-5,7-dihydro-6H-pyrrolo[2,3-d]pyrimidin-6-one |
| 19 | 4-amino-2-[5-fluoro-3-(2,3,6-trifluorobenzyl)-1H-indazol-1-yl]-5,5-dimethyl-5,7-dihydro-6H-pyrrolo[2,3-d]pyrimidin-6-one |
| 20 | 4-amino-5,5-dimethyl-2-[5-pyridin-3-yl-3-(2,3,6-trifluorobenzyl)-1H-indazol-1-yl]-5,7-dihydro-6H-pyrrolo[2,3-d]pyrimidin-6-one |
| 21 | 4-amino-5,5-dimethyl-2-[5-(1-methyl-1H-pyrazol-4-yl)-3-(2,3,6-trifluorobenzyl)-1H-indazol-1-yl]-5,7-dihydro-6H-pyrrolo[2,3-d]pyrimidin-6-one |
| 22 | 4-amino-2-[5-(3,5-dimethyl-1H-pyrazol-4-yl)-3-(2,3,6-trifluorobenzyl)-1H-indazol-1-yl]-5,5-dimethyl-5,7-dihydro-6H-pyrrolo[2,3-d]pyrimidin-6-one |
| 23 | 4-amino-2-[5-(3-furyl)-3-(2,3,6-trifluorobenzyl)-1H-indazol-1-yl]-5,5-dimethyl-5,7-dihydro-6H-pyrrolo[2,3-d]pyrimidin-6-one |
| 24 | 4-amino-5,5-dimethyl-2-[5-(4-methyl-3-thienyl)-3-(2,3,6-trifluorobenzyl)-1H-indazol-1-yl]-5,7-dihydro-6H-pyrrolo[2,3-d]pyrimidin-6-one |
| 25 | 4-amino-2-[5-cyclopropyl-3-(2,3,6-trifluorobenzyl)-1H-indazol-1-yl]-5,5-dimethyl-5,7-dihydro-6H-pyrrolo[2,3-d]pyrimidin-6-one |
| 26 | 4-amino-5,5-dimethyl-2-[5-pyridin-4-yl-3-(2,3,6-trifluorobenzyl)-1H-indazol-1-yl]-5,7-dihydro-6H-pyrrolo[2,3-d]pyrimidin-6-one |
| 27 | 4-amino-5,5-dimethyl-2-[5-phenyl-3-(2,3,6-trifluorobenzyl)-1H-indazol-1-yl]-5,7-dihydro-6H-pyrrolo[2,3-d]pyrimidin-6-one |
| 28 | 4-amino-2-[5-chloro-3-(pyrimidin-5-ylmethyl)-1H-indazol-1-yl]-5,5-dimethyl-5,7-dihydro-6H-pyrrolo[2,3-d]pyrimidin-6-one |
| 29 | 4-amino-5,5-dimethyl-2-[5-(3-thienyl)-3-(2,3,6-trifluorobenzyl)-1H-indazol-1-yl]-5,7-dihydro-6H-pyrrolo[2,3-d]pyrimidin-6-one |
| 30 | 4-amino-2-[5-(5-fluoropyridin-3-yl)-3-(2,3,6-trifluorobenzyl)-1H-indazol-1-yl]-5,5-dimethyl-5,7-dihydro-6H-pyrrolo[2,3-d]pyrimidin-6-one |
| 31 | 4-amino-2-[5-(6-fluoropyridin-3-yl)-3-(2,3,6-trifluorobenzyl)-1H-indazol-1-yl]-5,5-dimethyl-5,7-dihydro-6H-pyrrolo[2,3-d]pyrimidin-6-one |
| 32 | 4-amino-5,5-dimethyl-2-{3-(2,3,6-trifluorobenzyl)-5-[5-(trifluoromethyl)pyridin-3-yl]-1H-indazol-1-yl}-5,7-dihydro-6H-pyrrolo[2,3-d]pyrimidin-6-one |
| 33 | 4-amino-2-[3-(6-bromo-2,3-difluorobenzyl)-5-chloro-1H-indazol-1-yl]-5,5-dimethyl-5,7-dihydro-6H-pyrrolo[2,3-d]pyrimidin-6-one |
| 34 | 4-amino-2-[3-(2-cyclopentylethyl)-1H-indazol-1-yl]-5,5-dimethyl-5,7-dihydro-6H-pyrrolo[2,3-d]pyrimidin-6-one |

-continued

| Example | IUPAC NAME |
|---|---|
| 35 | 4-amino-2-(5-fluoro-3-pentyl-1H-indazol-1-yl)-5,5-dimethyl-5,7-dihydro-6H-pyrrolo[2,3-d]pyrimidin-6-one |
| 36 | 4-amino-2-[5-fluoro-3-(3,3,3-trifluoropropyl)-1H-indazol-1-yl]-5,5-dimethyl-5,7-dihydro-6H-pyrrolo[2,3-d]pyrimidin-6-one |
| 37 | 4-amino-2-[3-(2-cyclopentylethyl)-5-fluoro-1H-indazol-1-yl]-5,5-dimethyl-5,7-dihydro-6H-pyrrolo[2,3-d]pyrimidin-6-one |
| 38 | 4-amino-2-[3-(2-cyclopentylethyl)-5-fluoro-1H-indazol-1-yl]-5,5-dimethyl-5,7-dihydro-6H-pyrrolo[2,3-d]pyrimidin-6-one |
| 39 | 4-amino-2-[5-fluoro-3-(4,4,4-trifluorobutyl)-1H-indazol-1-yl]-5,5-dimethyl-5,7-dihydro-6H-pyrrolo[2,3-d]pyrimidin-6-one |
| 40 | 4-amino-2-(5-chloro-3-pentyl-1H-indazol-1-yl)-5,5-dimethyl-5,7-dihydro-6H-pyrrolo[2,3-d]pyrimidin-6-one |
| 41 | 4-amino-2-(3-butyl-5-chloro-1H-indazol-1-yl)-5,5-dimethyl-5,7-dihydro-6H-pyrrolo[2,3-d]pyrimidin-6-one |
| 42 | 4-amino-2-[5-chloro-3-(4,4,4-trifluorobutyl)-1H-indazol-1-yl]-5,5-dimethyl-5,7-dihydro-6H-pyrrolo[2,3-d]pyrimidin-6-one |
| 43 | 4-amino-2-(5-chloro-3-pent-4-en-1-yl-1H-indazol-1-yl)-5,5-dimethyl-5,7-dihydro-6H-pyrrolo[2,3-d]pyrimidin-6-one |
| 44 | 4-amino-2-(3-but-3-en-1-yl-5-chloro-1H-indazol-1-yl)-5,5-dimethyl-5,7-dihydro-6H-pyrrolo[2,3-d]pyrimidin-6-one |
| 45 | 4-amino-2-(5-chloro-3-propyl-1H-indazol-1-yl)-5,5-dimethyl-5,7-dihydro-6H-pyrrolo[2,3-d]pyrimidin-6-one |
| 46 | ethyl 3-[1-(4-amino-5,5-dimethyl-6-oxo-6,7-dihydro-5H-pyrrolo[2,3-d]pyrimidin-2-yl)-5-chloro-1H-indazol-3-yl]propanoate |
| 47 | 4-amino-2-[5-chloro-3-(3,3-dimethylbutyl)-1H-indazol-1-yl]-5,5-dimethyl-5,7-dihydro-6H-pyrrolo[2,3-d]pyrimidin-6-one |
| 48 | 4-amino-2-[3-(2,3-difluorobenzyl)-1H-thieno[3,4-c]pyrazol-1-yl]-5,5-dimethyl-5,7-dihydro-6H-pyrrolo[2,3-d]pyrimidin-6-one |
| 49 | 4-amino-2-[6-chloro-3-(2,3-difluorobenzyl)-1H-thieno[3,4-c]pyrazol-1-yl]-5,5-dimethyl-5,7-dihydro-6H-pyrrolo[2,3-d]pyrimidin-6-one |
| 50 | 4-amino-2-[5-chloro-3-(2,3-difluorobenzyl)-1H-thieno[2,3-c]pyrazol-1-yl]-5,5-dimethyl-5,7-dihydro-6H-pyrrolo[2,3-d]pyrimidin-6-one |
| 51 | 4-amino-2-[3-(2,3-difluorobenzyl)-1H-thieno[3,2-c]pyrazol-1-yl]-5,5-dimethyl-5,7-dihydro-6H-pyrrolo[2,3-d]pyrimidin-6-one |
| 52 | 4-amino-2-[5-chloro-3-(2,3,6-trifluorobenzyl)-1H-thieno[2,3-c]pyrazol-1-yl]-5,5-dimethyl-5,7-dihydro-6H-pyrrolo[2,3-d]pyrimidin-6-one |
| 53 | 4-amino-5,5-dimethyl-2-[3-(2,3,6-trifluorobenzyl)-1H-thieno[3,2-c]pyrazol-1-yl]-5,7-dihydro-6H-pyrrolo[2,3-d]pyrimidin-6-one |
| 54 | 4-amino-5,5-dimethyl-2-[5-methyl-3-(2,3,6-trifluorobenzyl)pyrazolo[4,3-c]pyrazo-1(5H)-yl]-5,7-dihydro-6H-pyrrolo[2,3-d]pyrimidin-6-one |
| 55 | 4-amino-5,5-dimethyl-2-[3-(2,3,6-trifluorobenzyl)-1H-thieno[2,3-c]pyrazol-1-yl]-5,7-dihydro-6H-pyrrolo[2,3-d]pyrimidin-6-one |
| 56 | 4-amino-5,5-dimethyl-2-[6-methyl-3-(2,3,6-trifluorobenzyl)pyrazolo[3,4-c]pyrazo-1(6H)-yl]-5,7-dihydro-6H-pyrrolo[2,3-d]pyrimidin-6-one |
| 57 | 4-amino-5,5-dimethyl-2-[3-(2,3,6-trifluorobenzyl)-1H-pyrazolo[4,3-c]pyridin-1-yl]-5,7-dihydro-6H-pyrrolo[2,3-d]pyrimidin-6-one |
| 58 | 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one |
| 59 | 4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 60 | 4-amino-2-[6-fluoro-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 61 | 4-amino-5,5-dimethyl-2-[5-(2,3,6-trifluorobenzyl)imidazo[5,1-b][1,3]thiazol-7-yl]-5,7-dihydro-6H-pyrrolo[2,3-d]pyrimidin-6-one |
| 62 | 4-amino-5,5-dimethyl-2-[1-(2,3,6-trifluorobenzyl)imidazo[1,5-a]pyridin-3-yl]-5,7-dihydro-6H-pyrrolo[2,3-d]pyrimidin-6-one |
| 63 | 4-amino-2-[3-(2,3-difluorobenzyl)imidazo[1,5-a]pyridin-1-yl]-5,5-dimethyl-5,7-dihydro-6H-pyrrolo[2,3-d]pyrimidin-6-one |
| 64 | 4-amino-2-[7-(2,3-difluorobenzyl)imidazo[1,5-b]pyridazin-5-yl]-5,5-dimethyl-5,7-dihydro-6H-pyrrolo[2,3-d]pyrimidin-6-one |
| 65 | 4-amino-2-[3-(2,3-difluorobenzyl)-6-fluoroimidazo[1,5-a]pyridin-1-yl]-5,5-dimethyl-5,7-dihydro-6H-pyrrolo[2,3-d]pyrimidin-6-one |
| 66 | 4-amino-2-[7-(2-fluorobenzyl)imidazo[1,5-b]pyridazin-5-yl]-5,5-dimethyl-5,7-dihydro-6H-pyrrolo[2,3-d]pyrimidin-6-one |
| 67 | 4-amino-2-[3-(2-fluorobenzyl)imidazo[1,5-a]pyridin-1-yl]-5,5-dimethyl-5,7-dihydro-6H-pyrrolo[2,3-d]pyrimidin-6-one |
| 68 | 4-amino-2-[6-fluoro-3-(2-fluorobenzyl)imidazo[1,5-a]pyridin-1-yl]-5,5-dimethyl-5,7-dihydro-6H-pyrrolo[2,3-d]pyrimidin-6-one |
| 69 | 4-amino-2-[6-chloro-3-(2-fluorobenzyl)imidazo[1,5-a]pyridin-1-yl]-5,5-dimethyl-5,7-dihydro-6H-pyrrolo[2,3-d]pyrimidin-6-one |
| 70 | 4-amino-2-[7-(2,3-difluorobenzyl)-2-methylimidazo[1,5-b]pyridazin-5-yl]-5,5-dimethyl-5,7-dihydro-6H-pyrrolo[2,3-d]pyrimidin-6-one |
| 71 | 4-amino-2-[6-chloro-3-(2,3-difluorobenzyl)imidazo[1,5-a]pyridin-1-yl]-5,5-dimethyl-5,7-dihydro-6H-pyrrolo[2,3-d]pyrimidin-6-one |
| 72 | 4-amino-2-(3-benzylimidazo[1,5-a]pyridin-1-yl)-5,5-dimethyl-5,7-dihydro-6H-pyrrolo[2,3-d]pyrimidin-6-one |
| 73 | 4-amino-5,5-dimethyl-2-[3-(2,3,6-trifluorobenzyl)imidazo[1,5-a]pyridin-1-yl]-5,7-dihydro-6H-pyrrolo[2,3-d]pyrimidin-6-one |

-continued

| Example | IUPAC NAME |
|---|---|
| 74 | 4-amino-5,5-dimethyl-2-[6-phenyl-3-(2,3,6-trifluorobenzyl)imidazo[1,5-a]pyridin-1-yl]-5,7-dihydro-6H-pyrrolo[2,3-d]pyrimidin-6-one |
| 75 | 4-amino-2-[6-(2-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 76 | 4-amino-2-[6-(3-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 77 | 4-amino-2-[6-(4-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 78 | 4-amino-2-[6-(3-chlorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 79 | 4-amino-5,5-dimethyl-2-[6-(3-thienyl)-3-(2,3,6-trifluorobenzyl)imidazo[1,5-a]pyridin-1-yl]-5,7-dihydro-6H-pyrrolo[2,3-d]pyrimidin-6-one |
| 80 | 4-amino-2-[6-cyclopropyl-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 81 | 4-amino-5,5-dimethyl-2-[7-(3,3,3-trifluoropropyl)imidazo[1,5-b]pyridazin-5-yl]-5,7-dihydro-6H-pyrrolo[2,3-d]pyrimidin-6-one |
| 82 | 4-amino-5,5-dimethyl-2-[3-(2,4,6-trifluorobenzyl)imidazo[1,5-a]pyridin-1-yl]-5,7-dihydro-6H-pyrrolo[2,3-d]pyrimidin-6-one |
| 83 | 4-amino-2-[3-(2-chloro-6-fluoro-3-methylbenzyl)imidazo[1,5-a]pyridin-1-yl]-5,5-dimethyl-5,7-dihydro-6H-pyrrolo[2,3-d]pyrimidin-6-one |
| 84 | 4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one |
| 85 | 4-amino-5,5-dimethyl-2-[7-(4,4,4-trifluorobutyl)imidazo[1,5-b]pyridazin-5-yl]-5,7-dihydro-6H-pyrrolo[2,3-d]pyrimidin-6-one |
| 86 | 4-amino-5,5-dimethyl-2-[3-(4,4,4-trifluorobutyl)imidazo[1,5-a]pyridin-1-yl]-5,7-dihydro-6H-pyrrolo[2,3-d]pyrimidin-6-one |
| 87 | 4-amino-5,5-dimethyl-2-{3-[2-(2-thienyl)ethyl]imidazo[1,5-a]pyridin-1-yl}-5,7-dihydro-6H-pyrrolo[2,3-d]pyrimidin-6-one |
| 88 | 4-amino-2-[3-(2-cyclopropylethyl)imidazo[1,5-a]pyridin-1-yl]-5,5-dimethyl-5,7-dihydro-6H-pyrrolo[2,3-d]pyrimidin-6-one |
| 89 | 4-amino-5,5-dimethyl-2-(3-pentylimidazo[1,5-a]pyridin-1-yl)-5,7-dihydro-6H-pyrrolo[2,3-d]pyrimidin-6-one |
| 90 | 4-amino-5,5-dimethyl-2-(7-pentylimidazo[1,5-b]pyridazin-5-yl)-5,7-dihydro-6H-pyrrolo[2,3-d]pyrimidin-6-one |
| 91 | 4-amino-5,5-dimethyl-2-[3-(3-methylbutyl)imidazo[1,5-a]pyridin-1-yl]-5,7-dihydro-6H-pyrrolo[2,3-d]pyrimidin-6-one |
| 92 | 4-amino-5,5-dimethyl-2-[3-methyl-5-(2,3,6-trifluorobenzyl)imidazo[5,1-b][1,3]thiazol-7-yl]-5,7-dihydro-6H-pyrrolo[2,3-d]pyrimidin-6-one |
| 93 | 4-amino-5,5-dimethyl-2-[2-methyl-5-(2,3,6-trifluorobenzyl)imidazo[5,1-b][1,3]thiazol-7-yl]-5,7-dihydro-6H-pyrrolo[2,3-d]pyrimidin-6-one |
| 94 | 4-amino-2-[5-(2-fluorobenzyl)imidazo[5,1-b][1,3]thiazol-7-yl]-5,5-dimethyl-5,7-dihydro-6H-pyrrolo[2,3-d]pyrimidin-6-one |
| 95 | 4-amino-5,5-dimethyl-2-[1-(3,3,3-trifluoropropyl)-1H-indazol-3-yl]-5,7-dihydro-6H-pyrrolo[2,3-d]pyrimidin-6-one |
| 96 | 4-amino-2-[5-chloro-3-(2,3,6-trifluorobenzyl)-1H-indazol-1-yl]-5,5-dimethyl-5,8-dihydropyrido[2,3-d]pyrimidin-7(6H)-one |
| 97 | 4-amino-5,5-dimethyl-2-[3-(2,3,6-trifluorobenzyl)-1H-indazol-1-yl]-5,8-dihydropyrido[2,3-d]pyrimidin-7(6H)-one |
| 98 | 4-amino-5,5-dimethyl-2-[3-(2,3,6-trifluorobenzyl)-1H-thieno[3,4-c]pyrazol-1-yl]-5,8-dihydropyrido[2,3-d]pyrimidin-7(6H)-one |
| 99 | 4-amino-5,5-dimethyl-2-[3-(2,3,6-trifluorobenzyl)-4,6-dihydro-1H-thieno[3,4-c]pyrazol-1-yl]-5,8-dihydropyrido[2,3-d]pyrimidin-7(6H)-one |
| 100 | 4-amino-2-[5-chloro-3-(3,3,3-trifluoropropyl)-1H-indazol-1-yl]-5-ethyl-5-methyl-5,7-dihydro-6H-pyrrolo[2,3-d]pyrimidin-6-one |
| 101 | 4-amino-2-[5-chloro-3-(3,3,3-trifluoropropyl)-1H-indazol-1-yl]-5-methyl-5-propy-5,7-dihydro-6H-pyrrolo[2,3-d]pyrimidin-6-one |
| 102 | 4-amino-2-[5-chloro-3-(3,3-dimethylbutyl)-1H-indazol-1-yl]-5-ethyl-5-methyl-5,7-dihydro-6H-pyrrolo[2,3-d]pyrimidin-6-one |
| 103 | 4-amino-5-ethyl-2-[3-(2-fluorobenzyl)imidazo[1,5-a]pyridin-1-yl]-5-methyl-5,7-dihydro-6H-pyrrolo[2,3-d]pyrimidin-6-one |
| 104 | 4-amino-5,5-dimethyl-2-[3-(3,3,4,4,4-pentafluorobutyl)-1H-indazol-1-yl]-5,7-dihydro-6H-pyrrolo[2,3-d]pyrimidin-6-one |
| 105 | 4-amino-2-[5-fluoro-3-(3,3,4,4,4-pentafluorobutyl-1H-indazol-1-yl]5,5-dimethyl-5,7-dihydro-6H-pyrrolo[2,3-d]pyrimidin-6-one |
| 106 | 4-amino-2-[5-chloro-3-(3,3,4,4,4-pentafluorobutyl)-1H-indazol-1-yl]-5,5-dimethy-5,7-dihydro-6H-pyrrolo[2,3-d]pyrimidin-6-one |
| 107 | 4-amino-5,5-dimethyl-2-[3-(3,3,4,4,4-pentafluorobutyl)-1H-pyrazolo[4,3-b]pyridin-1-yl]-5,7-dihydro-6H-pyrrolo[2,3-d]pyrimidin-6-one |
| 108 | 4-amino-5,5-dimethyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 109 | 4-amino-2-[6-fluoro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one |

-continued

| Example | IUPAC NAME |
|---|---|
| 110 | 4-amino-2-[6-chloro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one |
| 111 | 4-amino-2-[6-chloro-1-(3,3,4,4,4-pentafluorobutyl)-1H-indazol-3-yl]-5,5-dimethyl-5,7-dihydro-6H-pyrrolo[2,3-d]pyrimidin-6-one | and pharmaceutically acceptable salts thereof.

In a further embodiment, a compound of the instant invention is selected from:

4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one;

4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one;

4-amino-5,5-dimethyl-2-[3-(2,3,6-trifluorobenzyl)-1H-thieno[3,4-c]pyrazol-1-yl]-5,7-dihydro-6H-pyrrolo[2,3-d]pyrimidin-6-one;

4-amino-2-[5-chloro-3-(2,3,6-trifluorobenzyl)-1H-thieno[2,3-c]pyrazol-1-yl]-5,5-dimethyl-5,7-dihydro-6H-pyrrolo[2,3-d]pyrimidin-6-one 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one;

4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one;

4-amino-2-[6-fluoro-3-(2,3,6-trifluorobenzyl)imidazo[1,5-a]pyridin-1-yl]-5,5-dimethyl-5,7-dihydro-6H-pyrrolo[2,3-d]pyrimidin-6-one;

4-amino-2-[3-(2,3-difluorobenzyl)-6-fluoroimidazo[1,5-c]pyridin-1-yl]-5,5-dimethyl-5,7-dihydro-6H-pyrrolo[2,3-d]pyrimidin-6-one;

4-amino-5,5-dimethyl-2-[3-(2,3,6-trifluorobenzyl)imidazo[1,5-a]pyridin-1-yl]-5,7-dihydro-6H-pyrrolo[2,3-d]pyrimidin-6-one;

4-amino-2-[3-(2-cyclopentylethyl)imidazo[1,5-d]pyridin-1-yl]-5,5-dimethyl-5,7-dihydro-6H-pyrrolo[2,3-d]pyrimidin-6-one;

and pharmaceutically acceptable salts thereof.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or $CH_3$ or a symbol that is an extended bond without defined terminal group, e.g. "⊱—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. If no number is specified, 1-10 carbon atoms are intended for linear or branched alkyl groups. The phrase "$C_{1-6}$ alkyl, wherein the alkyl group may be unsubstituted or substituted with 1-3 fluorine atoms" refers to alkyl groups having 0, 1, 2 or 3 fluorine atoms attached to one or more carbon atoms. The group "$CF_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. The preferred aryl is phenyl.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl", unless otherwise indicated, means a 5- or 6-membered monocyclic saturated ring containing at least one heteroatom selected from N, S and O, in which the point of attachment may be carbon or nitrogen. Examples of "heterocyclyl" include, but are not limited to, pyrrolidinyl, piperidinyl, piperazinyl, morpholinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen (or halo)" unless otherwise indicated, includes fluorine (fluoro), chlorine (chloro), bromine (bromo) and iodine (iodo). Fluoro and chloro are preferred.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the Formula I or at the stage of an intermediate during the synthesis. The present invention also includes all tautomeric forms of the compounds of Formula I.

If the compounds of the Formula I contain one or more acidic or basic groups the invention also includes the corresponding physiologically or toxicologically acceptable salts, in particular the pharmaceutically utilizable salts. Thus, the compounds of the Formula I which contain acidic groups can be present on these groups and can be used according to the invention, for example, as alkali metal salts, alkaline earth metal salts or as ammonium salts. Examples of such salts are sodium salts, potassium salts, calcium salts, magnesium salts or salts with ammonia or organic amines such as, for example, ethylamine, ethanolamine, triethanolamine or amino acids. Compounds of the Formula I which contain one or more basic groups, i.e. groups which can be protonated, can be present and can be used according to the invention in the form of their acid addition salts with inorganic or organic acids, for example as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of the Formula I simultaneously contain acidic and basic groups in the molecule the invention also includes, in addition to the salt forms mentioned, inner salts or betaines (zwitterions). Salts can be obtained from the compounds of the Formula I by customary methods which are known to the person skilled in the art, for example by combination with an organic or inorganic acid or base in a solvent or dispersant, or by anion exchange or cation exchange from other salts. The present invention also includes all salts of the compounds of the Formula I which, owing to low physiological compatibility, are not directly suitable for use in pharmaceuticals but which can be used, for example, as intermediates for chemical reactions or for the preparation of physiologically acceptable salts.

As illustrated by the examples herein,

represents an 8- or 9-membered bicyclic heteroaryl ring system, comprised of a 5-membered ring fused to a 5- or 6-membered ring so that the fused rings share two adjacent atoms. In particular, the 8- or 9-membered heteroaryl is composed of a first ring which is a 5-membered ring containing two nitrogens, fused to a second ring that optionally contains one or more heteroatoms (N, O or S). The two nitrogens of the first ring may be fully in the first ring, or one of the two nitrogens may be shared at a fusion point with the second ring. The 8- or 9-membered bicyclic heteroaryl is attached to the pyrmidinyl ring and the —CH$_2$—R$^2$ group of structural Formula I or II via the first ring, and more specifically via each of the atoms in the first ring that are adjacent to each of the two atoms shared by both rings in the bicyclic heteroaryl.

In an embodiment,

is

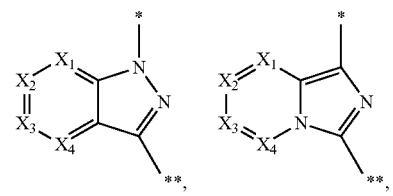

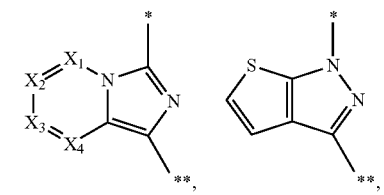

-continued

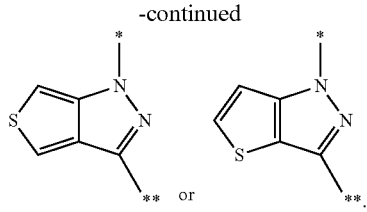

In another embodiment,

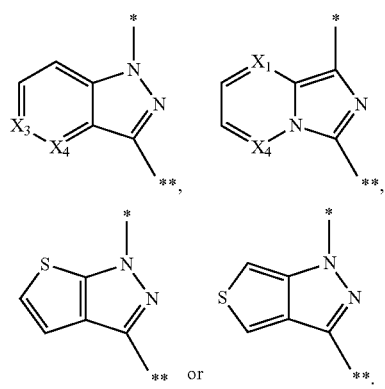

wherein $X^1$, $X^3$ and $X^4$ are selected from CH or N, provided no more than one is N.

In a further embodiment,

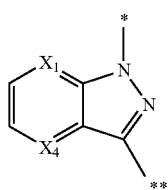

and $X^1$ and $X^4$ are CH. As used herein, * indicates attachment to the pyrmidinyl ring and ** indicates attachment to the —CH$_2$—R$^2$ of structural Formula I or II.

In an embodiment, R$^1$ is independently selected from H, halo, aryl, heteroaryl, —C$_1$-C$_6$ alkyl, and —C$_{3-10}$cycloalkyl, said aryl, heteroaryl, alkyl and cycloalkyl optionally being substituted with one to three substituents selected from halo, —C$_1$-C$_6$ alkyl, —OR, oxo and —CF$_3$. In a further embodiment, R$^1$ is aryl or —C$_1$-C$_6$ alkyl, wherein said aryl or —C$_1$-C$_6$ alkyl is optionally substituted with one to three substituents selected from halo or —CF$_3$.

In an embodiment, R$^2$ is selected from —C$_1$-C$_6$ alkyl, —(CR$^a{}_2$)$_r$—C$_{3-10}$cycloalkyl, —(CR$^a{}_2$)$_r$aryl, —(CR$^a{}_2$)$_r$heteroaryl, and —(CR$^a{}_2$)$_r$C(O)Oalkyl, said alkyl, cycloalkyl, aryl, and heteroaryl being optionally substituted with one to three substituents selected from halo, —C$_1$-C$_6$ alkyl, —CF$_3$, —CN and —OR. In another embodiment, R$^2$ is selected from —C$_1$-C$_6$ alkyl and —(CR$^a{}_2$)$_r$aryl, said alkyl and aryl being optionally substituted with one to three substituents selected from halo, —C$_1$-C$_6$ alkyl and —CF$_3$.

When R$^3$ and R$^4$ are both alkyl, they may be joined together with the carbon to which they are commonly attached to form a 3-6 membered cycloalkyl ring. In an embodiment, R$^3$ and R$^4$ are each C$_1$-C$_6$ alkyl. In a further embodiment, R$^3$ and R$^4$ are each methyl.

The present invention also relates to processes for the preparation of the compounds of the Formula I which are described in the following and by which the compounds of the invention are obtainable.

The compounds of the Formula I according to the invention effect an increase of the cGMP concentration via the activation of the soluble guanylate cyclase (sGC), and they are therefore useful agents for the therapy and prophylaxis of disorders which are associated with a low or decreased cGMP level or which are caused thereby, or for whose therapy or prophylaxis an increase of the present cGMP level is desired. The activation of the sGC by the compounds of the Formula I can be examined, for example, in the activity assay described below.

Disorders and pathological conditions which are associated with a low cGMP level or in which an increase of the cGMP level is desired and for whose therapy and prophylaxis it is possible to use compounds of the Formula I are, for example, cardiovascular diseases, such as endothelial dysfunction, diastolic dysfunction, atherosclerosis, hypertension, heart failure, pulmonary hypertension, stable and unstable angina pectoris, thromboses, restenosis, myocardial infarction, strokes, cardiac insufficiency or pulmonary hypertonia, or, for example, erectile dysfunction, asthma bronchiale, chronic kidney insufficiency and diabetes. Compounds of the Formula I can additionally be used in the therapy of cirrhosis of the liver and also for improving a restricted memory performance or ability to learn.

The compounds of the Formula I and their physiologically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

A subject of the present invention therefore also are the compounds of the Formula I and their physiologically acceptable salts for use as pharmaceuticals, their use for activating soluble guanylate cyclase, for normalizing a disturbed cGMP balance and in particular their use in the therapy and prophylaxis of the abovementioned syndromes as well as their use for preparing medicaments for these purposes.

A therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of the Formula I and/or a physiologically acceptable salt thereof and a customary pharmaceutically acceptable carrier, i.e., one or more pharmaceutically acceptable carrier substances and/or additives.

Thus, a subject of the invention are, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the Formula I and/or its physiologically acceptable salts in the pharmaceutical preparations normally is from 0.2 to 200 mg, preferably from 1 to 200 mg, per dose, but depending on the type of the pharmaceutical preparation it can also be higher. The pharmaceutical preparations usually comprise 0.5 to 90 percent by weight of the compounds of the Formula I and/or their physiologically acceptable salts. The preparation of the pharmaceutical preparations can be carried out in a manner known per se. For this purpose, one or more compounds of the Formula I and/or their physiologically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc.

Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their physiologically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the Formula I to be administered and/or of a physiologically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the Formula I activate the soluble guanylate cyclase. On account of this property, apart from use as pharmaceutically active compounds in human medicine and veterinary medicine, they can also be employed as a scientific tool or as aid for biochemical investigations in which such an effect on guanylate cyclase is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

The above-mentioned compounds are also of use in combination with other pharmacologically active compounds comprising angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losratan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471);

also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075, The compounds of Formula I can be synthesized in accordance with the general schemes provided below where $R^1$, $R^2$, $R^3$, and $R^4$ are defined as above (unless otherwise indicated), taking into account the specific examples that are provided. Throughout the synthetic schemes and examples, abbreviations are used with the following meanings unless otherwise indicated:

| | |
|---|---|
| aq, aq. = aqueous | BuLi, n-BuLi = n-butyllithium |
| Ar = aryl | DME = 1,2-dimethoxyethane |
| Ac = acetate | Bn = benzyl |
| Bu = butyl, t-Bu = tert-butyl | $BF_3 \cdot OEt_2$ = boron trifluoride diethyl etherate |
| $CHCl_3$ = chloroform | |
| cPr = cyclopropyl | conc, conc. = concentrated |
| DCE = dichloroethane | DBU = 1,8-Diazabicyclo[4.3.0]undec-7-ene |
| DCM = dichloromethane | dba = dibenzylideneacetone; $Pd_2dba_3$ = tris(dibenzylidineacetone)dipalladium |
| DIEA = diisopropylethylamine | DMF = N,N-dimethylformamide |
| DMAC, DMA = dimethylacetamide | dppf, DPPF = 1,1'-bis(diphenylphosphino)ferrocene |
| DMSO = dimethylsulfoxide | DIBAL, DIBAL-H = diisobutylaluminum hydride |
| Et = ethyl | EDC = 1-Ethyl-3-(3-dimethylaminopropyl) carbodiimidehydrochloride |
| EtOAc = ethyl acetate | EtOH = ethanol |
| eq. = equivalent(s) | HPLC = High pressure liquid chromatography |
| HOAc - acetic acid | iPA = isopropyl alcohol |
| iPr = isopropyl | LAH = Lithium aluminum hydride |
| h, hr = hour | IPA, i-PrOH = isopropanol |
| LDA = lithium diisopropyl amide | LCMS = liquid chromatography - mass spectroscopy |
| Me = methyl | LiHMDS = lithium bis(trimethylsilyl)amide |
| MeOH = methanol | min, min. = minute |
| Mp = melting point | NaHMDS = sodium bis(trimethylsilyl)amide |
| NBS = N-bromo succinmide | NIS = N-iodosuccinimide |
| NMP = N-methylpyrrolidinone | NMR = nuclear magnetic resonance |
| PDA = photodiode array | Pd/C = palladium on activated carbon |
| PdCl2(dppf)2•CH2Cl2 = Dichloro 1,1'-bis(diphenylphosphino)ferrocene palladium (II) dichloromethane adduct | $Pd_2(dba)_3$ = Tris(dibenzylideneacetone)dipalladium (0) |
| Ph = phenyl | Pr = propyl |
| rt = retention time | RT = room temperature |
| sat. = saturated | TEA = triethylamine |
| THF = tetrahydrofuranTFA = Trifluoroacetic acid | TLC = thin layer chromatography |
| prep TLC = preparative thin layer chromatography | |

451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholytics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

The following examples are provided so that the invention might be more fully understood. Unless otherwise indicated, the starting materials are commercially available. They should not be construed as limiting the invention in any way.

SCHEMES

In one embodiment of the present invention, compounds with structure 1 may be prepared by the sequence depicted in Scheme 1. Ring structure Z represents a five or six membered aryl or heteroaryl ring. Deprotonation of malononitrile 2 with a base such as sodium hydride, potassium t-butoxide or potassium carbonate in the presence of the alpha bromo ester 3 affords the compound 4. The reaction is typically done in a solvent such as DMF or THF. If compound 3 is not commercially available it may be prepared from the corresponding ester by bromination with N-bromosuccinimide in a solvent such as carbon tetrachloride. Reaction of compound 4 with the aminoguanidine hydrazone 5 in an alcohol solvent such as MeOH, n-BuOH or t-BuOH and a base such as NaOMe, NaOEt or t-BuOK at 100° C. to 150° C. gives the pyrimidine hydrazone 6. The reaction may also be carried out in the absence of a base. Compound 1 is prepared by treating compound 6 with CuI and a ligand such as trans-N,N'-dimethylcyclohexane-1,2-diamine or N,N'-dimethylethylenediamine in a solvent such as DMF or NMP at ambient temperature to 160° C. The reaction may also be carried out in the absence of a ligand. The copper mediated cyclization of hydrazones to form indazoles may also be carried out using the conditions described by Liu, R. et al *Synthetic Communications* 2008, 32(2), 249. In addition to the bromide 6, the copper mediated cyclization shown in Scheme 1 may also be carried out on the corresponding chloride or iodide.

The preparation of the aminoguanidine hydrazone 5 is outlined in Scheme 2. Reaction of methyl ester 7 with the carboxylic acid 8 and a base such as NaHMDS in THF gives the ketone 9. The transformation is most effective for aryl acetic acid compounds (8, $R^2$=aryl). Compound 5 is prepared by treatment of the ketone 9 with aminoguanidine hydrochloride and boron trifluoride etherate in an alcohol solvent such as methanol at 100° C.

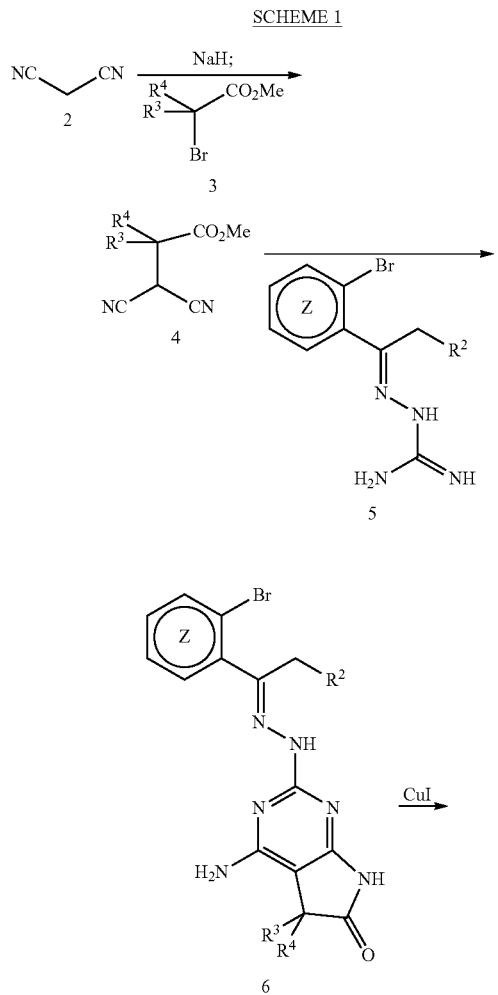

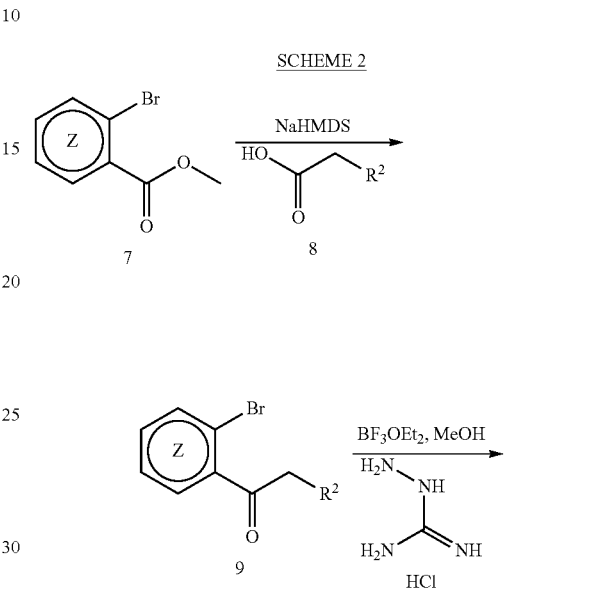

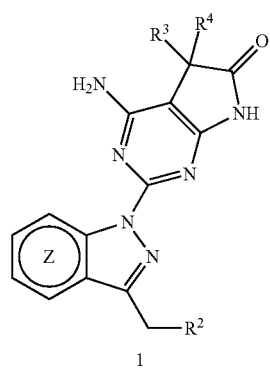

The ketone 9 may be prepared using methods familiar to those skilled in the art. Some of the methods are depicted in Scheme 3. Addition of the alkyl or aryl magnesium chloride 11 (or bromide, iodide) to the aldehyde 10 gives the benzyl alcohol 12. The compound 11, if not commercial, may be prepared from the corresponding halide using magnesium metal as described by Lai, Y. H. *Synthesis* 1981, 585. Ketone 9 is prepared by treating compound 12 with an oxidizing reagent such as chromium trioxide. Ketone 9 may also prepared by the addition of 11 to the amide 15. Alternatively, ketone 9 may be prepared from the acid chloride 13 and the zinc compound 14 using a palladium catalyst such as Pd(PPh$_3$)$_4$ as described by Zhu, L. et al *Journal of Organic Chemistry* 1991, 56(4), 1445. The ketone 9 where $R^2$ is CH$_2$CO$_2$Et may be prepared from the acid chloride 13 and (1-ethoxycyclopropoxy)trimethylsilane using a palladium catalyst such as PdCl$_2$(PPh$_3$)$_2$ as described by Aoki, S. et al *Tetrahedron Letters* 1989, 30(47), 6541.

SCHEME 3

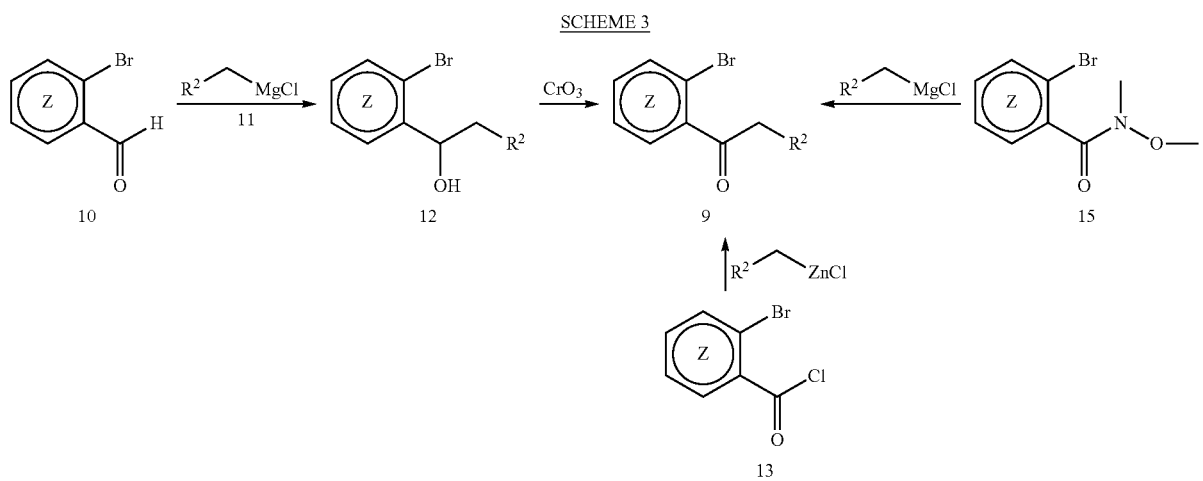

In one embodiment of the present invention compounds with structure 18 (A to D) may be prepared by the sequence depicted in Scheme 4. Conversion of the nitrile 16 to the amidine 17 can be accomplished with a reagent such as amino(chloro)methylaluminum in a non-polar solvent such as toluene at 100° C. as described by Garigipati, R. S. *Tetrahedron Letters* 1990, 31(14), 1969. Reaction of amidine 17 with the malononitrile 4 as described in Scheme 1 affords 18.

SCHEME 4

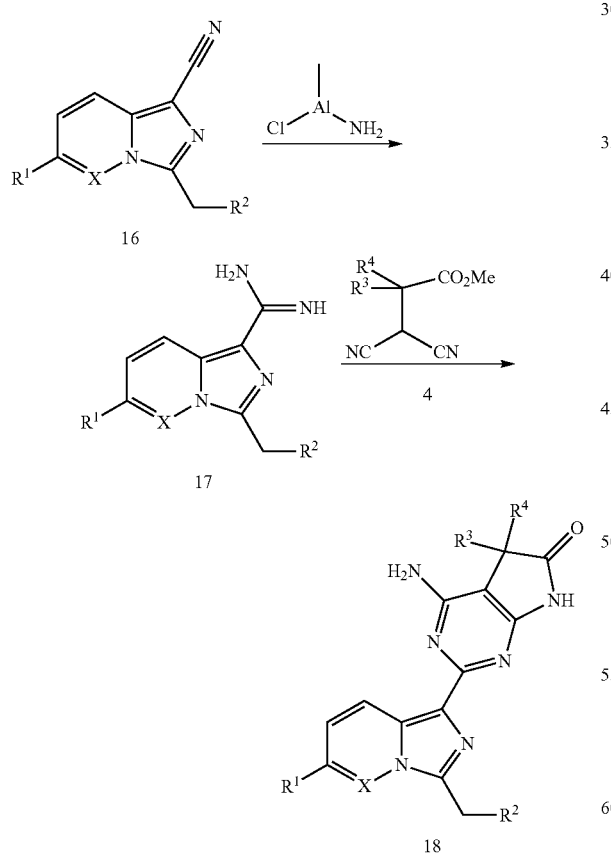

A: $R^1$ = H, X = C
B: $R^1$ = F, X = C
C: $R^1$ = Cl, X = C
D: $R^1$ = H, X = N

Scheme 5 outlines the preparation of nitrile intermediate 16. Amino methyl compound 19 can be coupled with the carboxylic acid 8 and a coupling reagent such as EDC and an organic base such as DIEA or TEA in a solvent like DCM to afford the amide 20. This can be converted to the imidazopyridine 21 with phosphorous oxychloride in a chlorinated solvent such DCE under refluxing conditions. Iodination of 21 to afford 22 can be accomplished with NIS in solvents like DCM or acetonitrile at ambient temperature or under reflux conditions. The nitrile 16 can be prepared by treatment of the iodide 22 with zinc cyanide in the presence of a suitable catalyst such as $Pd(PPh_3)_4$ or $Pd_2(dba)_3$ and ligand such as dppf in a polar solvent such as DMF.

SCHEME 5

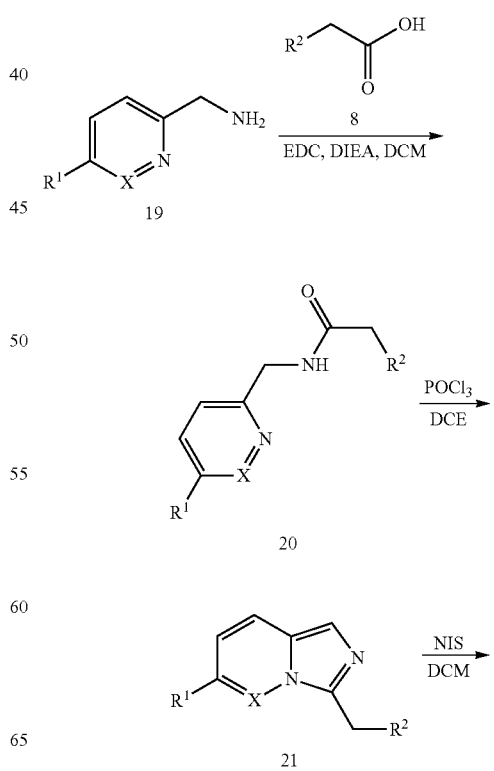

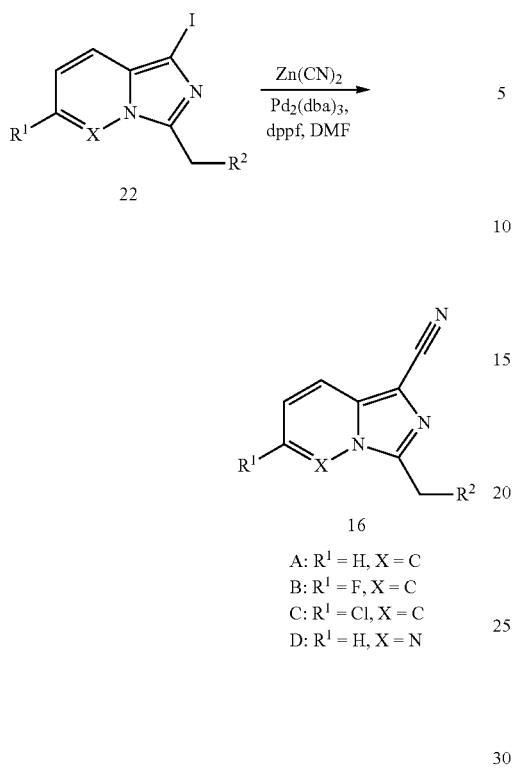

A: R¹ = H, X = C
B: R¹ = F, X = C
C: R¹ = Cl, X = C
D: R¹ = H, X = N

The amino methyl compound 19D may be prepared as outlined in Scheme 6. Pyridazine 23 can be converted to 2-cyano pyridazine 25 using the chemistry described by Dostal, W. and Heinisch, G. *Heterocycles* 1986, 793. Reduction of the nitrile 25 can be accomplished under high pressure hydrogenation conditions using a suitable catalyst such as palladium on carbon in an alcoholic solvent such as methanol or ethanol and a suitable acid such as hydrochloric acid to afford the 2-amino methylpyridazine hydrochloride 19D.

SCHEME 6

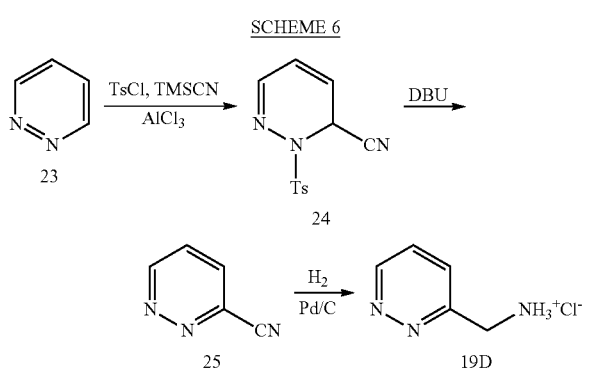

The amino methyl compounds 19B and 19C may be prepared as outlined in Scheme 7. Addition of diethyl acetamidomalonate to 2-chloro-5-nitropyridine affords compound 27. Reduction of 27 with hydrogen and palladium on carbon gives the amine 28. Sandmeyer reaction of 28 using the indicated conditions gives the halo (chloro or fluoro) pyridine 29. Saponification of 29 with base followed by treatment with hydrochloric acid gives amino methyl compounds 19B and 19C.

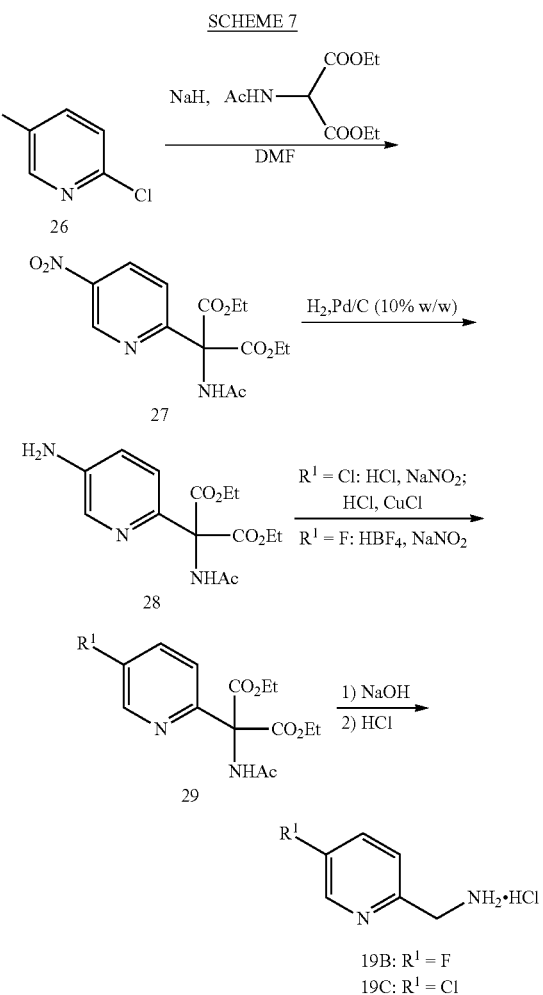

In one embodiment of the present invention compounds with structure 36 are prepared as outlined in Scheme 8. The ketone 30 may be prepared as described for compound 9 in Schemes 2 and 3. Reaction of compound 30 with hydroxylamine in an alcohol solvent affords the oxime 31. Reduction with zinc metal followed by reaction with methyl oxalyl chloride gives compound 33. Cyclization of 33 using phosphorous oxychloride to give 34 may be carried out as described in Scheme 5. Conversion of the ester 34 to the amidine 35 can be accomplished with a reagent such as amino (chloro)methylaluminum in a non-polar solvent such as toluene at 100° C. Reaction of amidine 35 with the malononitrile 4 as described in Scheme 1 affords 36.

SCHEME 8

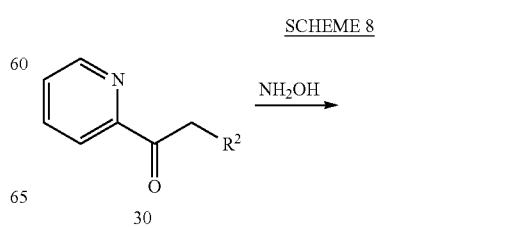

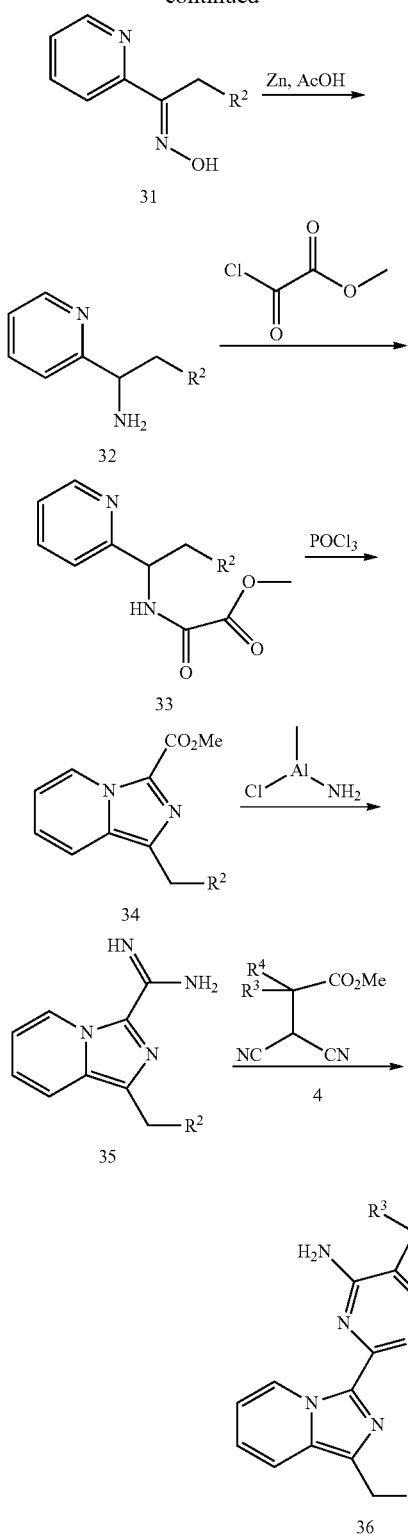

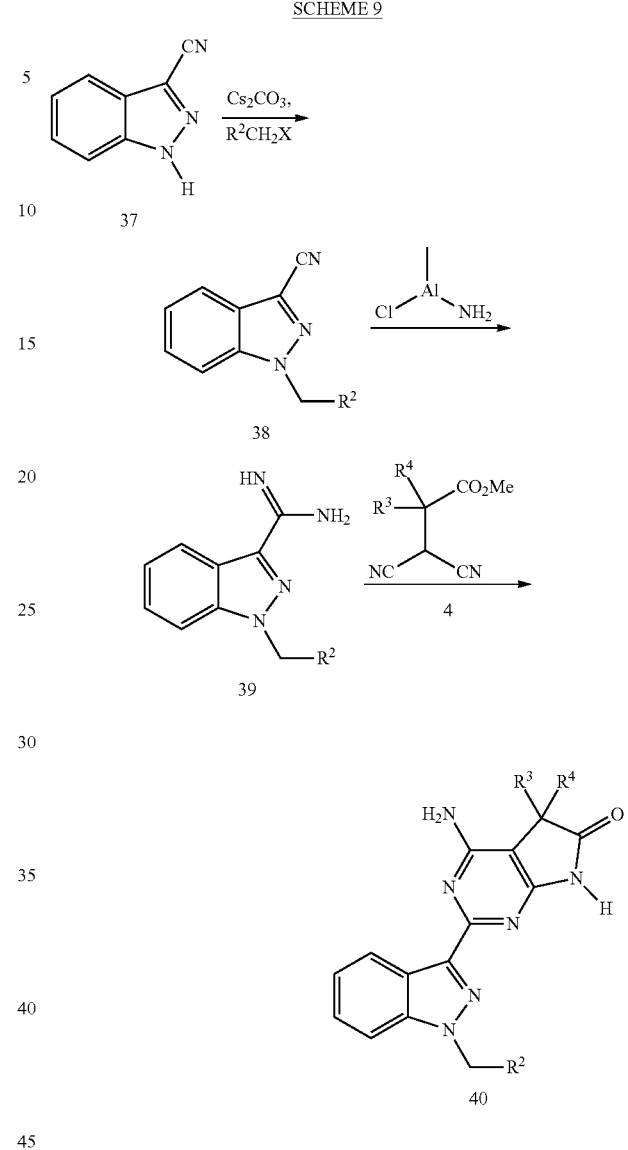

In one embodiment of the present invention compounds with the structure 40 are prepared as outlined in Scheme 9. Alkylation of nitrile indazole 37 with a base such as cesium carbonate or sodium hydride and an alkyl halide in a solvent such as DMF affords the compound 38. Compound 38 can be converted to compound 40 as described in Scheme 4.

In one embodiment of the present invention compounds with the structure 44 are prepared as outlined in Scheme 10. Reaction of the unsaturated nitrile 41 with ethyl bromoacetate, zinc and titanium biscyclopentadienyl dichloride catalyst as described by Ding, Y. et al *Tetrahedron* 1997, 53(8), 249 affords the compound 42. Compound 44 is prepared from compound 42 using the conditions described in Scheme 1. In addition, compound 4 may be substituted with compound 42 in Schemes 4, 8 and 9 to afford the corresponding 6-membered ring amides.

SCHEME 10

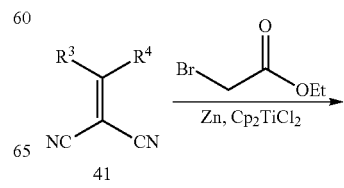

SCHEME 11

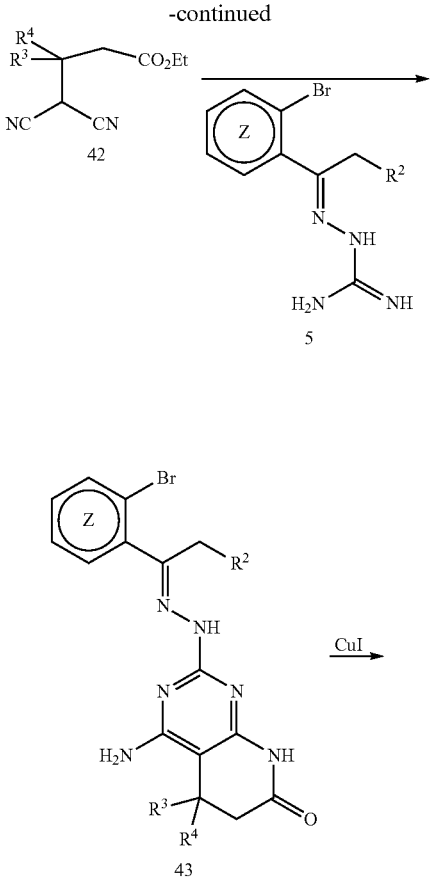

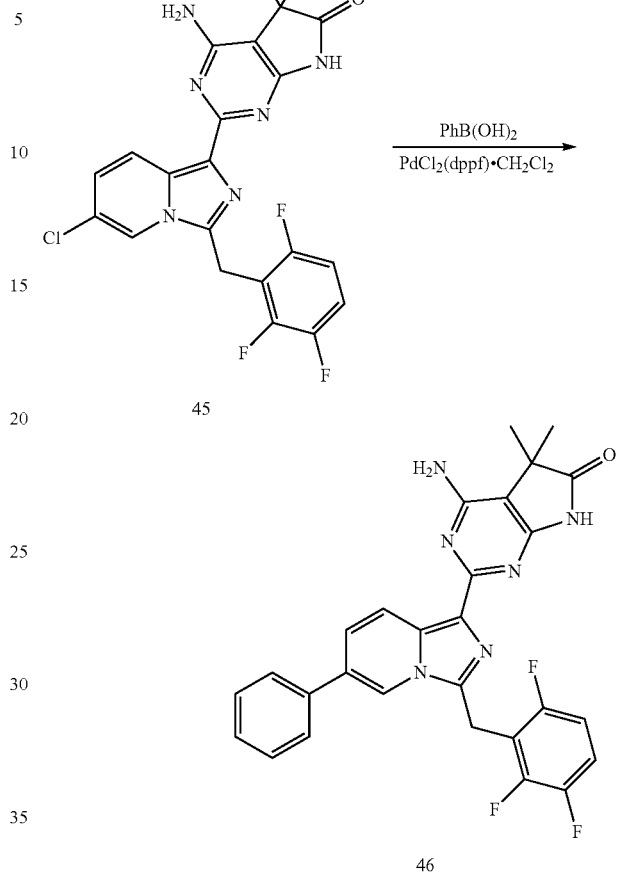

Compounds of the present invention may be prepared using methods familiar to those skilled in the art. One such method is the palladium mediated coupling of a boronic acid or ester and an aryl halide. An example of this method is shown in Scheme 11. The imidazopyridine 45 can be coupled to any suitable boronic acid or boronic ester such as phenyl boronic acid with a catalyst such as dichlorobis[1,1'-bis(diphenylphosphino)ferrocene]palladium (II) dichloromethane adduct to give 46.

REPRESENTATIVE EXAMPLES

The following examples are provided to more fully illustrate the present invention, and shall not be construed as limiting the scope in any manner. Unless stated otherwise:

1) all operations were carried out at room or ambient temperature (RT), that is, at a temperature in the range 18-25° C.;

2) reactions are generally done using commercially available anhydrous solvents under an inert atmosphere, either nitrogen or argon;

3) microwave reactions were done using a Biotage Initiator™ or CEM Explorer® system;

4) evaporation of solvent was carried out using a rotary evaporator under reduced pressure (4.5-30 mmHg) with a bath temperature of up to 50° C.;

5) the course of reactions was followed by thin layer chromatography (TLC) and/or tandem high performance liquid chromatography (HPLC) followed by electron spray mass spectroscopy (MS), herein termed LCMS, and any reaction times are given for illustration only;

6) the structure of all final compounds was assured by at least one of the following techniques: MS or proton nuclear magnetic resonance ($^1$H NMR) spectrometry, and the purity was assured by at least one of the following techniques: TLC or HPLC;

7) $^1$H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;

8) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection; the various methods used for analytical HPLC mass spectrometery conditions are listed below:

Analytical HPLC mass spectrometry conditions:
LC1: Column: Waters Xterra MS C-18, 3.5μ, 3.0×50 mm
Temperature: 50° C.
Eluent: 10:90 to 98:2 v/v acetonitrile/water+0.05% TFA (or HCOOH) over 3.75 min.
Flow Rate: 1.0 mL/min, Injection 10 μL
Detection: PDA, 200-600 nm
MS: mass range 150-750 amu; positive ion electrospray ionization
LC2: Column: Waters Xterra IS C-18, 3.5μ, 2.1×20 mm
Temperature: 50° C.
Eluent: 10:90 to 98:2 v/v acetonitrile/water+0.05% TFA (or HCOOH) over 1.25 min.
Flow Rate: 1.5 mL/min, Injection 5 μL
Detection: PDA, 200-600 nm
MS: mass range 150-750 amu; positive ion electrospray ionization
LC3: Column: Waters Xterra IS C-18, 3.5μ, 2.1×20 mm
Temperature: 50° C.
Eluent: 10:90 to 98:2 v/v acetonitrile/water+0.05% TFA (or HCOOH) over 3.25 min.
Flow Rate: 1.5 mL/min, Injection 5 μL
Detection: PDA, 200-600 nm
MS: mass range 150-750 amu; positive ion electrospray ionization
LC4: Column: Waters Sunfire C18, 5μ, 4.6×50 mm
Temperature: 50° C.
Eluent: 10:90 to 100:0 v/v acetonitrile/water+0.05% TFA over 3.75 min.
Flow Rate: 1.2 mL/min, Injection 10 μL
Detection: PDA, 200-600 nm
MS: mass range 150-700 amu; positive ion electrospray ionization
LC5: Column: YMC Pro C18, 5μ, 4.6×50 mm
Temperature: 50° C.
Eluent: 5:95 to 98:2 v/v acetonitrile/water+0.05% TFA over 3.00 min.
Flow Rate: 2.5 mL/min, Injection 10 μL
Detection: PDA, 200-600 nm
MS: mass range 150-700 amu; positive ion electrospray ionization 9) Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (typically 5% acetonitrile to 95% acetonitrile) or on a Shimadzu system using a Sunfire Prep C18 OBD 5 μM column (100×30 mm i.d.) eluting at 50 mL/min with a water/acetonitrile (0.1% TFA) gradient;

10) Purification of compounds by preparative thin layer chromatography (PTLC) was conducted on 20×20 cm glass plates coated with silica gel, commercially available from Analtech; or E. Merck.

11) flash column chromatography was carried out on a glass silica gel column using Kieselgel 60, 0.063-0.200 mm (SiO₂), or on a Biotage SiO₂ cartridge system using the Biotage Horizon and Biotage SP-1 systems; or a Teledyne Isco SiO₂ cartridge using the CombiFlashRf system;

12) chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), uM (micromolar), nM (nanomolar).

Intermediate 1

METHYL 3,3-DICYANO-2,2-DIMETHYLPROPANOATE

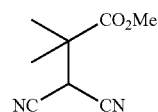

A 12 liter 3 neck round bottom flask equipped with a mechanical stirrer, thermometer, condenser and nitrogen bubbler, was charged with malononitrile (251 g, 3.802 moles) and THF (2 liters). Potassium t-butoxide (1M THF, 3.802 L, 3.802 moles) was then added. The mixture was stirred at 50° C. for 30 min. Methyl 2-bromoisobutyrate (688 g, 3.80 moles) was added and the reaction mixture was stirred overnight at 50° C. The reaction was partitioned between aqueous 1N HCl and EtOAc. The organic phase was washed with brine, dried over MgSO₄, filtered and concentrated to give the indicated product. ¹H NMR (400 MHz, CD₃CN): δ 4.35 (s, 1H); 3.73 (s, 3H); 1.43 (s, 6H).

Intermediate 2

METHYL 2-(DICYANOMETHYL)-2-METHYLBUTANOATE

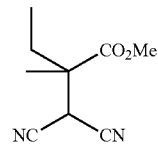

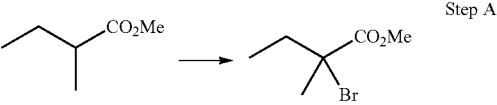

A carbon tetrachloride (30 mL) solution containing methyl 2-methylbutyrate (0.868 g, 7.47 mmol), N-bromosuccinimide (1.4 g, 7.87 mmol) and 2,2'-azobis(2-methylpropionitrile) (0.129 g, 0.787 mmol) was refluxed for 3 hours. The solution was cooled to room temperature and filtered. The filtrate was concentrated and the residue purified by silica gel chromatography using a hexanes/EtOAc gradient to give the indicated product. $^1$H NMR (CDCl$_3$, 400 MHz): δ 3.78 (s, 3H); 2.19-2.09 (m, 2H); 1.87 (s, 3H); 0.98 (t, J=7.4 Hz, 3H).

Step B

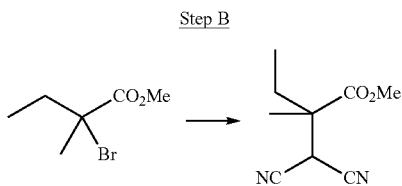

A DMF (4 mL) solution containing malononitrile (0.484 g, 7.32 mmol) was added dropwise to a DMF (3 mL) suspension of sodium hydride (60 wt %, 0.30 g, 7.49 mmol) cooled in an ice bath. After 10 min a DMF (3 mL) solution containing the intermediate from Step A (1.099 g, 5.63 mmol) was added. The ice bath was removed and the solution stirred overnight at room temperature. The solution was partitioned between ethyl ether and aqueous 1N HCl. The organic phase was washed with aqueous 1N HCl, brine and dried over MgSO$_4$. The solution was filtered and concentrated. The residue was purified by silica gel chromatography using a hexanes/EtOAc gradient to give the indicated product. $^1$H NMR (CDCl$_3$, 400 MHz): δ 4.18 (s, 1H); 3.80 (s, 3H); 1.96-1.79 (m, 2H); 1.53 (s, 3H); 0.91 (t, J=7.4 Hz, 3H).

Intermediate 3

METHYL 2-(DICYANOMETHYL)-2-METHYLPENTANOATE

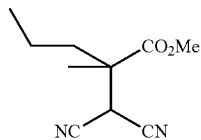

The indicated product was prepared from methyl 2-methylpentanoate as described in Intermediate 2. $^1$H NMR (CDCl$_3$, 400 MHz): δ 4.18 (s, 1H); 3.79 (s, 3H); 1.85-1.70 (m, 2H); 1.52 (s, 3H); 0.31-1.17 (m, 2H); 0.94 (t, J=7.4 Hz, 3H).

Intermediate 4

ETHYL 4,4-DICYANO-3,3-DIMETHYLBUTANOATE

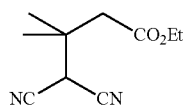

Zinc powder (1.23 g, 18.85 mmol) was added to a THF (20 mL) solution of isopropylidenemalononitrile (1.0 g, 9.42 mmol), ethyl bromoacetate (3.15 g, 18.85 mmol) and titanium bis(cyclopentadienyl)dichloride (235 mg, 0.94 mmol). After stirring for 1 hour the solution was partitioned between ethyl acetate and aqueous 1N HCl. The organic phase was washed with water, brine, dried over MgSO$_4$ and filtered. The solution was concentrated and the crude residue purified by silica gel chromatography using a hexanes/EtOAc gradient to give the indicated product. $^1$H NMR (400 MHz, CD3CN): δ 4.55 (s, 1H); 4.10 (q, J=7.2 Hz, 2H); 2.48 (s, 2H); 1.24 (s, 6H); 1.21 (t, J=7.2 Hz, 3H).

Example 1

4-AMINO-2-[5-CHLORO-3-(3,3,3-TRIFLUORO-PROPYL)-1H-INDAZOL-1-YL]-5,5-DIMETHYL-5,7-DIHYDRO-6H-PYRROLO[2,3-D]PYRIMIDIN-6-ONE

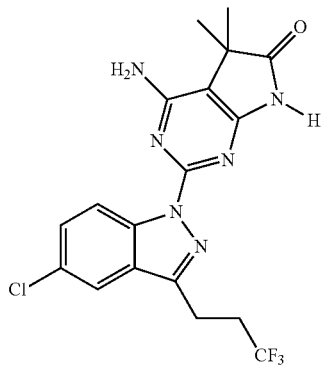 [SMILES: CC1(C)C(=O)Nc2nc(-n3nc(CCC(F)(F)F)c4cc(Cl)ccc43)nc(N)c21]

Step A

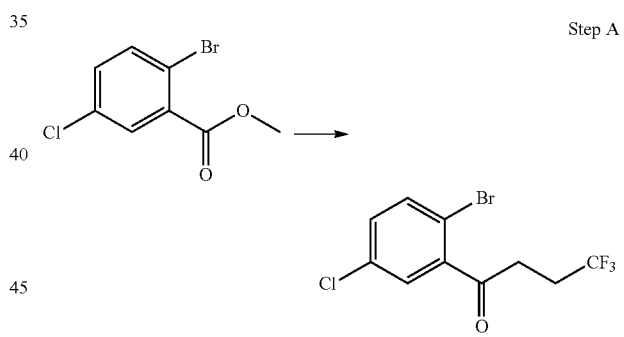

A THF solution of sodium bis(trimethylsilyl)amide (1.0M, 194 mL, 194 mmol) was added dropwise to a −78° C. THF (400 mL) solution containing methyl 2-bromo-5-chlorobenzoate (16.10 g, 64.5 mmol) and 4,4,4-trifluorobutyric acid (9.17 g, 64.5 mmol). After stirring for 15 min at −78° C. the solution was warmed to 0° C. and stirred for an additional 2 hours. The reaction was quenched with an excess of aqueous 1N HCl (ca 400 mL) and stirred overnight at room temperature. The solution was concentrated to remove the majority of the THF. The solution was then diluted with EtOAc and washed with 1N NaHCO$_3$ (twice) and brine. The organic phase was then dried over anhydrous sodium sulfate, filtered and concentrated. The residue was purified by silica gel chromatography using a hexanes/EtOAc gradient to give the indicated compound (solid). $^1$H NMR (500 MHz, CDCl$_3$): δ 7.58 (d, J=8.4 Hz, 1H); 7.41 (d, J=2.5 Hz, 1H); 7.33 (dd, J=8.5, 2.5 Hz, 1H); 3.22 (t, J=7.8 Hz, 2H); 2.68-2.56 (m, 2H). LC4 rt=4.25 min, m/z=not ionized (M+H).

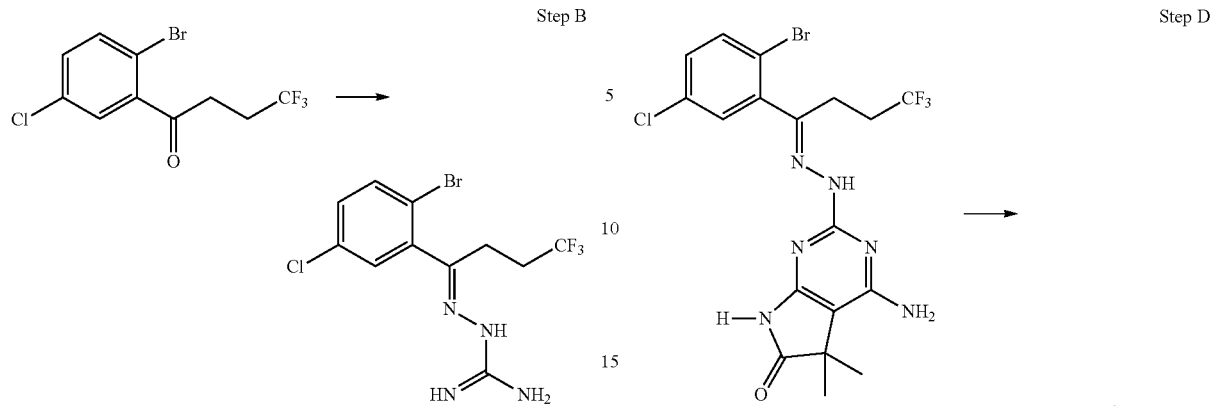

Step B

Step D

To a screw cap pressure vessel was added the intermediate from Step A (3.22 g, 10.2 mmol), aminoguanidine hydrochloride (1.69 g, 15.3 mmol), methanol (25 mL) and boron trifluoride diethyl etherate (2.6 mL, 20.4 mmol). The reaction solution was heated at 100° C. for 70 min. The solution was concentrated and the residue partitioned between EtOAc and aqueous 1N NaOH. The organic phase was washed twice with aqueous 1N NaOH and brine (1×). The organic phase was dried over anhydrous magnesium sulfate, filtered and concentrated to give the indicated compound as a mixture of E,Z hyrazone isomers. $^1$H NMR (400 MHz, CD$_3$CN): δ 7.54 (d, J=8.4 Hz); 7.24-7.17 (m, 1H); 7.10 (d, J=2.59 Hz, 1H); 2.68-2.51 (m, 4H). LC4 rt=2.79 min, m/z=371 (M+H).

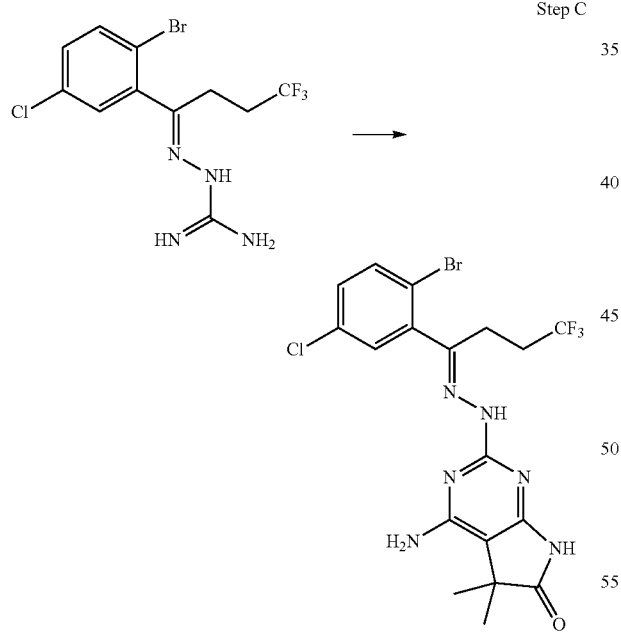

Step C

A screw cap pressure tube containing an n-butanol (90 mL) solution of the intermediate from Step B (6.3 g, 16.95 mmol), the Intermediate 1 (5.63 g, 33.9 mmol) and potassium t-butoxide (2.0 g, 16.95 mmol) was heated at 130° C. for 75 min. The solution was concentrated and the residue partitioned between EtOAc and aqueous 1N NaOH. The organic phase was washed with brine, dried over anhydrous magnesium sulfate, filtered and concentrated. LC4 rt=2.90 min, m/z=505 (M+H).

A DMF (200 mL) solution of the crude intermediate from Step C (8.51 g, 16.8 mmol), copper iodide (0.64 g, 3.37 mmol) and N,N'-dimethylethylenediamine (1.78 g, 20.2 mmol) were stirred at room temperature for 30 min. The reaction mixture was filtered through celite and the filter pad washed several times with small portions of DMF. The filtrate was diluted with EtOAc and washed with water (3×) and brine. The organic phase was concentrated and the residue purified by reverse phase HPLC using a water/acetonitrile (with 0.1% TFA) gradient to give the indicated compound. $^1$H NMR (400 MHz, CD$_3$CN): δ 8.97 (s, 1H); 8.75 (d, J=9.0 Hz, 1H); 7.82 (s, 1H); 7.47 (dd, J=9.0, 1.9 Hz, 1H); 5.60 (s, 2H); 3.27-3.19 (m, 2H); 2.80-2.66 (m, 2H); 1.38 (s, 6H). LC4 rt=3.73 min, m/z=425 (M+H).

Example 2

4-AMINO-5,5-DIMETHYL-2-[3-(3,3,3-TRIFLUOROPROPYL)-1H-INDAZOL-1-YL]-5,7-DIHYDRO-6H-PYRROLO[2,3-D]PYRIMIDIN-6-ONE

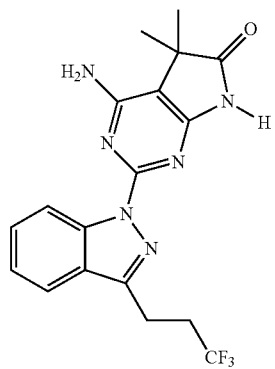 [SMILES: CC1(C)C(=O)Nc2nc(-n3nc(CCC(F)(F)F)c4ccccc43)nc(N)c21]

The compound of Example 1 (9 mg, 0.02 mmol) and palladium hydroxide on carbon (20 wt %, 15 mg) in MeOH (ca 10 mL) were stirred under a hydrogen atmosphere (balloon). After stirring for several hours the solution was filtered through celite and concentrated. The residue was purified by preparative TLC using 5% MeOH/DCM as the eluent to give the indicated compound. $^1$H NMR (500 MHz, DMSO-$d_6$): δ 11.08 (s, 1H); 8.82 (d, J=8.5 Hz, 1H); 7.89 (d, J=8.0 Hz, 1H); 7.53 (t, J=7.8 Hz, 1H); 7.31 (t, J=7.5 Hz, 1H); 6.94 (s, 2H); 3.28-3.21 (m, 2H); 2.89-2.77 (m, 2H); 1.35 (s, 6H). LC4 rt=3.42 min, m/z=391 (M+H).

Example 3

4-AMINO-2-[5-CHLORO-3-(2,3,6-TRIFLUOROBENZYL)-1H-INDAZOL-1-YL]-5,5-DIMETHYL-5,7-DIHYDRO-6H-PYRROLO[2,3-D]PYRIMIDIN-6-ONE

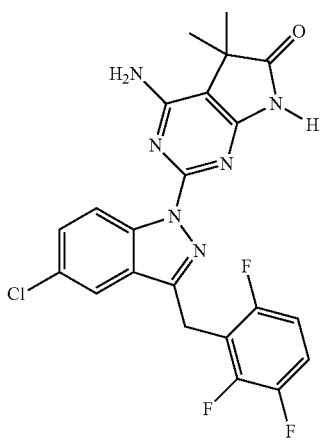 [SMILES: CC1(C)C(=O)Nc2nc(-n3nc(Cc4c(F)ccc(F)c4F)c4cc(Cl)ccc43)nc(N)c21]

To a solution of 2,3,6 trifluorophenyl acetic acid (5 g, 26.3 mmol) and methyl 2-bromo-5-chloro benzoate in anhydrous THF (53 mL) cooled to −78° C. was slowly added NaHMDS (110 mL, 65.7 mmol, 0.6 M). The reaction was then warmed to 0° C. After stirring for 30 minutes the reaction was quenched by adding aqueous 1N HCl (100 mL). The resulting mixture was stirred vigorously at room temperature for 1 hour. The reaction mixture was concentrated to remove the excess organic solvents. The residue was extracted with EtOAc. The organic layer was washed with saturated sodium bicarbonate solution (2×), water and brine. The organic layer was then dried over sodium sulfate, filtered and concentrated to give the indicated product. $^1$H NMR (400 MHz, CD$_3$CN): δ 7.66-7.61 (m, 2H); 7.40 (dd, J=8.6, 2.6 Hz, 1H); 7.25 (m, 1H); 6.98 (m, 1H); 4.34 (s, 2H). LC4 rt=4.41 min, (M+H) not ionized.

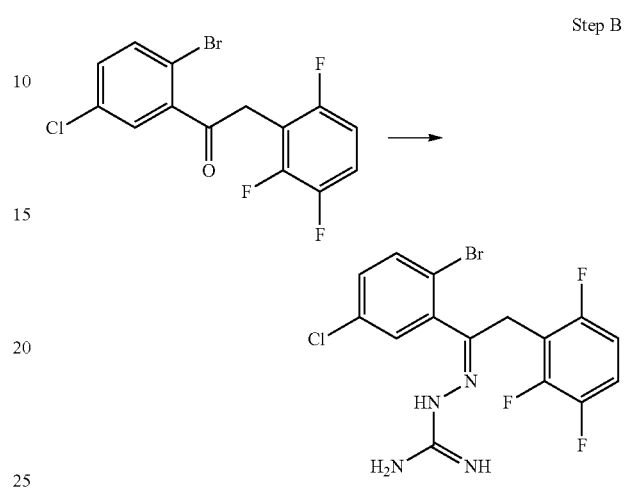

To a screw cap pressure vessel was added the intermediate from Step A (800 mg, 2.20 mmol), aminoguanidine hydrochloride (280 mg, 2.53 mmol), methanol (20 mL) and boron trifluoride diethyl etherate (0.63 mL, 4.95 mmol). After stirring at 100° C. for 1 hour, boron trifluoride diethyl etherate (1 mL) and aminoguanidine hydrochloride (200 mg) were added and the reaction solution heated at 100° C. for 3 hours. The solution was concentrated and the residue partitioned between EtOAc and aqueous 1N NaOH. The organic phase was washed with aqueous 1N NaOH (2×), brine and dried over anhydrous sodium sulfate. The solution was then filtered and concentrated to give the indicated product. LC1 rt=2.69 min, m/z=419 (M+H).

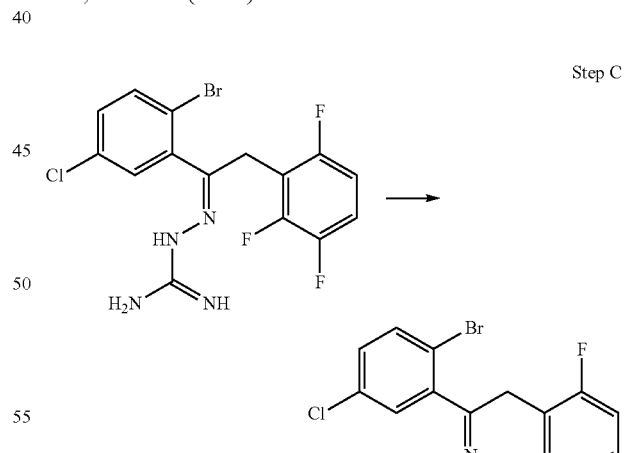

A methanol (3 mL) solution of the intermediate from Step B (100 mg, 0.24 mmol) and Intermediate 1 (120 mg, 0.72 mmol) were heated at 135° C. for 20 min in a microwave. The solution was concentrated to give the indicated compound which was used without purification in the next step. LC1 rt=2.82 min, m/z=553 (M+H).

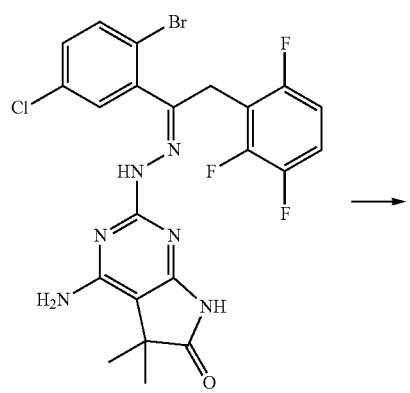

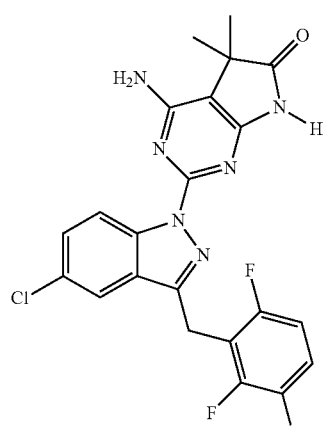

To the crude compound from Step C (ca 0.24 mmol) was added 3 mL NMP and copper iodide (45 mg, 0.24 mmol). The reaction solution was heated at 160° C. for 11 min. The cooled reaction solution was partitioned between DCM and 6% aqueous ammonium hydroxide. The organic phase was washed with brine, dried over anhydrous sodium sulfate, filtered and concentrated. The crude was filtered through a plug of silica gel using 5% MeOH/DCM (with 0.5% aq NH$_4$OH) as the eluent. The material collected was then purified by reverse phase HPLC using a water/acetonitrile gradient (with 0.1% TFA) to give the indicated product. NMR (400 MHz, CH$_3$OH-d): δ 8.78 (d, J=9.1 Hz, 1H); 7.65 (s, 1H); 7.45 (d, J=9.1 Hz, 1H); 7.24-7.18 (m, 1H); 6.97 (t, J=8.3 Hz, 1H); 4.43 (s, 2H); 1.42 (s, 6H). LC1 rt=3.33 min, m/z=473 (M+H).

Example 4

4-AMINO-5,5-DIMETHYL-2-[3-(2,3,6-TRIFLUO-ROBENZYL)-1H-INDAZOL-1-YL]-5,7-DIHY-DRO-6H-PYRROLO[2,3-D]PYRIMIDIN-6-ONE

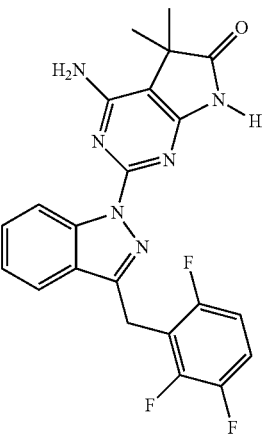 [SMILES: CC1(C)C(=O)Nc2nc(-n3nc(Cc4c(F)ccc(F)c4F)c4ccccc43)nc(N)c21]

The indicated compound was prepared from Example 3 using the hydrogenation procedure described in Example 2. $^1$H NMR (400 MHz, CD$_3$CN): δ 8.81 (s, 1H); 8.75 (d, J=8.6 Hz, 1H); 7.71 (d, J=8.1 Hz, 1H); 7.48 (t, J=7.8 Hz, 1H); 7.29-7.13 (m, 2H); 6.99-6.92 (m, 1H); 5.54 (s, 2H); 4.42 (s, 2H); 1.37 (s, 6H). LC1 rt=3.08 min, m/z=439 (M+H).

Example 5

4-AMINO-2-(5-FLUORO-3-HEXYL-1H-INDA-ZOL-1-YL)-5,5-DIMETHYL-5,7-DIHYDRO-6H-PYRROLO[2,3-D]PYRIMIDIN-6-ONE

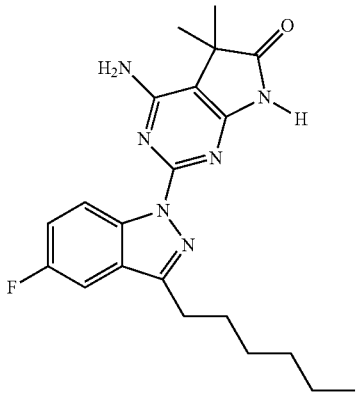 [SMILES: CCCCCCc1nn(-c2nc(N)c3c(n2)NC(=O)C3(C)C)c2ccc(F)cc12]

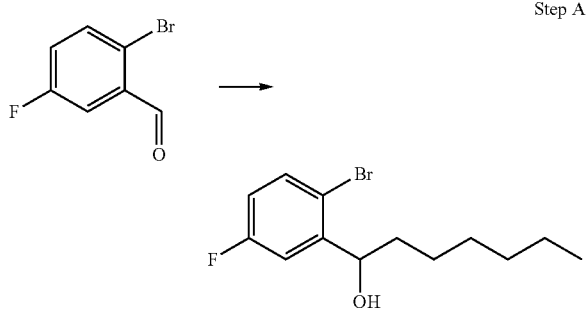

A diethyl ether solution of n-hexylmagnesium bromide (2.0M in diethyl ether, 12.3 mL, 24.6 mmol) was added dropwise to a diethyl ether solution (50 mL) of 2-bromo-5-fluorobenzaldehyde (5 g, 24.63 mmol). After stirring for 30 min at room temperature the solution was partitioned between EtOAc and aqueous 1N HCl. The organic phase was washed with water and brine. The solution was then dried over anhydrous magnesium sulfate, filtered and concentrated. The crude was purified by silica gel chromatography using a hexanes/EtOAc gradient to give the indicated compound. $^1$H NMR (400 MHz, CD$_3$CN): δ 7.50 (dd, J=8.8, 5.3 Hz, 1H); 7.28 (dd, J=10.1, 3.2 Hz, 1H); 6.90 (m, 1H); 4.86 (m, 1H); 3.41 (d, J=4.5 Hz, 1H); 1.73-1.58 (m, 2H); 1.56-1.20 (m, 8H); 0.85 (t, J=6.4 Hz, 3H). LC4 rt=4.62 min, not ionized.

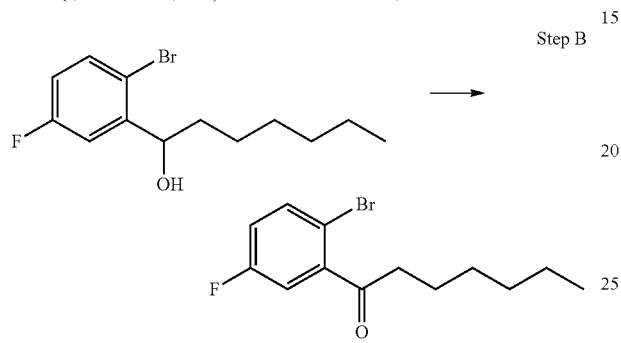

Step B

The product from Step A (ca. 3 g, 10.4 mmol) was dissolved in acetone (50 mL) and chromium trioxide (3.7M in 2/1 water/concentrated sulfuric acid) was added until the color of the chromium oxide solution persisted (ca 3 mL, 10.9 mmol). The excess reagent was quenched with a small amount of isopropyl alcohol. The mixture was filtered and concentrated. The residue was partitioned between EtOAc and water. The organic phase was washed with water and brine. The solution was then dried over anhydrous magnesium sulfate, filtered and concentrated to give the indicated compound. $^1$H NMR (400 MHz, CD$_3$CN): δ 7.62 (dd, J=8.8, 5.0 Hz, 1H); 7.20 (dd, J=8.7, 3.1 Hz, 1H); 7.11 (m, 1H); 2.84 (t, J=7.3 Hz, 2H); 1.66-1.56 (m, 2H); 1.35-1.24 (m, 6H); 0.86 (t, J=6.6 Hz, 3H). LC4 rt=4.69 min, (M+H) not ionized.

Step C

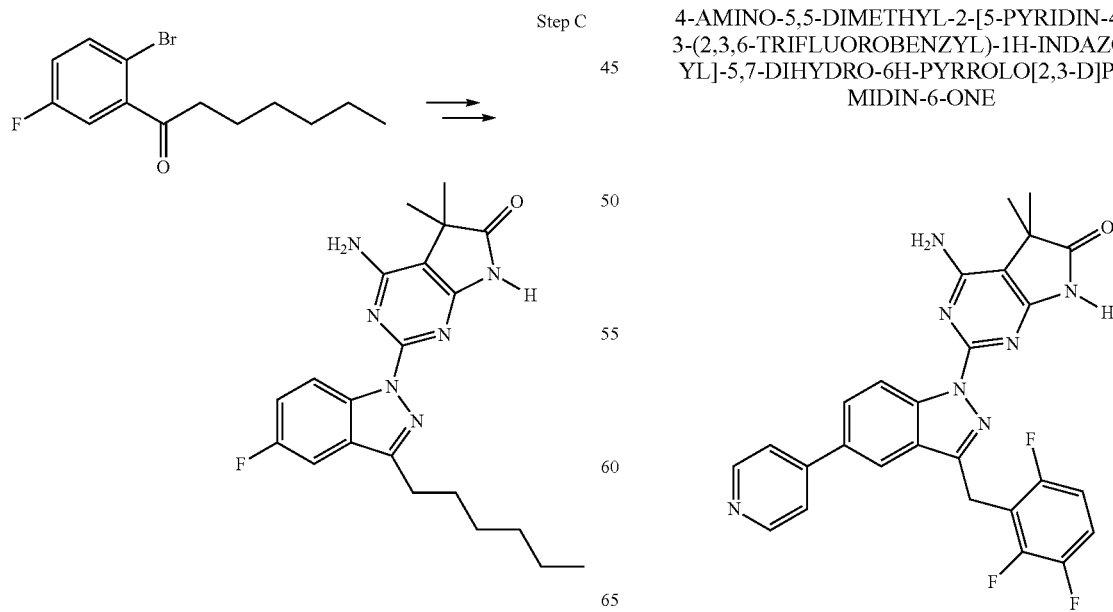

The indicated product was prepared from the intermediate from Step B as described in Example 1. $^1$H NMR (500 MHz, DMSO-d$_6$): δ 11.13 (s, 1H); 8.85 (dd, J=9.2, 4.6 Hz, 1H); 7.66 (dd, J=8.6, 2.6 Hz, 1H); 7.37 (m, 1H); 7.01 (s, 2H); 3.35-3.31 (m, 2H); 2.94 (t, J=7.5 Hz, 2H); 1.76-1.68 (m, 2H); 1.5 (s, 6H); 1.31-1.21 (m, 4H); 0.84 (t, J=6.8 Hz, 3H). LC4 rt=4.07 min, m/z 397 (M+H).

Example 6

4-AMINO-2-[5-BROMO-3-(2,3,6-TRIFLUO-ROBENZYL)-1H-INDAZOL-1-YL]-5,5-DIMETHYL-5,7-DIHYDRO-6H-PYRROLO [2,3-D] PYRIMIDIN-6-ONE

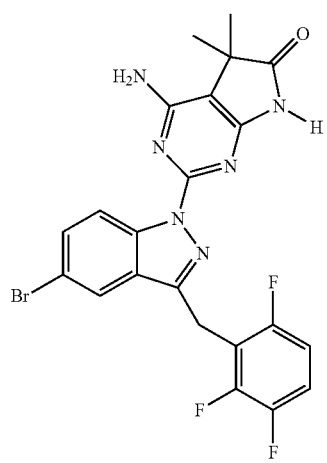 [SMILES: CC1(C)C(=O)Nc2nc(-n3nc(Cc4c(F)ccc(F)c4F)c4cc(Br)ccc43)nc(N)c21]

The title product was prepared from methyl 2,5-dibromobenzoate and 2,3,6 trifluorophenyl acetic acid as described in Example 3. $^1$H NMR (500 MHz, DMSO-d$_6$): δ 11.06 (broad s, 1H); 8.76 (d, J=8.9 Hz, 1H); 8.07 (s, 1H); 7.64 (dd, J=8.9, 2.0 Hz, 1H); 7.52-7.44 (m, 1H); 7.21-7.16 (m, 1H); 6.96 (s, 2H); 4.45 (s, 2H); 1.32 (s, 6H). LC4 rt=4.00 min, m/z=518 (M+H).

Example 7

4-AMINO-5,5-DIMETHYL-2-[5-PYRIDIN-4-YL-3-(2,3,6-TRIFLUOROBENZYL)-1H-INDAZOL-1-YL]-5,7-DIHYDRO-6H-PYRROLO[2,3-D]PYRIMIDIN-6-ONE

A 1,4-dioxane/DMF (5 mL, 1/1) solution containing Example 6 (50 mg, 0.097 mmol), 4-pyridineboronic acid (59 mg, 0.48 mmol), 1,1'-bis(di t-butylphosphino)ferrocene palladium dichloride (5 mg, 0.0077 mmol), aqueous potassium carbonate (1N, 0.48 mL, 0.48 mmol) was heated at 100° C. for 30 min. The crude reaction was purified by reverse phase HPLC using a water/acetonitrile gradient. The isolated material was further purified by TLC using 9/1/0.05 DCM/MeOH/NH₄OH aq eluent to give the titled product. ¹H NMR (500 MHz, DMSO-de): δ 11.09 (s, 1H); 8.90 (d, J=8.8 Hz, 1H); 8.68 (d, J=5.0 Hz, 2H); 8.31 (s, 1H); 7.95 (d, J=8.8 Hz, 1H); 7.80 (d, J=5.1 Hz, 2H); 7.50-7.43 (m, 1H); 7.24-7.16 (m, 1H); 6.98 (s, 2H); 4.54 (s, 2H); 1.34 (s, 6H). LC5 rt=1.63 min, m/z=516 (M+H).

Example 8

4-AMINO-5,5-DIMETHYL-2-[3-(4,4,4-TRIFLUO-ROBUTYL)-1H-THIENO[3,4-C]PYRAZOL-1-YL]-5,7-DIHYDRO-6H-PYRROLO[2,3-D]PYRIMIDIN-6-ONE

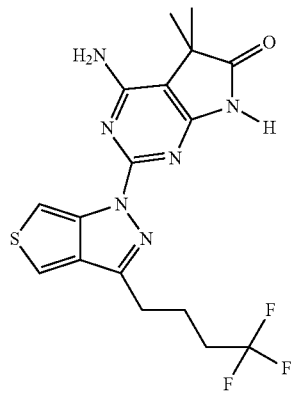 [SMILES: CC1(C)C(=O)Nc2nc(-n3nc(CCCC(F)(F)F)c4cscc43)nc(N)c21]

The titled compound was prepared from 3-bromo-4-formylthiophene and 1-iodo-4,4,4-trifluorobutane following the procedure described in Example 5. ¹H NMR (400 MHz, CD₃CN): δ 8.68 (s, 1H); 7.56 (d, J=2.8 Hz, 1H); 7.48 (d, J=2.8 Hz, 1H); 5.46 (s, 2H); 2.92 (t, J=7.5 Hz, 2H); 2.33-2.19 (m, 2H); 1.76-1.72 (m, 2H); 1.36 (s, 6H). LC4 rt=3.34 min, m/z 411 (M+H).

Example 9

4-AMINO-5,5-DIMETHYL-2-[3-(2,3,6-TRIFLUO-ROBENZYL)-1H-THIENO[3,4-C]PYRAZOL-1-YL]-5,7-DIHYDRO-6H-PYRROLO[2,3,0]PYRIMI-DIN-6-ONE

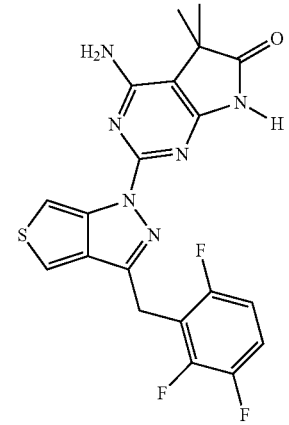 [SMILES: CC1(C)C(=O)Nc2nc(-n3nc(Cc4c(F)ccc(F)c4F)c4cscc43)nc(N)c21]

The titled compound was prepared from methyl 4-bromothiophene-3-carboxylate and 2,3,6 trifluorophenyl acetic acid following the procedure described in Example 1. ¹H NMR (400 MHz, CD₃CN): δ 8.95 (s, 1H); 7.56 (d, J=2.8 Hz, 1H); 7.26-7.16 (m, 2H); 7.02-6.93 (m, 1H); 5.49 (s, 2H); 4.27 (s, 2H); 1.36 (s, 6H). LC4 rt=3.46 min, m/z=445 (M+H)

Example 10

4-AMINO-5,5-DIMETHYL-2-[3-(2,3,6-TRIFLUO-ROBENZYL)-4,6-DIHYDRO-1H-THIENO[3,4-C]PYRAZOL-1-YL]-5,7-DIHYDRO-6H-PYRROLO[2,3-D]PYRIMIDIN-6-ONE

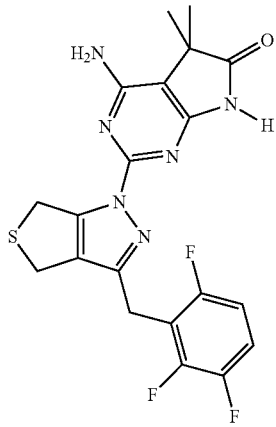 [SMILES: CC1(C)C(=O)Nc2nc(-n3nc(Cc4c(F)ccc(F)c4F)c4c3CSC4)nc(N)c21]

A 1,2-dichloroethane (1 mL) solution containing Example 9 (15 mg, 0.034 mmol), triethylsilane (0.7 mL, 4.38 mmol) and TFA (0.3 mL, 4.04 mmol) was heated in a screw cap pressure tube at 75° C. for 3 hours. The solution was concentrated and the residue partitioned between EtOAc and aqueous 1N NaOH. The organic phase was washed with brine and dried over MgSO₄. The solution was filtered and concentrated. The residue was purified by reverse phase HPLC to give the titled product. ¹H NMR (400 MHz, CD₃CN): δ 8.73 (s, 1H); 7.24-7.11 (m, 1H); 6.99-6.91 (m, 1H); 5.46 (s, 2H); 4.31 (t, J=3.0 Hz, 2H); 3.98 (s, 2H); 3.61 (t, J=3.0 Hz, 2H); 1.33 (s, 6H). LC4 rt=3.57 min, m/z=447 (M+H)

Example 11

4-AMINO-2-[3-(2-CYCLOPENTYLETHYL)-1H-INDAZOL-1-YL]-5,5-DIMETHYL-5,7-DIHYDRO-6H-PYRROLO[2,3-D]PYRIMIDIN-6-ONE

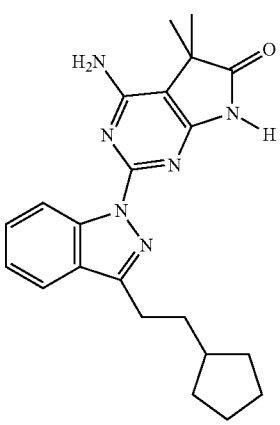 [SMILES: CC1(C)C(=O)Nc2nc(-n3nc(CCC4CCCC4)c4ccccc43)nc(N)c21]

Step A

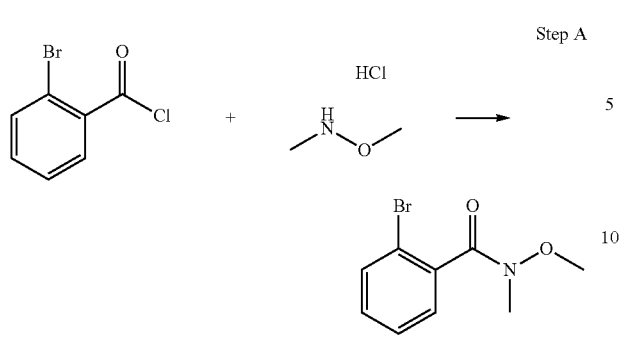

To a solution of 2-bromo benzoyl chloride (7.92 mL, 60.6 mmol) and DIEA (21.17 mL, 121 mmol) in DCM (121 mL) was added a solution of N,O-dimethyl hydroxylamine hydrochloride (5.91 g, 60.6 mmol) in DCM (121 mL). After 30 minutes, the reaction was diluted with ethyl acetate, washed with brine, dried over sodium sulfate, filtered and concentrated in vacuo. The residue was purified by flash chromatography using a gradient of 0-100% ethyl acetate/hexanes.

Step B

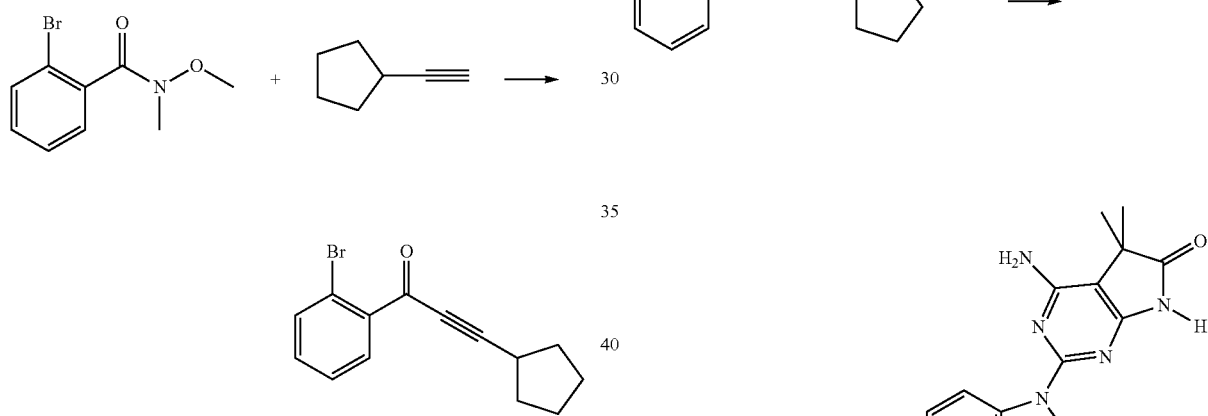

To a solution of cyclopentyl acetylene (700 mg, 7.43 mmol) and Weinreb amide from step A (1815 mg, 7.43 mmol) cooled to −78° C. was added LiHMDS (7.43 mL, 7.43 mmol). After 15 min, the ice bath was removed and the reaction was warmed to room temperature. The reaction mixture was quenched by adding saturated ammonium chloride solution. The resulting mixture was extracted with ethyl acetate, washed with brine, dried over sodium sulfate, filtered and concentrated in vacuo. The residue was purified by flash chromatography Biotage SP 1 using a gradient of 0-100% ethyl acetate/hexanes to give the indicated compound.

Step C

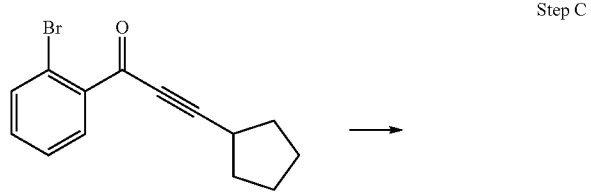

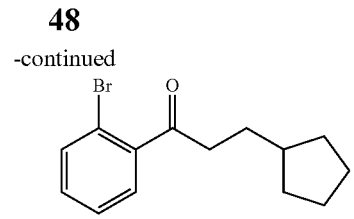

To a solution of the intermediate from step B (300 mg, 1.08 mmol) in ethyl acetate (20 mL) was added platinum (IV) oxide (25 mg, 0.108 mmol). The resulting reaction mixture was stirred under hydrogen balloon for 24 hours. The reaction was filtered through celite. The filtrate was concentrated in vacuo. $^1$H NMR (CDCl$_3$, 500 MHz) δ 7.62 (d, 1H), 7.38 (d, 2H), 7.30 (m, 1H), 2.95 (t, 2H), 1.85-1.72 (m, 5H), 1.67-1.53 (m, 4H), 1.15 (m, 2H).

Step D

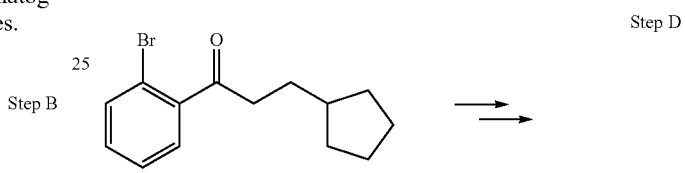

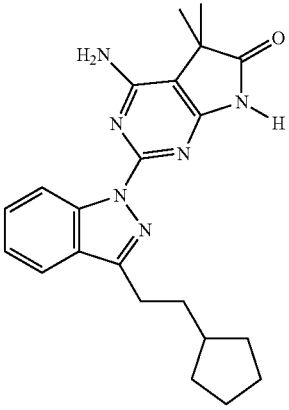

The indicated product was prepared from the intermediate from Step C as described in Example 1. $^1$H NMR (500 MHz, DMSO-d$_6$): δ 8.80 (d, J=8.53 Hz, 1H); 7.80 (d, J=7.87 Hz, 1H); 7.49 (t, J=7.83 Hz, 1H); 7.28 (t, J=7.39 Hz, 1H); 6.91 (s, 2H); 2.96 (t, J=7.47 Hz, 2H); 1.84-1.74 (m, 5H); 1.61-1.53 (m, 3H); 1.52-1.42 (m, 1H); 1.34 (s, 6H); 1.19-1.09 (m, 2H). LC2 rt=1.22 min, m/z 391 (M+H)

Using essentially the same procedures described in Examples 1 to 11, the following compounds in Table 1 and Table 2 were made.

TABLE 1
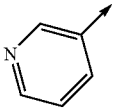
| EXAMPLE | R¹ | R² | LC-MS data | Method |
|---|---|---|---|---|
| 12 | H | 2-F—Ph | 2.19 min (M + H) 403 | LC3 |
| 13 | Cl | 2-F—Ph | 2.43 min (M + H) 437 | LC3 |
| 14 | F | 2-F—Ph | 2.28 min (M + H) 421 | LC3 |
| 15 | Cl | 2,3-di F—Ph | 3.42 min (M + H) 455 | LC1 |
| 16 | F | 2,3-di F—Ph | 2.36 min (M + H) 439 | LC5 |
| 17 | H | 2,3-di F—Ph | 3.12 min (M + H) 421 | LC1 |
| 18 | Ph | 2-F—Ph | 3.55 min (M + H) 479 | LC1 |
| 19 | F | 2,3,6-tri F—Ph | 2.34 min (M + H) 458 | LC5 |
| 20 | 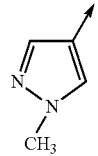 | 2,3,6-tri F—Ph | 1.64 min (M + H) 516 | LC5 |
| 21 | 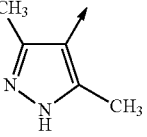 | 2,3,6-tri F—Ph | 2.12 min (M + H) 520 | LC5 |
| 22 | 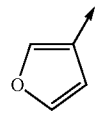 | 2,3,6-tri F—Ph | 1.78 min (M + H) 534 | LC5 |
| 23 | 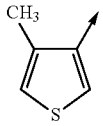 | 2,3,6-tri F—Ph | 2.45 min (M + H) 505 | LC5 |
| 24 |  | 2,3,6-tri F—Ph | 2.61 min (M + H) 535 | LC5 |
| 25 | 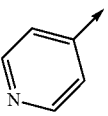 | 2,3,6-tri F—Ph | 2.42 min (M + H) 479 | LC5 |
| 26 | 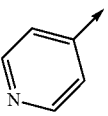 | 2,3,6-tri F—Ph | 1.64 min (M + H) 517 | LC5 |
| 27 | Ph | 2,3,6-tri F—Ph | 2.60 min (M + H) 515 | LC5 |

TABLE 1-continued

| EXAMPLE | R¹ | R² | LC-MS data | Method |
|---|---|---|---|---|
| 28 | Cl | pyrimidin-5-yl | 3.01 min (M + H) 421 | LC4 |
| 29 | thiophen-3-yl | 2,3,6-tri F—Ph | 4.00 min (M + H) 521 | LC4 |
| 30 | 5-F-pyridin-3-yl | 2,3,6-tri F—Ph | 3.64 min (M + H) 534 | LC4 |
| 31 | 6-F-pyridin-3-yl | 2,3,6-tri F—Ph | 3.8 min (M + H) 534 | LC4 |
| 32 | 5-CF₃-pyridin-3-yl | 2,3,6-tri F—Ph | 3.99 min (M + H) 584 | LC4 |
| 33 | Cl | 2,3-di F, 6-Br—Ph | 4.12 mi. (M + H) 535 | LC4 |
| 34 | H | cyclopentylmethyl | 1.22 min (M + H) 391 | LC2 |
| 35 | F | $(CH_2)_3CH_3$ | 3.84 min (M + H) 383 | LC4 |
| 36 | F | $CH_2CF_3$ | 3.53 min (M + H) 409 | LC4 |
| 37 | F | cyclopentylmethyl | 1.21 min (M + H) 409 | LC2 |
| 38 | Cl | cyclopentylmethyl | 1.24 min (M + H) 425 | LC2 |
| 39 | F | $(CH_2)_2CF_3$ | 2.06 min (M + H) 423 | LC3 |
| 40 | Cl | $(CH_2)_3CH_3$ | 2.09 min (M + H) 399 | LC3 |
| 41 | Cl | $(CH_2)_2CH_3$ | 3.95 min (M + H) 385 | LC4 |
| 42 | Cl | $(CH_2)_2CF_3$ | 3.81 min (M + H) 439 | LC4 |
| 43 | Cl | $(CH_2)_2CHCH_2$ | 3.89 min (M + H) 397 | LC4 |
| 44 | Cl | $CH_2CHCH_2$ | 2.10 min (M + H) 383 | LC3 |
| 45 | Cl | $CH_2CH_3$ | 3.68 min (M + H) 371 | LC4 |
| 46 | Cl | $CH_2CO_2Et$ | 3.49 min (M + H) 429 | LC4 |

TABLE 1-continued
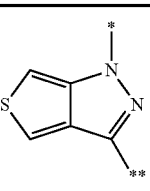
| EXAMPLE | R¹ | R² | LC-MS data | Method |
|---|---|---|---|---|
| 47 | Cl | $CH_2C(CH_3)_3$ | 4.29 (M + H) 413 | LC4 |
TABLE 2
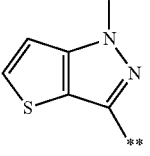
| EXAMPLE | X | Z | LC-MS data | Method |
|---|---|---|---|---|
| 48 | 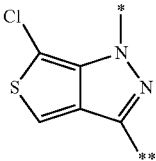 | H | 3.47 min (M + H) 427 | LC4 |
| 49 | 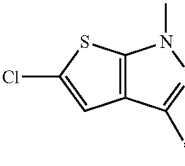 | H | 3.66 min (M + H) 461 | LC4 |
| 50 | 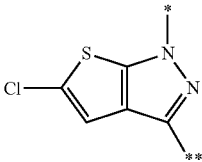 | H | 4.08 min (M + H) 461 | LC4 |
TABLE 2-continued
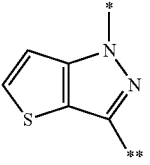
| EXAMPLE | X | Z | LC-MS data | Method |
|---|---|---|---|---|
| 51 |  | H | 3.63 min (M + H) 427 | LC4 |
| 52 |  | F | 3.97 min (M + H) 479 | LC4 |
| 53 |  | F | 3.62 min (M + H) 445 | LC4 |

TABLE 2-continued

| EXAMPLE | X | Z | LC-MS data | Method |
|---|---|---|---|---|
| 54 | (1-methylpyrazolo[3,4-c]pyrazole) | F | 1.89 min (M + H) 443 | LC5 |
| 55 | (thieno[2,3-c]pyrazole) | F | 3.67 min (M + H) 445 | LC4 |
| 56 | (1,5-dimethylpyrazolo[3,4-c]pyrazole) | F | 3.21 min (M + H) 443 | LC4 |
| 57 | (pyrazolo[4,3-c]pyridine) | F | 1.46 min (M + H) 440 | LC5 |

Example 58

4-AMINO-5,5-DIMETHYL-2-[7-(2,3,6-TRIFLUO-ROBENZYL)IMIDAZO[1,5-B]PYRIDAZIN-5-YL]-5,7-DIHYDRO-6H-PYRROLO[2,3-D]PYRI-MIDIN-6-ONE

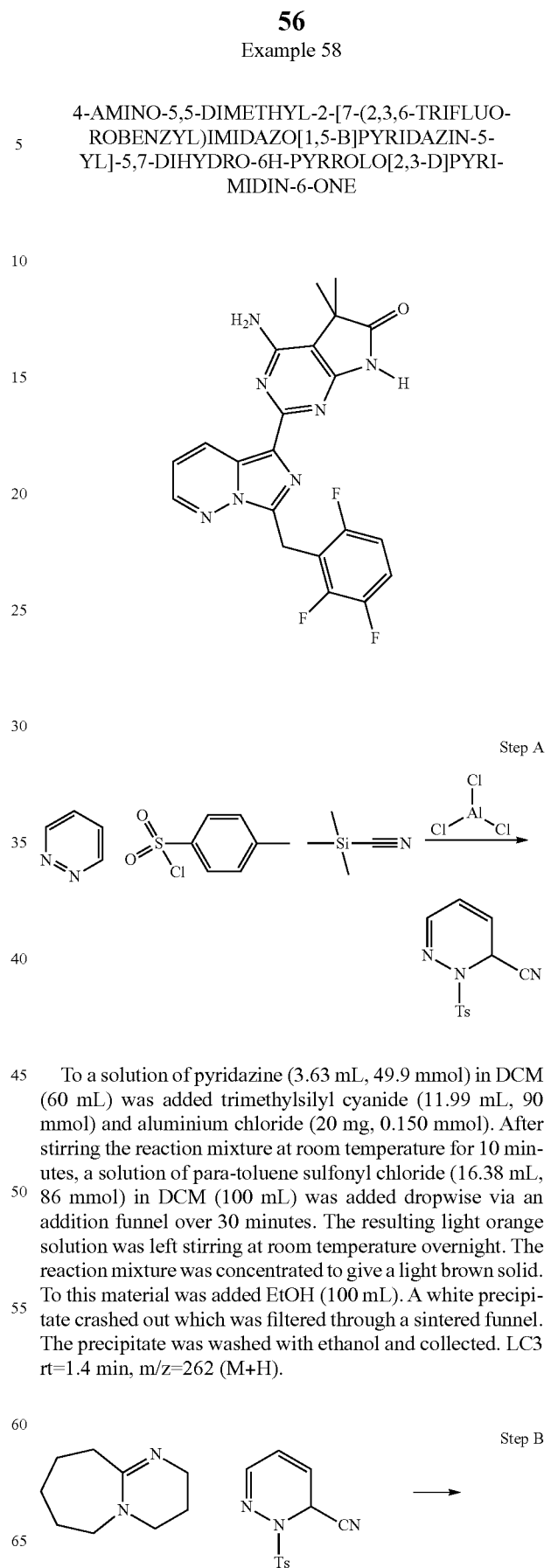

Step A

To a solution of pyridazine (3.63 mL, 49.9 mmol) in DCM (60 mL) was added trimethylsilyl cyanide (11.99 mL, 90 mmol) and aluminium chloride (20 mg, 0.150 mmol). After stirring the reaction mixture at room temperature for 10 minutes, a solution of para-toluene sulfonyl chloride (16.38 mL, 86 mmol) in DCM (100 mL) was added dropwise via an addition funnel over 30 minutes. The resulting light orange solution was left stirring at room temperature overnight. The reaction mixture was concentrated to give a light brown solid. To this material was added EtOH (100 mL). A white precipitate crashed out which was filtered through a sintered funnel. The precipitate was washed with ethanol and collected. LC3 rt=1.4 min, m/z=262 (M+H).

Step B

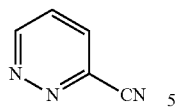

To a solution of the intermediate from Step A (10 g, 38.3 mmol) in anhydrous THF (90 mL) was added DBU (7.21 mL, 47.8 mmol). The resulting solution was stirred at room temperature for 30 minutes. The reaction was quenched by the addition of saturated ammonium chloride solution (40 mL). The resulting mixture diluted with water (30 mL) and extracted with ethyl acetate several times (until aqueous layer had no product). The organic layer was washed with brine, dried over anhydrous sodium sulfate, filtered and concentrated. The residue was purified by silica gel chromatography using a ethyl acetate hexanes gradient to afford a white solid. $^1$H NMR (500 MHz, CDCl$_3$) δ 9.4 (m, 2H), 7.9 (m, 2H), 7.7 (m, 1H). LC1 rt=0.11 min, m/z=106 (M+H).

Step C

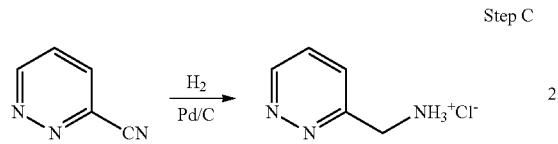

To a solution of the intermediate from Step B (5.96 g, 56.7 mmol) in MeOH (35 mL) was added 6N HCl (20.89 mL, 125 mmol) followed by Pd/C (0.905 g, 8.51 mmol). The reaction mixture was kept on Parr shaker for 2 hours at 40 psi hydrogen. The reaction mixture was filtered through celite and washed with 600 mL of MeOH and the filtrate concentrated. The residue was azeotroped several times with toluene. A dark brown solid was obtained. LC1 rt=0.36 min, m/z=110 (M+H).

washed with brine, dried over anhydrous sodium sulfate, filtered and concentrated to give a brown solid. LC3 rt=0.6 min, m/z=282 (M+H).

Step E

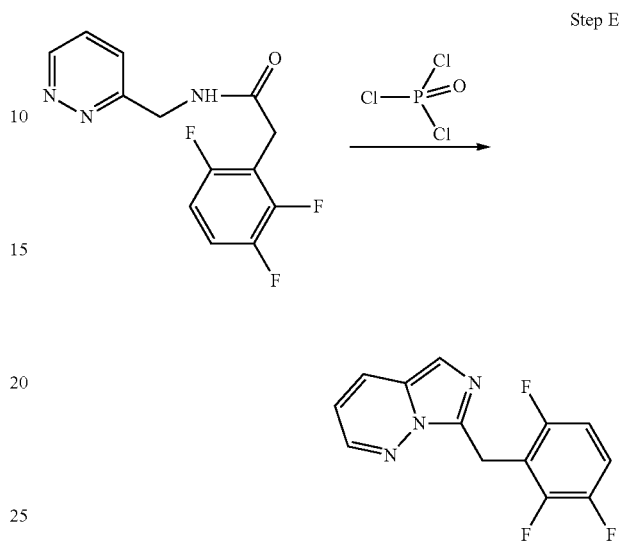

To a solution of the intermediate from Step D (2.6 g, 9.2 mmol) in 1,2-dichloroethane (25 mL) was added POCl$_3$ (5 mL, 53 mmol). The resulting mixture was refluxed for 3 hours. The reaction mixture was cooled to room temperature and concentrated. The residue was partitioned between water and ethyl acetate. The aqueous layer was neutralized with solid sodium bicarbonate and then extracted with ethyl acetate (3×). The organic layer was washed with brine, dried over anhydrous sodium sulfate, filtered and concentrated. The Step D

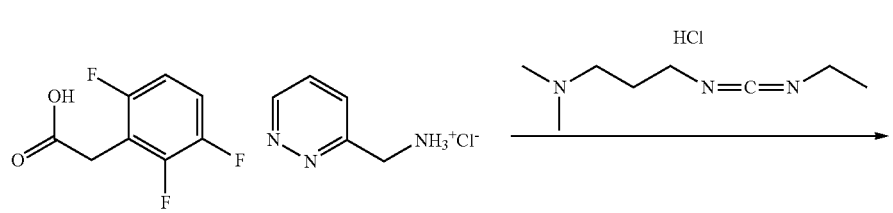

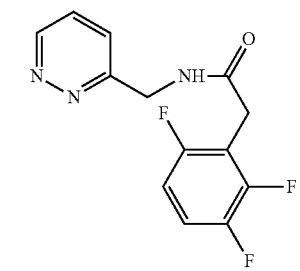

To a solution of 2,3,6-trifluorophenyl acetic acid (5.5 g, 29 mmol) and the intermediate from Step C (5.0 g, 34 mmol) in DCM (20 mL) was added EDC (7.9 g, 41.2 mmol) followed by DIEA (17.99 mL, 103 mmol). After stirring the reaction at room temperature for 18 hours, it was diluted with DCM (100 mL), and washed with water (2×). The organic layer was residue was purified by flash chromatography on Biotage SP1 using a gradient of 10-100% ethyl acetate-hexanes to give a yellow solid. $^1$H NMR δ (ppm) (DMSO-d$_6$): 8.31 (1H, dd, J=4.3, 1.7 Hz), 8.09 (1H, dd, J=9.2, 1.6 Hz), 7.49-7.36 (2H, m), 7.17-7.10 (1H, m), 6.72 (1H, dd, J=9.2, 4.2 Hz), 4.45 (2H, s). LC3 rt=0.4 min, m/z=264 (M+H).

Step F

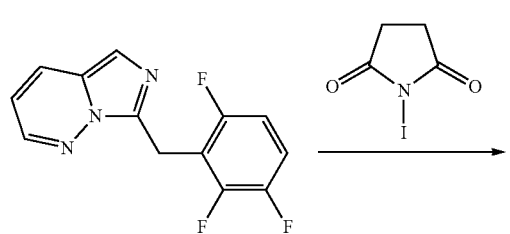

To a solution of the intermediate from Step E (1.7 g, 6.46 mmol) in anhydrous acetonitrile (25 mL) was added a NIS (1.85 g, 8.22 mmol). The reaction mixture was heated at reflux for 20 minutes. The reaction mixture was cooled to room temperature and concentrated. The residue was suspended in ethyl acetate and washed with saturated sodium bicarbonate solution (2×) and saturated sodium thiosulfate (2×). The organic layer was washed with brine, dried over anhydrous sodium sulfate, filtered and concentrated. The residue was purified by flash chromatography on Biotage SP1 using a gradient of 5-50% ethyl acetate-hexanes to give a bright yellow solid. $^1$H NMR δ (ppm) (DMSO-$d_6$): 8.39-8.33 (1H, m), 7.81 (1H, d, J=9.3 Hz), 7.49-7.40 (1H, m), 7.15 (1H, s), 6.83-6.77 (1H, m), 4.48 (s, 2H). LC3 rt=1.87 min, m/z=390 (M+H).

Step G

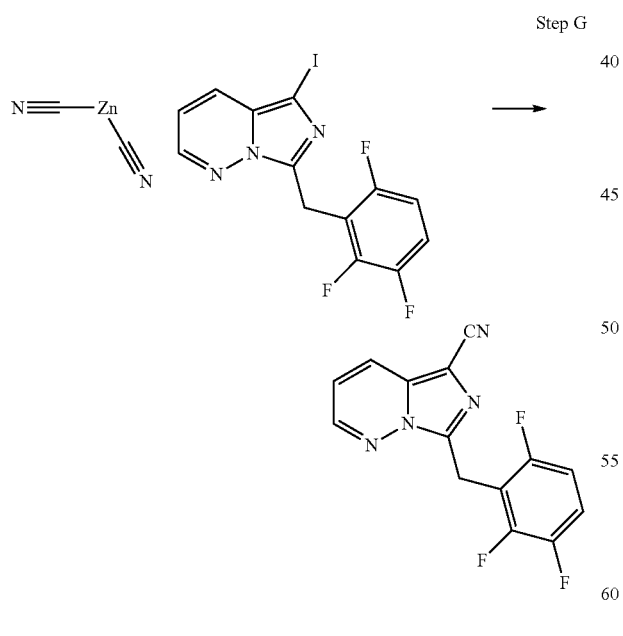

To a solution of the intermediate from Step F (1.5 g, 4.25 mmol) in DMF (5 mL) was added zinc cyanide (0.162 mL, 2.55 mmol), Pd$_2$dba$_3$ (0.078 g, 0.085 mmol), DPPF (0.141 g, 0.255 mmol) and water (0.5 mL). The resulting solution was heated at 110° C. for 1 hour. The reaction was cooled to room temperature, diluted with 15% NH$_4$OH solution (10 mL) and extracted with ethyl acetate. The organic layer was washed with brine, dried over anhydrous sodium sulfate, filtered and concentrated. The residue was purified on a Biotage SP1 using a gradient of 10-100% ethyl acetate-hexanes to give a light yellow solid. $^1$H NMR δ (ppm) (DMSO-$d_6$): 8.64 (1H, dd, J=4.4, 1.6 Hz), 8.40 (1H, dd, J=9.3, 1.5 Hz), 7.52-7.43 (1H, m), 7.25-7.14 (2H, m), 4.52 (2H, s). LC2 rt=1.08 min, m/z=289 (M+H).

Step H

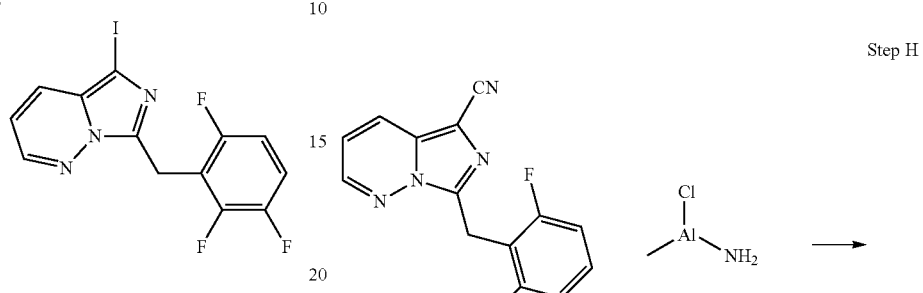

Trimethylaluminum (2.0M toluene, 10 mL, 20 mmol) was added to ammonium chloride (1.07 g, 20 mmol) suspended in toluene (30 mL) at 0° C. The solution was then stirred at room temperature for 2 hours to give a 0.5M amino(chloro)methylaluminum solution in toluene. To the intermediate from Step G (2 g, 7.93 mmol) in toluene (1 mL) was added amino(chloro)methylaluminum (16 mL of 0.5 M solution in toluene, 8 mmol). The resulting mixture was left stirring at 110° C. for 3 hours. The reaction mixture was cooled to room temperature and quenched with silica-gel and 1:1 methanol-chloroform (50 mL). The resulting slurry was stirred vigorously for 30 minutes. The reaction mixture was filtered through a silica gel pad (1″) and washed with methanol. The filtrate was concentrated to yield a light yellow solid. LC2 rt=0.22 min, m/z=306 (M+H).

Step I

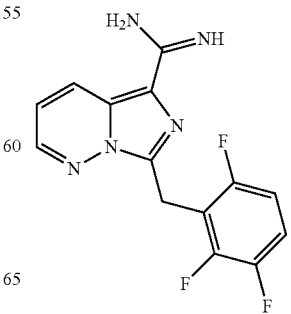

-continued

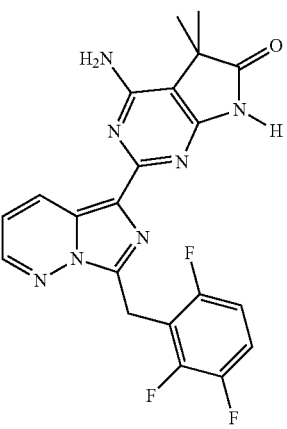

A methanol (1 mL) solution containing the intermediate from Step H (10 mg, 0.033 mmol), Intermediate 1 (16.33 mg, 0.098 mmol) and sodium methoxide (2.65 mg, 0.049 mmol) was heated for 20 minutes in a microwave at 140° C. The reaction was then purified by reverse phase HPLC to give the titled product. $^1$H NMR (500 MHz, DMSO-$d_6$): δ 10.83 (s, 1H); 9.00-8.96 (m, 1H); 8.45-8.43 (m, 1H); 7.53-7.42 (m, 1H); 7.21-7.13 (m, 1H); 6.99-6.95 (m, 1H); 6.63 (s, 2H); 4.51 (s, 2H); 1.30 (s, 6H). LC2 rt=1.06 min, m/z=440 (M+H)

Example 59

4-AMINO-2-[6-CHLORO-3-(2,3,6-TRIFLUO-ROBENZYL)IMIDAZO[1,5-A]PYRIDIN-1-YL]-5,5-DIMETHYL-5,7-DIHYDRO-6H-PYRROLO[2,3-D]PYRIMIDIN-6-ONE

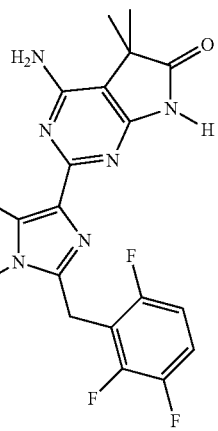

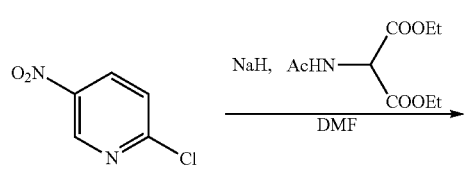

-continued

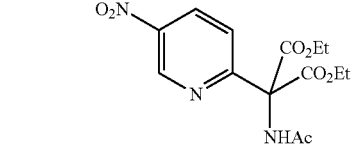

To a stirred slurry of sodium hydride (50% oil dispersion 46 g, 1 mol) in dimethylformamide (500 mL distilled from calcium oxide CaO) was slowly added a solution of diethyl acetamidomalonate (217 g, 1 mol) in dimethylformamide (1200 mL). After the initial reaction, the slurry was heated to 45° C. for 1.5 hours and then 2-chloro-5-nitropyridine (159 g, 1 mol) in DMF (800 mL) was added. The mixture became dark brown during addition of the 2-chloro-5-nitropyridine. The mixture was stirred at 45° C. overnight. After cooling, the mixture was diluted with 1000 mL (0.2N) hydrochloric acid, and then extracted with dichloromethane (3×1200 mL). The combined organic phases were dried over anhydrous magnesium sulfate, filtered and the solvent evaporated to give a dark brown oil. The oil was dry-loaded (on 300 g silica gel) and chromatographed on a dry-packed silica gel column. The column was eluted with petroleum-ethyl acetate (8:1 and then 5:1). Fractions containing the indicated compound were combined and concentrated to give pale yellow solid. Mp 82-83° C.

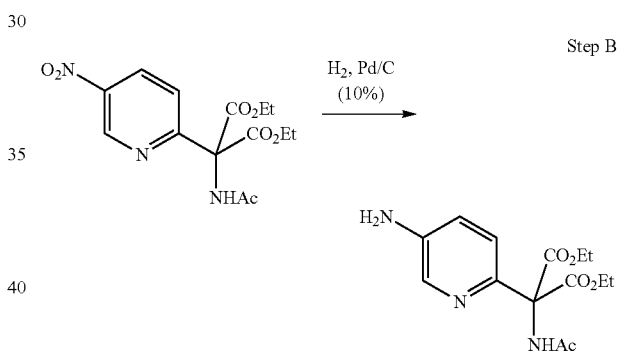

Step B

A mixture of the intermediate from Step A (115 g, 0.33 mol) and 2.5 g Pd/C catalyst (10%) in 200 mL of methanol was hydrogenated at 60 psi overnight. The mixture was filtered through celite, and the filtrate was concentrated to give diethyl (5-amino-2-pyridyl)acetamidomalonate as an off-white solid. Mp: 154-155° C.

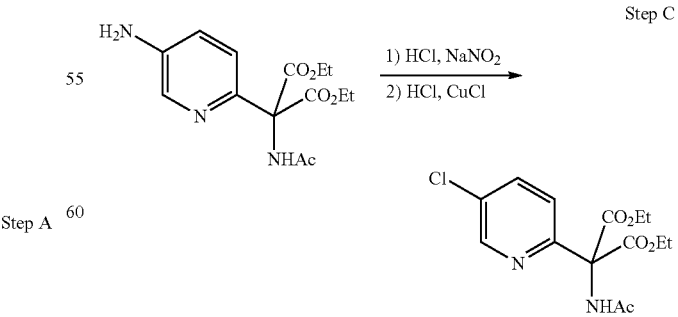

Step C

A solution of 55 g (0.17 mol) of diethyl (5-amino-2-pyridyl)acetamidomalonate (Step B) in 200 mL of 3.5 N hydrochloric acid was cooled to −10° C., and then treated dropwise with a solution of 12.2 g (0.17 mol) of sodium nitrite in 50 mL of water. When the addition was complete, the reaction mixture was stirred below 5° C. for 2 hour, and then added to a solution of cupric chloride (69 g, 0.51 mol) in 200 mL of concentrated hydrochloric acid. The mixture was stirred at ambient temperature for 2 hr, and then diluted with 300 mL of dichloromethane. The organic phases was separated, dried over MgSO₄ and filtered. The solvent was evaporated to afford a dark green solid. The crude product was purified by silica gel column chromatography (ethyl acetate/petrol ether=1:5) to give the indicated compound as a pale yellow solid. Mp: 89-90° C.

Step D

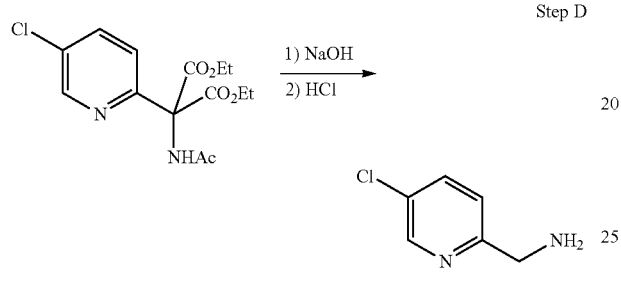

Diethyl (5-chloro-2-pyridyl)acetamidomalonate (70 g, 0.21 mol) was dissolved in 95% ethanol (200 mL). To the stirred solution (2° C.) was added sodium hydroxide solution (105 mL, 8 N). After 2 h, the mixture was cooled to 5° C. and acidified to pH 2 with hydrochloric acid (6 N, ~40 mL). The ethanol was evaporated in vacuum to give a mixture containing some solid. The mixture was mixed with hydrochloric acid (5 N, 150 mL) and heated to 80° C. for 4 hr, and then maintained at room temperature overnight. Sodium hydroxide solution (4 N) was slowly added to the mixture to adjust pH 10. The mixture was extracted with DCM (4×200 mL), and then the combined organic phases were dried over anhydrous Na₂SO₄ and filtered. The solvent was evaporated to give the indicated product as a pale yellow oil.

Step E

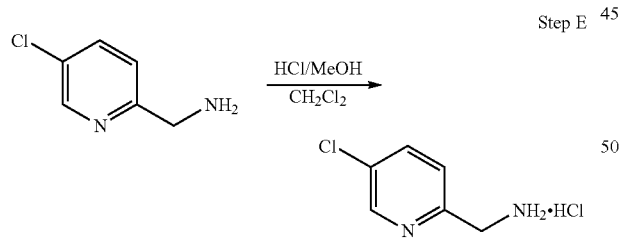

The compound 2-(aminomethyl)-5-chloropyridine (18 g, 0.13 mol) was dissolved in dichloromethane (50 mL) and hydrochloric methanol solution (5 M, 50 mL) was added. After stirring for several min a white solid began to precipitate. The mixture was stirred for 1 h at 0-5° C., and the solid was collected by filtration and the filtrate was evaporated in vacuo to give some off-white solid. The combined solid was washed with a small amount of cold DCM. The product was dried in vacuo to yield the indicated compound as the hydrochloric salt. ¹H-NMR (d₆-DMSO, 400 MHz) δ 8.70 (s, 3H), 8.62 (s, 1H), 8.0 (dd, J=2.5, 6 Hz, 1H), 7.60 (d, J=8.5 Hz, 1H), 4.15 (m, 2H).

Step F

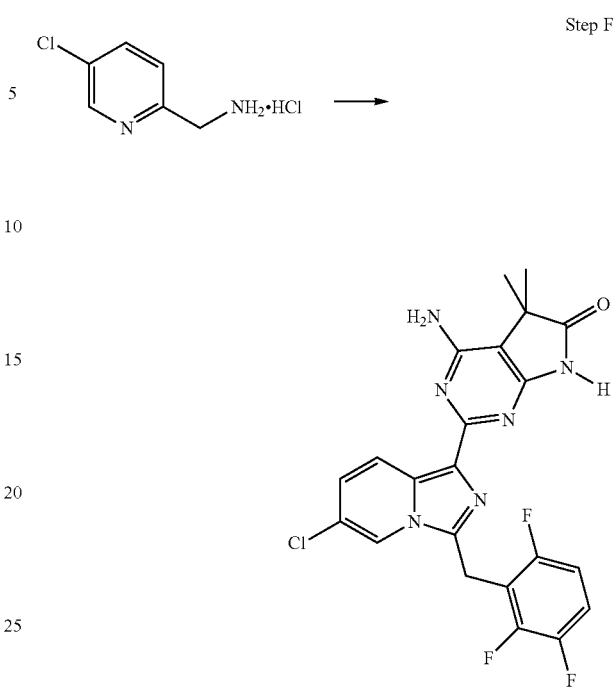

The indicated compound was prepared from the intermediate from Step E using the procedure described in Example 58 substituting NaOMe/MeOH solvent with KOtBu/t-BuOH solvent in the final pyrimidine formation step. ¹H NMR (500 MHz, DMSO-d₆): δ 10.79 (1H, s), 8.75 (1H, s), 8.68 (1H, d, J=9.7 Hz), 7.49 (1H, m), 7.23-7.16 (1H, m), 7.05 (1H, dd, J=9.7, 1.6 Hz), 6.57 (2H, s), 4.51 (2H, s). LC2 1.10 min (M+1) 473.

Example 60

4-AMINO-2-[6-FLUORO-3-(2,3,6-TRIFLUO-ROBENZYL)IMIDAZO[1,5-A]PYRIDIN-1-YL]-5,5-DIMETHYL-5,7-DIHYDRO-6H-PYRROLO[2,3-D]PYRIMIDIN-6-ONE

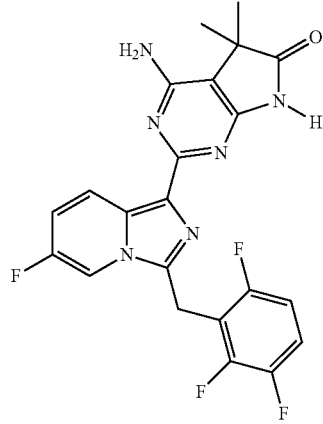 [SMILES: CC1(C)C(=O)Nc2nc(-c3nc(Cc4c(F)ccc(F)c4F)n4cc(F)ccc34)nc(N)c21]

Step A

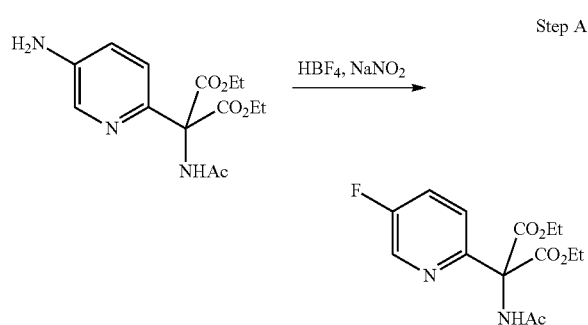

A stirred solution of the intermediate from Step B Example 59 (80 g, 0.25 mol) in 200 mL of 48% aqueous HBF$_4$ was cooled to −5° C. The solution of sodium nitrite (20.7 g, 0.3 mol) in 50 mL of water was added dropwise and kept the reaction mixture below 0° C. After addition, the solution was stirred for another 1 h below 0° C., and then for 2 h at room temperature. The reaction mixture was extracted with dichloromethane (3×100 mL), and the combined organic phases were dried over anhydrous MgSO$_4$ and filtered. The filtrate was concentrated to give a brown yellow oil. The crude product was purified by silica gel chromatography using (petroleum ether/EtOAc=5/1-3/1) to give the indicated compound as a pale yellow solid.

Step B

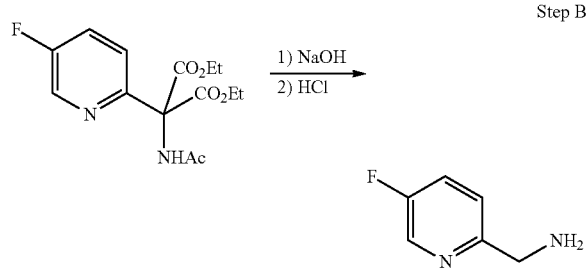

To a solution of diethyl (5-fluoro-2-pyridyl)acetamidomalonate from Step A (70 g, 0.21 mol) in 200 mL of 95% ethanol was added sodium hydroxide solution (105 mL, 8 N). After refluxing for 2 h, the mixture was cooled to 5° C. and acidified to pH 2 with hydrochloric acid (6 N, ~40 mL). The ethanol in the solution was evaporated in vacuum to give a mixture containing some solid, and then 150 mL of hydrochloric acid (5 N) was added. The mixture was heated to 80° C. for 4 h, and then maintained at room temperature overnight. Sodium hydroxide solution (4 N) was slowly added to the mixture to adjust pH 10. The mixture was extracted with DCM (4×200 mL), and then the combined organic phases were dried over anhydrous Na$_2$SO$_4$ and filtered. The solvent was evaporated to give the indicated product as a pale yellow oil which decomposed on prolonged contact with air. $^1$H-NMR (CDCl$_3$, 400 MHz) δ 8.42 (s, 1H), 7.4 (m, 1H), 3.99 (s, 2H), 1.79 (m, 2H). MS: m/z=127 (M+H).

Step C

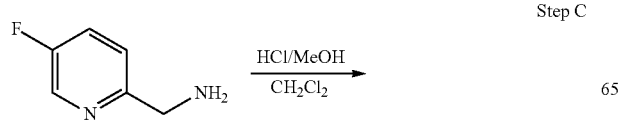

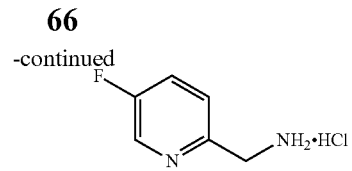

The compound 2-(aminomethyl)-5-fluoropyridine from Step B (18 g, 0.14 mol) was dissolved in dichloromethane (50 mL) and hydrochloric methanol solution (5 M, 50 mL) was added. After stirring for several min a white solid began to precipitate. The mixture was stirred for 1 h at 0-5° C., and the solid was collected by filtration and the filtrate was evaporated to give some off-white solid. The combined solid was washed with a small amount of cold DCM. The product was dried in vacuo to give the indicated compound as the dihydrochloric salt. $^1$H NMR (d$_6$-DMSO, 400 MHz) δ 8.70 (s, 3H), 8.62 (s, 1H), 7.8 (m, 1H), 7.64 (m, 1H), 4.13 (m, 2H). MS: m/z=127 (M+H).

Step D

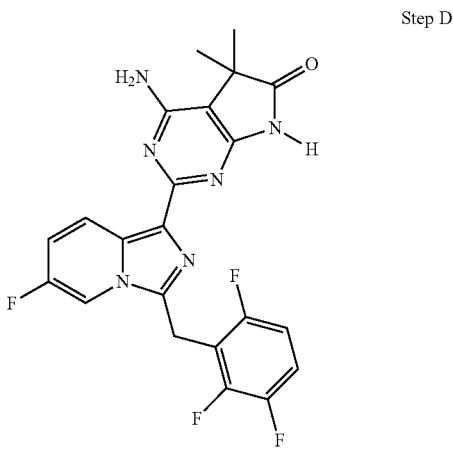 [SMILES: CC1(C)C(=O)Nc2nc(-c3nc(Cc4c(F)ccc(F)c4F)n4cc(F)ccc34)nc(N)c21]

The indicated compound was prepared from the intermediate from Step C using the procedure described in Example 58 substituting NaOMe/MeOH solvent with KOtBu/t-BuOH solvent in the final pyrimidine formation step. $^1$H NMR (500 MHz, DMSO-d$_6$): δ 8.74 (1H, s), 8.65 (1H, s), 7.47 (1H, m), 7.25 (1H, s), 7.22-7.13 (1H, m), 4.52 (2H, s), 1.33 (6H, s). LC2 rt=1.05 min, m/z=457 (M+H).

Example 61

4-AMINO-5,5-DIMETHYL-2-[5-(2,3,6-TRIFLUO-ROBENZYL)IMIDAZO[5,1-B][1,3]THIAZOL-7-YL]-5,7-DIHYDRO-6H-PYRROLO[2,3-D]PYRI-MIDIN-6-ONE

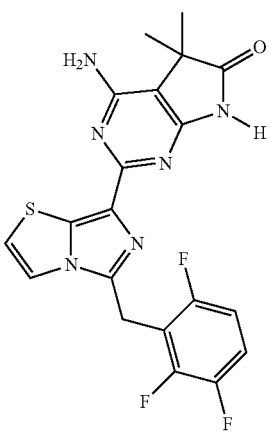 [SMILES: CC1(C)C(=O)Nc2nc(-c3nc(Cc4c(F)ccc(F)c4F)n4ccsc34)nc(N)c21]

The indicated compound was prepared from 2-aminoethylthiazole using the procedure described in Example 58 substituting NaOMe/MeOH solvent with KOtBu/t-BuOH solvent in the final pyrimidine formation step. $^1$H NMR (500 MHz, DMSO-d$_6$): δ 10.77 (s, 1H); 8.05 (d, J=4.4 Hz, 1H); 7.50 (m, 1H); 7.43 (d, J=4.1 Hz, 1H); 7.18 (m, 1H); 6.46 (broad s, 2H); 4.42 (s, 2H); 1.29 (s, 6H). LC3 rt=1.41 min, m/z=445 (M+H).

Example 62

4-AMINO-5,5-DIMETHYL-2-[1-(2,3,6-TRIFLUOROBENZYL)IMIDAZO[1,5-A]PYRIDIN-3-YL]-5,7-DIHYDRO-6H-PYRROLO[2,3-D]PYRIMIDIN-6-ONE

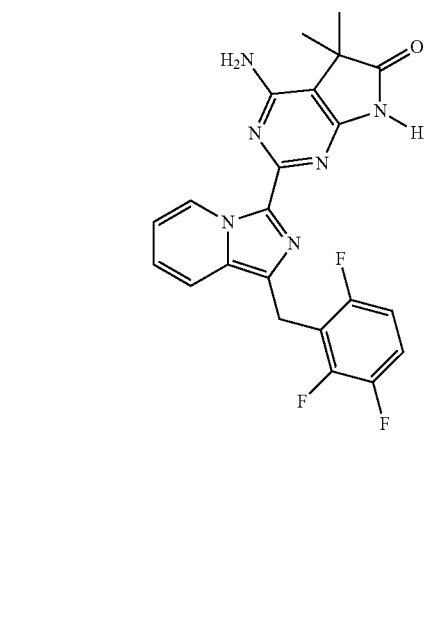

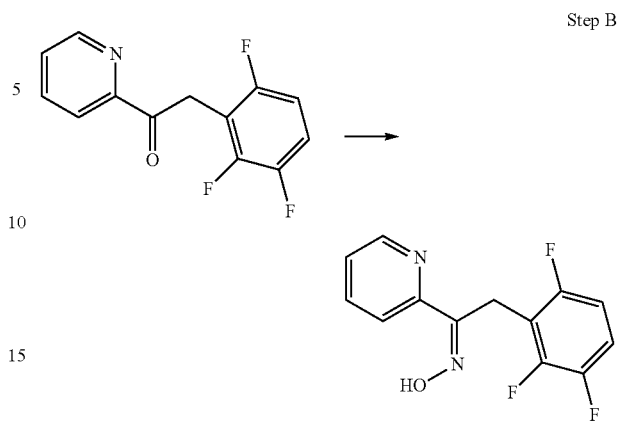

Step A

The intermediate from Step A (1.1 g, 4.38 mmol) was dissolved in MeOH and hydroxylamine (0.268 mL, 4.38 mmol) was added. After stirring the reaction overnight the solution was concentrated. The residue was diluted with ethyl acetate and water. The organic layer was washed with brine, dried over anhydrous sodium sulfate, filtered and concentrated to give the indicated compound.

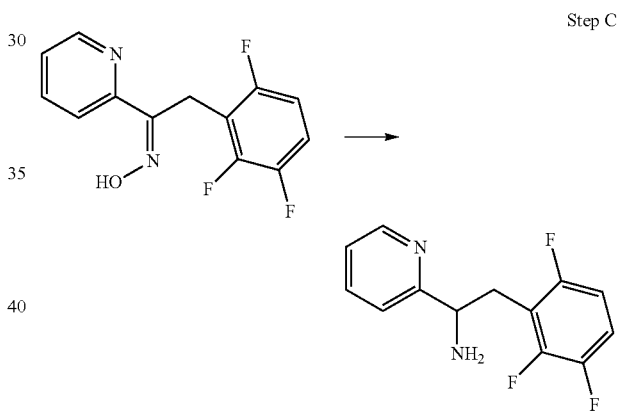

Step C

A solution of NaHMDS (1.0M THF, 15.78 mL, 15.78 mmol) was added to a THF (11 mL) solution of 2,3,6 trifluorophenylacetic acid (1 g, 5.26 mmol) cooled to −78° C. under a nitrogen atmosphere. The mixture was stirred for 20 minutes. Methyl picolinate (0.634 mL, 5.26 mmol) was then added and the reaction stirred for 30 min. The solution was then warmed to room temperature and quenched with 1N aqueous hydrochloric acid. The solution was then diluted with EtOAc and washed with 1N NaHCO$_3$ and brine. The organic phase was then dried over anhydrous sodium sulfate, filtered and concentrated to give the indicated compound.

The crude intermediate from Step B (ca. 4.38 mmol) was dissolved in TFA and cooled to 0° C. Zinc (1.432 g, 21.89 mmol) was then added in one portion. After 15 minutes the reaction mixture was poured on ice and 5N NaOH mixture. The pH was adjusted to 10 with NaOH. The mixture was then extracted with DCM (3×). The organic layer was washed with brine, dried over sodium sulfate, filtered and concentrated. The crude amine was purified silica gel chromatography using a hexanes/EtOAc gradient to give the indicated compound. LC2 rt=0.33 min, m/z=254 (M+H).

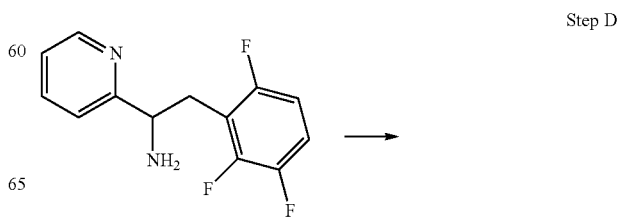

Step D

-continued

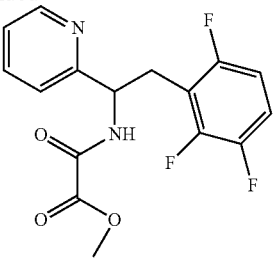

The intermediate from Step C (300 mg, 1.189 mmol) was dissolved in DCM (3 mL) and DIEA (208 µl, 1.189 mmol) was added. Methyl oxalyl chloride (652 µl, 5.95 mmol) was then added to the reaction mixture. The mixture was allowed to stir at room temperature overnight. The reaction was partitioned between water and DCM. The organic layer was washed with brine, dried over anhydrous sodium sulfate, filtered and concentrated to give the indicated product.

Step E

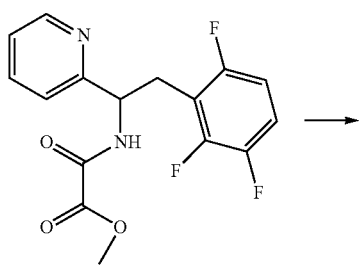

Phosphorous oxychloride (5 mL, 53.6 mmol) was added to the intermediate from Step D (400 mg, 1.135 mmol). The mixture was heated at 105° C. overnight. The reaction solution was then poured onto ice and neutralized with sodium carbonate. The mixture was extracted with DCM. The organic layer was washed with brine, dried over anhydrous sodium sulfate, filtered and concentrated to give the indicated. LC2 rt=1.15 min, m/z=335 (M+H).

Step F

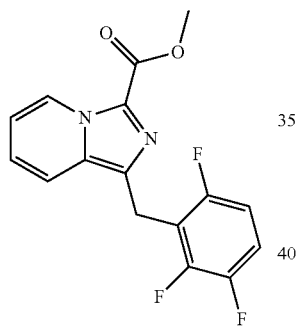

-continued

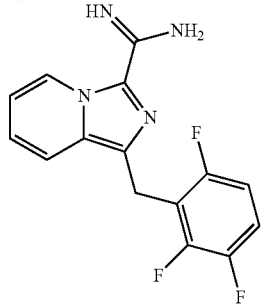

To the intermediate from Step E (260 mg, 0.81 mmol) was added amino(chloro)methylaluminum (0.5M in toluene, 10 mL, 5 mmol). The reaction was carried out as described in Step H Example 58. LC2 rt=0.91 min, m/z=305 (M+H).

Step G

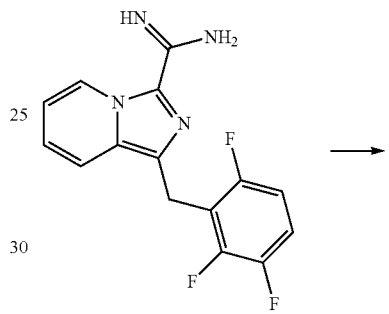

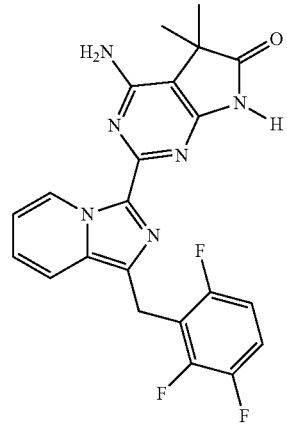 [SMILES: CC1(C)C(=O)Nc2nc(-c3nc(Cc4c(F)ccc(F)c4F)c4ccccn34)nc(N)c21]

A t-butanol (2 mL) solution of the intermediate from Step F (246 mg, 0.81 mmol), Intermediate 1 (269 mg, 1.6 mmol)) and potassium tert-butoxide (91 mg, 0.81 mmol) were heated at 140° C. for 30 minutes in a screw cap tube. The reaction was cooled to room temperature and concentrated. The residue was partitioned between EtOAc and water. The organic layer was washed with brine, dried over anhydrous sodium sulfate, filtered and concentrated. The crude was purified by silica gel chromatography using a hexanes/EtOAc gradient followed by 10% MeOH/DCM to give the indicated compound. $^1$H NMR (500 MHz, DMSO-$d_6$): δ 10.96 (broad s, 1H); 9.90 (d, J=7.3 Hz, 1H); 7.78 (d, J=9.1 Hz, 1H); 7.38 (m, 1H); 7.11 (t, J=9.5 Hz, 1H); 7.00 (t, J=7.8 Hz, 1H); 6.85 (t, J=7.0 Hz, 1H); 6.79 (s, 2H); 4.30 (s, 2H); 1.32 (s, 6H). LC2 rt=1.05 min, m/z=439 (M+H).

Using essentially the same procedures described in Examples 58 to 62, the following compounds in Table 3 and Table 4 were made.

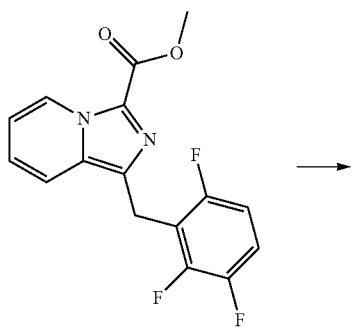

TABLE 3

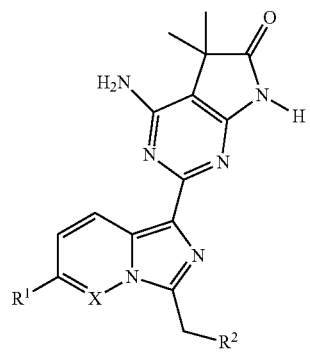

| EXAMPLE | R¹ | R² | X | LC-MS data | Method |
|---|---|---|---|---|---|
| 63 | H | 2,3 di F—Ph | CH | 1.05 min.(M + H) 421 | LC2 |
| 64 | H | 2,3 di F—Ph | N | 1.05 min.(M + H) 422 | LC2 |
| 65 | F | 2,3 di F—Ph | CH | 1.06 min.(M + H) 439 | LC2 |
| 66 | H | 2 F—Ph | N | 1.05 min.(M + H) 404 | LC2 |
| 67 | H | 2 F—Ph | CH | 1.04 min.(M + H) 403 | LC2 |
| 68 | F | 2 F—Ph | CH | 1.06 min.(M + H) 421 | LC2 |
| 69 | Cl | 2 F—Ph | CH | 1.08 min.(M + H) 437 | LC2 |
| 70 | Me | 2,3 di F—Ph | N | 1.62 min.(M + H) 436 | LC3 |
| 71 | Cl | 2,3 di F—Ph | CH | 1.65 min.(M + H) 455 | LC3 |
| 72 | H | Ph | CH | 1.04 min.(M + H) 385 | LC2 |
| 73 | H | 2,3,6-tri F—Ph | CH | 1.49 min.(M + H) 439 | LC3 |
| 74 | Ph | 2,3,6-tri F—Ph | CH | 1.14 min.(M + H) 515 | LC2 |
| 75 | 2-F Ph | 2,3,6-tri F—Ph | CH | 1.13 min.(M + H) 533 | LC2 |
| 76 | 3-F Ph | 2,3,6-tri F—Ph | CH | 1.14 min.(M + H) 533 | LC2 |
| 77 | 4-F Ph | 2,3,6-tri F—Ph | CH | 1.14 min.(M + H) 533 | LC2 |
| 78 | 3-Cl Ph | 2,3,6-tri F—Ph | CH | 1.17 min.(M + H) 549 | LC2 |
| 79 | 3-thienyl | 2,3,6-tri F—Ph | CH | 1.13 min.(M + H) 521 | LC2 |
| 80 | cyclopropyl | 2,3,6-tri F—Ph | CH | 1.12 min.(M + H) 479 | LC2 |
| 81 | H | CH₂CF₃ | N | 0.98 min.(M + H) 392 | LC2 |
| 82 | H | 2,4,6-tri F—Ph | CH | 1.03 min.(M + H) 439 | LC2 |
| 83 | H | 2-Cl, 3-Me, 6-F—Ph | CH | 1.07 min.(M + H) 450 | LC2 |
| 84 | H | cyclopentyl | CH | 1.1 min.(M + H) 391 | LC2 |
| 85 | H | CH₂CH₂CF₃ | N | 1.03 min.(M + H) 406 | LC2 |
| 86 | H | CH₂CH₂CF₃ | CH | 1.02 min.(M + H) 405 | LC2 |
| 87 | H | 2-thienyl | CH | 1.38 min.(M + H) 405 | LC4 |
| 88 | H | cyclopropyl | CH | 0.98 min.(M + H) 363 | LC2 |
| 89 | H | (CH₂)₃CH₃ | CH | 0.98 min.(M + H) 365 | LC2 |
| 90 | H | (CH₂)₃CH₃ | N | 1.35 min.(M + H) 366 | LC4 |
| 91 | H | CH₂CH(CH₃)₂ | CH | 1.48 min.(M + H) 365 | LC4 |

TABLE 4

[Structure: pyrrolo[2,3-d]pyrimidinone with H2N, X-CH2-R2 substituents]

| EXAMPLE | X | R² | LC-MS data | Description |
|---|---|---|---|---|
| 92 | [thiazolo-imidazole, methyl-substituted] | 2,3,6-tri F—Ph | 1.75 min. (M + H) 459 | LC3 |
| 93 | [thiazolo-imidazole, methyl-substituted] | 2,3,6-tri F—Ph | 1.52 min. (M + H) 459 | LC3 |
| 94 | [thiazolo-imidazole] | 2-F—Ph | 1.38 min. (M + H) 409 | LC3 |

Example 95

4-AMINO-5,5-DIMETHYL-2-[1-(3,3,3-TRIFLUO-ROPROPYL)-1H-INDAZOL-3-YL]-5,7-DIHY-DRO-6H-PYRROLO[2,3-D]PYRIMIDIN-6-ONE

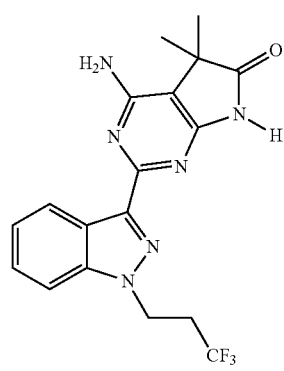 [SMILES: CC1(C)C(=O)Nc2nc(-c3nn(CCC(F)(F)F)c4ccccc34)nc(N)c21]

Step A

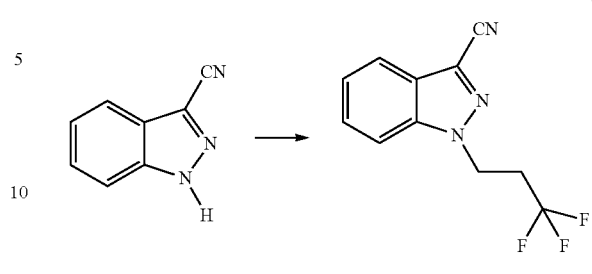

Potassium t-butoxide (0.972 g, 8.66 mmol) was added to 3-cyano indazole (1.24 g, 8.66 mmol) in 8 mL THF. After 5 min 1,1,1-trifluoro-3-iodopropane (1.94 g, 8.66 mmol) was added. The solution was then heated to 60° C. After 1 hour 6 mL of DMF, potassium t-butoxide (0.972 g, 8.66 mmol) and 1,1,1-trifluoro-3-iodopropane (1.94 g, 8.66 mmol) were added. After stirring for an additional 2 hours at 60° C. the reaction solution was partitioned between EtOAc and aqueous 1 N HCl. The organic phase was dried over MgSO$_4$, filtered and concentrated. The residue was purified by silica gel chromatography using a hexanes/EtOAc gradient to give the indicated product. $^1$H NMR (400 MHz, CD3CN): δ 7.84 (d, 1H); 7.72 (d, 1H); 7.60-7.54 (m, 1H); 7.39 (t, 1H); 4.73 (t, 2H); 2.96-2.82 (m, 2H). LC4 rt=3.78 min, m/z=240 (M+H)

Step B

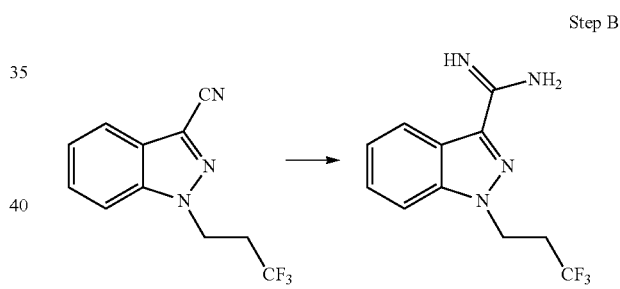

Amino(chloro)methylaluminum (0.5M in toluene, 6 mL, 3 mmol) and the intermediate from Step A (306 mg, 1.279 mmol) were heated at 100° C. for 4 hours. The solution was cooled to room temperature and 7 g of silica gel and 30 mL of MeOH were added. After stirring for 3 hours the mixture was filtered and concentrated to give the indicated product. LC4 rt=2.14 min, m/z=257 (M+H)

Step C

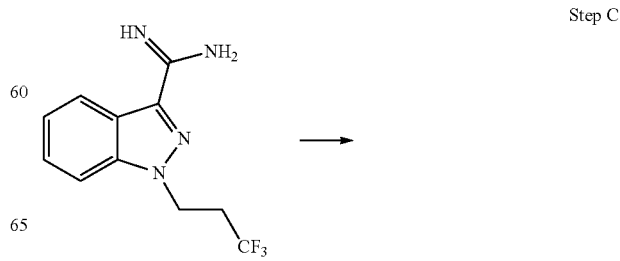

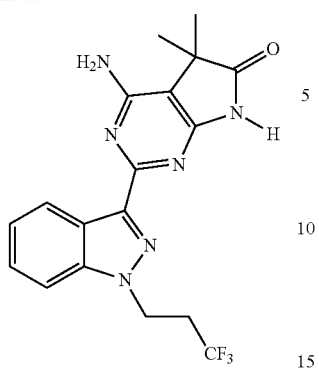

The indicated product was prepared from the intermediate from Step B and Intermediate 1 using the procedure described in Example 1. $^1$H NMR (400 MHz, CD 30D): δ 8.64 (d, 1H); 7.58 (d, 1H); 7.44 (t, 1H); 7.24 (t, 1H); 4.73 (t, 2H); 2.97-2.87 (m, 2H); 1.44 (s, 6H). LC4 rt=2.81 min, m/z=391 (M+H)

Example 96

4-AMINO-2-[5-CHLORO-3-(2,3,6-TRIFLUO-ROBENZYL)-1H-INDAZOL-1-YL]-5,5-DIM-ETHYL-5,8-DIHYDROPYRIDO[2,3-D]PYRIMI-DIN-7(6H)-ONE

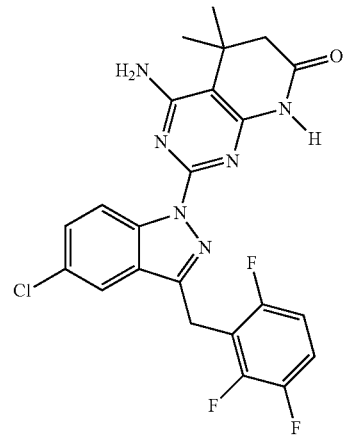 [SMILES: CC1(C)CC(=O)Nc2nc(-n3nc(Cc4c(F)ccc(F)c4F)c4cc(Cl)ccc43)nc(N)c21]

Step A

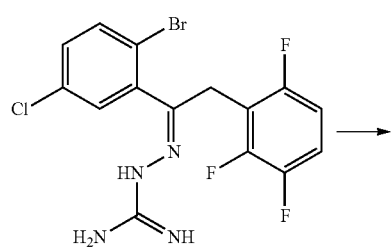

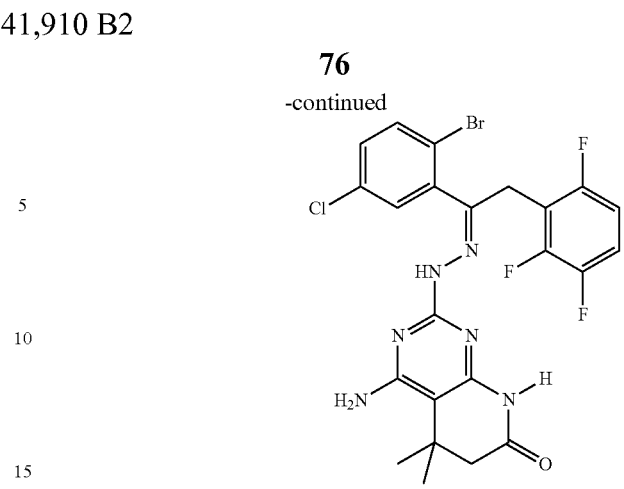

A n-butanol (4 mL) solution containing the Intermediate 4 (143 mg, 0.736 mmol), the intermediate from Example 3 Step B (103 mg, 0.245 mmol) and potassium t-butoxide (27 mg, 0.245 mmol) was heated at 140° C. for 1 hour. The solution was partitioned between EtOAc and water. The organic phase was washed with water, brine and dried over MgSO$_4$. The solution was filtered and concentrated. The residue was used in the next step without purification. LC4 rt=2.94 min, m/z=567 (M+H).

Step B

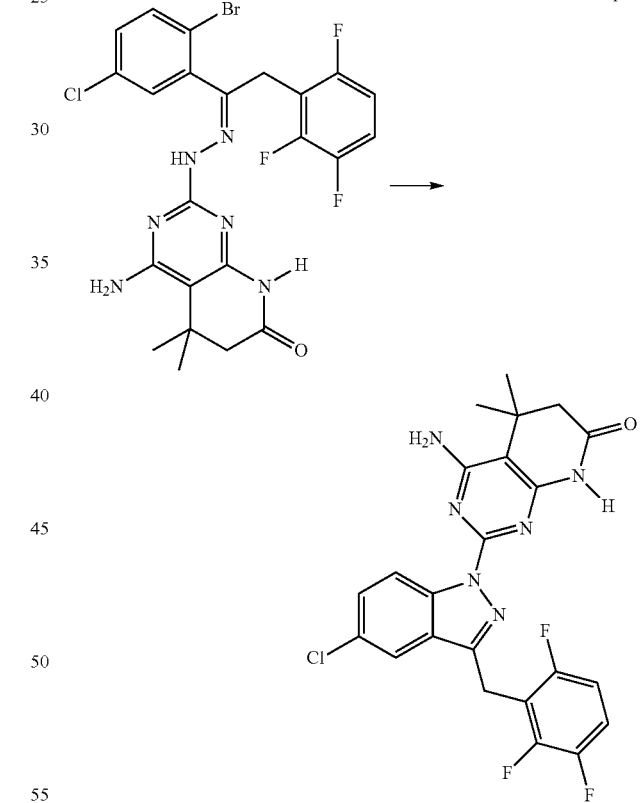

To the crude compound from Step A (ca 0.24 mmol) was added 6 mL DMF, trans-N,N'-dimethylcyclohexane-1,2-diamine (35 mg, 0.25 mmol) and copper iodide (45 mg, 0.24 mmol). The reaction solution was stirred for 15 min. The reaction solution was partitioned between EtOAc and 6% aqueous ammonium hydroxide. The organic phase was washed with brine, dried over anhydrous MgSO4, filtered and concentrated. The residue was purified by reverse phase HPLC to give the indicated product. $^1$H NMR (400 MHz, CD$_3$CN): δ 8.76 (d, J=8.0 Hz, 1H); 8.53 (s, 1H); 7.74 (m, 1H); 7.46 (m, 1H); 7.26-7.15 (m, 1H); 7.02-6.93 (m, 1H); 5.63 (s, 2H); 4.38 (s, 2H); 2.48 (s, 2H); 1.35 (s, 6H). LC4 rt=3.96 min, m/z=487 (M+H).

Using essentially the same procedure described in Example 96, the following compounds in Table 5 were made.

TABLE 5

| EXAMPLE | X | LC-MS data | Method |
|---|---|---|---|
| 97 | (indazole) | 3.64 min. (M + H) 453 | LC4 |
| 98 | (thienopyrazole) | 3.51 min. (M + H) 459 | LC4 |
| 99 | (dihydrothienopyrazole) | 3.61 min. (M + H) 461 | LC4 |

Example 100

4-AMINO-2-[5-CHLORO-3-(3,3,3-TRIFLUORO-PROPYL)-1H-INDAZOL-1-YL]-5-ETHYL-5-METHYL-5,7-DIHYDRO-6H-PYRROLO[2,3-D]PYRIMIDIN-6-ONE

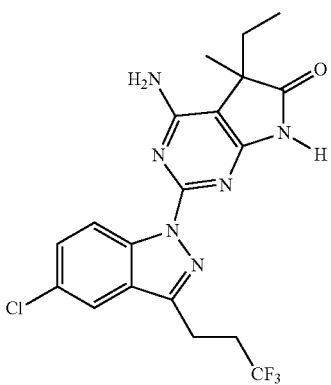 [SMILES: CCC1(C)C(=O)Nc2nc(-n3nc(CCC(F)(F)F)c4cc(Cl)ccc43)nc(N)c21]

The indicated product was prepared using Intermediate 2 as described in Example 1. LC4 3.86 min (M+H) 439. The racemic compound was resolved on a ChiralPak AD-H column eluting with 40% IPA/CO$_2$ to give enantiomer 1 (faster eluting). Retention time=3.91 min (4.6×250 mm ChiralPak AD-H, 2.4 ml/min, 100 bar). $^1$H NMR (500 MHz, DMSO-d$_6$): δ 11.11 (s, 1H), 8.83 (d, 1H, J=8.9 Hz), 8.06 (d, 1H, J=1.8 Hz), 7.56 (dd, 1H, J=2.0 Hz, 9.0 Hz), 6.94 (br s, 2H), 3.25-3.22 (m, 2H), 2.86-2.76 (m, 2H), 2.13-2.06 (m, 1H), 1.70-1.63 (m, 1H), 1.32 (s, 3H), 0.54 (m, 3H).

Data for enantiomer 2 (slower eluting): Retention time=4.31 min (4.6×250 mm ChiralPak AD-H, 2.4 ml/min, 100 bar). $^1$H NMR (500 MHz, DMSO-d$_6$): δ 11.11 (s, 1H), 8.83 (d, 1H, J=8.9 Hz), 8.06 (d, 1H, J=1.8 Hz), 7.56 (dd, 1H, J=2.0 Hz, 9.0 Hz), 6.94 (br s, 2H), 3.25-3.22 (m, 2H), 2.86-2.76 (m, 2H), 2.13-2.06 (m, 1H), 1.70-1.63 (m, 1H), 1.32 (s, 3H), 0.54 (m, 3H).

Example 101

4-AMINO-2-[5-CHLORO-3-(3,3,3-TRIFLUORO-PROPYL)-1H-INDAZOL-1-YL]-5-METHYL-5-PROPYL-5,7-DIHYDRO-6H-PYRROLO[2,3-D]PYRIMIDIN-6-ONE

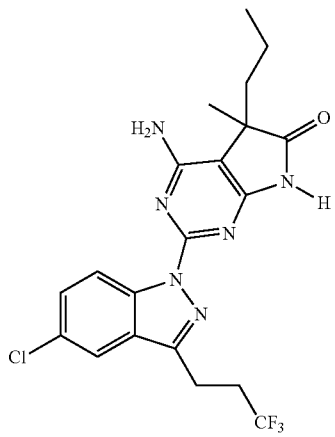 [SMILES: CCCC1(C)C(=O)Nc2nc(-n3nc(CCC(F)(F)F)c4cc(Cl)ccc43)nc(N)c21]

The indicated product was prepared using Intermediate 3 as described in Example 1. LC4 3.95 min (M+H) 453. The racemic compound was resolved on a ChiralCel AD-H column eluting with 40% IPA/CO$_2$ to give enantiomer 1 (faster eluting): Retention time=3.53 min (4.6×250 mm ChiralPak AD-H, 2.4 ml/min, 100 bar). $^1$H NMR (500 MHz, DMSO-d$_6$): δ 10 (s, 1H), 8.82 (d, 1H, J=9.0 Hz), 8.06 (d, 1H, J=1.8 Hz), 7.52 (dd, 1H, J=2.0 Hz, J=9.0 Hz), 6.94 (br s, 2H), 3.24-3.22 (m, 2H), 2.86-2.76 (m, 2H), 2.10-2.05 (m, 1H), 1.65-1.59 (m, 1H), 1.31 (s, 3H), 0.94-0.86 (m, 2H), 0.79-0.76 (m, 3H).

Data for enantiomer 2 (slower eluting): Retention time=4.19 min (4.6×250 mm ChiralPak AD-H, 2.4 ml/min, 100 bar). $^1$H NMR (500 MHz, DMSO-d$_6$): δ 10 (s, 1H), 8.82 (d, 1H, J=9.0 Hz), 8.06 (d, 1H, J=1.8 Hz), 7.52 (dd, 1H, J=2.0 Hz, J=9.0 Hz), 6.94 (br s, 2H), 3.24-3.22 (m, 2H), 2.86-2.76 (m, 2H), 2.10-2.05 (m, 1H), 1.65-1.59 (m, 1H), 1.31 (s, 3H), 0.94-0.86 (m, 2H), 0.79-0.76 (m, 31-1).

Using essentially the same procedure described in Example 100, the following racemic compounds in Table 6 were made.

TABLE 6

| EXAMPLE | Structure | LC-MS data | Method |
|---|---|---|---|
| 102 | (structure with ethyl, methyl, H₂N-pyrrolopyrimidinone, linked to 5-chloro-3-(3,3-dimethylbutyl)indazole) | 4.31 min. (M + H) 427 | LC4 |
| 103 | (structure with ethyl, methyl, H₂N-pyrrolopyrimidinone, linked to imidazo[1,5-a]pyridine with 2-fluorobenzyl) | 0.99 min. (M + H) 417 | LC2 |

Using essentially the same procedures described in Examples 1, 60 and 95 the following compounds in Table 7 were made.

TABLE 7

Core structure: H₂N-(5,5-dimethyl-pyrrolopyrimidinone)-X-CH₂CH₂-CF₂-CF₃

| EXAMPLE | X | LC-MS data | Method |
|---|---|---|---|
| 104 | 1H-indazol-1,3-diyl | 3.63 min. (M + H) 441 | LC4 |
| 105 | 5-fluoro-1H-indazol-1,3-diyl | 3.74 min. (M + H) 459 | LC4 |
| 106 | 5-chloro-1H-indazol-1,3-diyl | 3.94 min. (M + H) 475 | LC4 |
| 107 | 1H-pyrazolo[3,4-b]pyridin-1,3-diyl | 3.35 min. (M + H) 442 | LC4 |
| 108 | imidazo[1,5-a]pyridin-1,3-diyl | 1.12 min. (M + H) 441 | LC2 |
| 109 | 6-fluoro-imidazo[1,5-a]pyridin-1,3-diyl | 1.12 min. (M + H) 459 | LC2 |
| 110 | 6-chloro-imidazo[1,5-a]pyridin-1,3-diyl | 1.13 min. (M + H) 475 | LC2 |
| 111 | 6-chloro-1H-indazol-1,3-diyl | 3.43 min. (M + H) 475 | LC4 |

Example 112

Cell-Based sGC Functional Assay (CASA Assay)

Rationale: sGC is a heme-containing enzyme that converts GTP to secondary messenger cGMP. Increases in cGMP levels affect several physiological processes including vasorelaxation through multiple downstream pathways. The rate by which sGC catalyzes cGMP formation is greatly increased by NO and by recently discovered NO-independent activators and stimulators. Heme-dependent activators (HDAs) preferentially activate sGC containing a ferrous heme group. To determine the effect of sGC activators on enzyme activity, the CASA assay was developed to monitor the generation of cGMP in a cell line that stably expresses the heterodimeric sGC protein.

Methods:

A CHO-K1 cell line stably expressing the sGC α1/β1 heterodimer was generated using a standard transfection protocol. CHO-K1 cells were transfected with plasmids pIREShyghsGCα1 and pIRESneo-hsGCβ1 simultaneously using FUGENE reagent. Clones that stably express both subunits were selected with hygromycin and neomycin for ~2 weeks. Clone #7 was chosen for the assay and was designated CHO-K1/sGC. CHO-K1/sGC cells were maintained in F-K12 medium containing 10% heat-inactivated Fetal Bovine Serum (FBS), 100 µg/mL penicillin/streptomycin, 0.5 mg/mL hygromycin and 0.25 mg/mL G418. On the day of the assay, cells were harvested in EBSS Assay Buffer (EAB) containing 5 mM MgCl2, 10 mM HEPES and 0.05% BSA and cell density was adjusted to $2\times10^6$/mL with EAB. IBMX (3-isobutyl-1-methylxanthin, 0.5 mM) was added to inhibit degradation of cGMP. Compounds were diluted from DMSO stock solutions and added to the assay at a final DMSO concentration of 1%. Cells were incubated with compounds in the presence and absence of 10 µM of 1H-(1,2,4)oxadiazolo(4,3-a)quinoxalin-1-one (ODQ) for 1 hr at 37 oC. At the end of the incubation period, the reaction was terminated and the cells were lysed. The level of intracellular cGMP was determined using an HTRF-based assay kit (CisBio, 62GM2PEC), which detects the displacement of a fluorescence labeled cGMP from its specific antibody. The amount of cGMP was plotted against compound concentration in PRISM software and the IP and maximum fold induction over DMSO control were derived from the plot.

Compounds of the instant invention had EC 50s less than or equal to about 1 µM. Preferable compounds had an EC 50s less than or equal to about 500 nM. Results for specific compounds are as follows:

What is claimed is:

1. A compound having structural Formula I, or a pharmaceutically acceptable salt thereof:

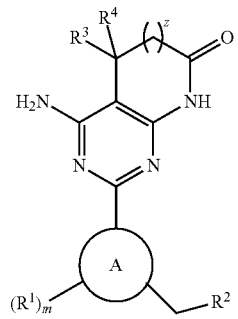

wherein:

is an 8- or 9-membered heteroaryl;

$R^a$ and $R^b$ are independently selected at each occurrence from the group consisting of —H and —$C_1$-$C_6$ alkyl;

$R^c$ is independently selected at each occurrence from the group consisting of —$C_1$-$C_6$ alkyl, —$CF_3$, and aryl;

$R^1$ is independently selected at each occurrence from the group consisting of —H, halo, aryl, heteroaryl, —$C_1$-$C_6$ alkyl, —$C_{3-10}$ cycloalkyl, —OR, —$NO_2$, —CN, —$CO_2R^a$, —$NR^aR^b$, —$S(O)_pR^c$, thioxo, azido, —C(=O)$R^a$, —OC(O)$R^a$, —OC(=O)$OR^a$, —OC(=O)$NR^aR^b$, —$SO_2NR^aNR^b$, —$NR^a$(C=O)$R^b$, —$NR^aSO_2R^b$, —$NR^aC$(=O)$OR^b$, —$NR^aC$(O)$NR^aR^b$, —$NR^aSO_2NR^aR^b$, —$C_{2-10}$alkenyl, and —$C_{2-10}$alkynyl, said aryl, heteroaryl, alkyl, cycloalkyl, alkenyl and alkynyl optionally being substituted with one to three substituents selected from halo, —$C_1$-$C_6$ alkyl, —OR, oxo, aryl, heteroaryl, —$C_{3-10}$ cycloalkyl, —$NO_2$, —CN, $CO_2R^a$, $NR^aR^b$, —$S(O)_pR^c$, thioxo, azido, —C(=O)$R^a$, —O(C=O)$R^a$, —OC(=O)$OR^a$, —OC(=O)$NR^aR^b$, —$SO_2NR^aNR^b$, —$NR^a$(C=O)$R^b$, —$NRaSO_2R^b$, —$NR^aC$(=O)$OR^b$, —$NR^aC$(=O)$NR^aR^b$, —$NR^aSO_2NR^aR^b$ and —$CF_3$;

$R^2$ is selected from the group consisting of —$C_1$-$C_6$ alkyl, —$(CR^a_2)_r$OR, —$(CR^a_2)_r$S(O)$_pR^c$, —$(CR^a_2)_r$CF_3, —$(CR^a_2)_r$—$C_{3-10}$cycloalkyl, —$(CR^a_2)_r$aryl, —$(CR^a_2)_r$heteroaryl, —$(CR^a_2)_r$—$C_{2-10}$alkenyl,

| Example | IUPAC NAME | $EC_{50}$ |
|---|---|---|
| 1 | 4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one | 86 nM |
| 3 | 4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one | 7 nM |
| 59 | 4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one | 24 nM |
| 60 | 4-amino-2-[6-fluoro-3-(2,3,6-trifluorobenzyl)imidazo[1,5-a]pyridin-1-yl]-5,5-dimethyl-5,7-dihydro-6H-pyrrolo[2,3-d]pyrimidin-6-one | 31 nM |
| 111 | 4-amino-2-[6-chloro-1-(3,3,4,4,4-pentafluorobutyl)-1H-indazol-3-yl]-5,5-dimethyl-5,7-dihydro-6H-pyrrolo[2,3-d]pyrimidin-6-one | 83 nM |

—(CR$^a_2$)$_r$—C$_{2-10}$alkynyl, and —(CR$^a_2$)$_r$C(O)Oalkyl, said alkyl, cycloalkyl, aryl, hetetoaryl, alkenyl and alkynyl being optionally substituted with one to three substituents selected from halo, —C$_1$-C$_6$ alkyl, —CF$_3$, —CN and —OR;

R is independently selected at each occurrence from the group consisting of —H, —C$_1$-C$_6$ alkyl, —CF$_3$, and aryl;

R$^3$ and R$^4$ are independently selected from the group consisting of —H and —C$_1$-C$_6$ alkyl;

when R$^3$ and R$^4$ are C$_1$-C$_6$ alkyl they may optionally be joined to form a cycloalkyl;

m is 0, 1, 2, or 3;

p is 0, 1 or 2;

r is 0, 1, 2, 3, 4, 5, or 6; and z is 0 or 1.

2. The compound of claim 1 having structural Formula II, or a pharmaceutically acceptable salt thereof,

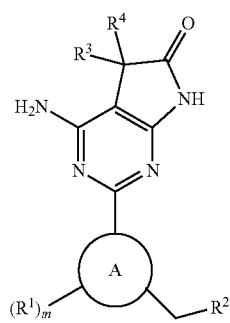

II wherein:

is an 8- or 9-membered heteroaryl;

R$^a$ is independently selected at each occurrence from the group consisting of —H and —C$_1$-C$_6$ alkyl;

R$^1$ is independently selected at each occurrence from the group consisting of —H, halo, aryl, heteroaryl, —C$_1$-C$_6$ alkyl and —C$_{3-10}$ cycloalkyl, said aryl, heteroaryl, alkyl and cycloalkyl optionally being substituted with one to three substituents selected from halo, —C$_1$-C$_6$ alkyl, and —CF$_3$;

R$^2$ is selected from the group consisting of —C$_1$-C$_6$ alkyl, —(CR$^a_2$)$_r$CF$_3$, —(CR$^a_2$)$_r$—C$_{3-10}$cycloalkyl, —(CR$^a_2$)$_r$aryl, —(CR$^a_2$)$_r$heteroaryl, —(CR$^a_2$)$_r$alkenyl, —(CR$^a_2$)$_r$alkynyl, and —(CR$^a_2$)$_r$C(O)Oalkyl, said alkyl, cycloalkyl, aryl, hetetoaryl, alkenyl and alkynyl being optionally substituted with one to three substituents selected from halo, —C$_1$-C$_6$ alkyl, —CF$_3$, —CN, and —OR;

R is independently selected at each occurrence from the group consisting of —H, —C$_1$-C$_6$ alkyl and aryl;

R$^3$ and R$^4$ are independently selected from the group consisting of H and C$_1$-C$_6$ alkyl;

when R$^3$ and R$^4$ are C$_1$-C$_6$ alkyl they may optionally be joined to form a cycloalkyl;

m is 0, 1, 2 or 3; and r is 0, 1, 2, 3, 4, 5, or 6.

3. The compound of claim 2, wherein

is selected from the group consisting of

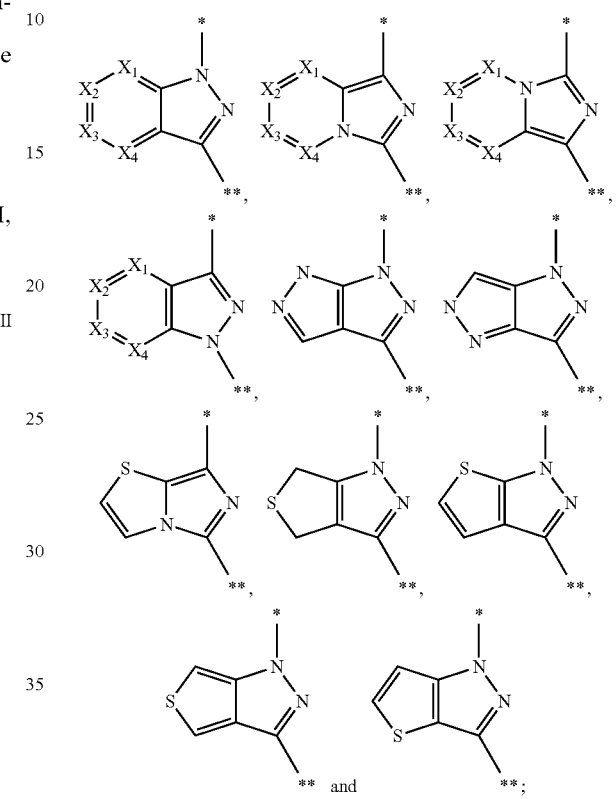

where * indicates attachment to the pyrmidinyl ring and ** indicates attachment to the —CH$_2$—R$^2$ of structural Formula II; and X$^1$, X$^2$, X$^3$ and X$^4$ are independently selected from N or CH, provided that no more than one of X$^1$, X$^2$, X$^3$ and X$^4$ is N.

4. The compound of claim 2 wherein

is selected from the group consisting of

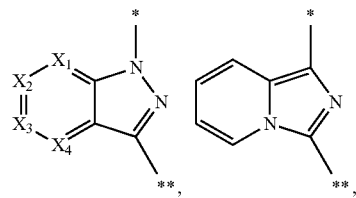

-continued

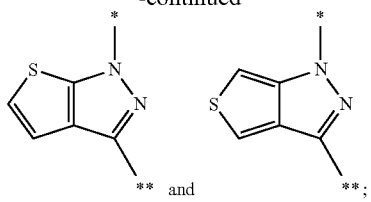

where * indicates attachment to the pyrmidinyl ring and ** indicates attachment to the —CH$_2$—R$^2$ of structural Formula II; and $X^1$, $X^2$, $X^3$ and $X^4$ are independently selected from N or CH, provided that no more than one of $X^1$, $X^2$, $X^3$ and $X^4$ is N.

5. The compound of claim 4 wherein R$^3$ is C$_1$-C$_6$ alkyl and R$^4$ is C$_1$-C$_6$ alkyl.

6. The compound of claim 5 wherein R$^3$ and R$^4$ are methyl.

7. The compound of claim 2 wherein

is a selected from the group consisting of

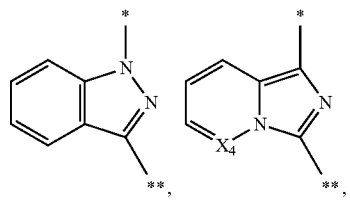

-continued $X^4$ is selected from the group consisting of CH and N;

$R^a$ is independently selected at each occurrence from the group consisting of —H and —C$_1$-C$_6$ alkyl;

$R^1$ is independently selected at each occurrence from the group consisting of —H, halo and —C$_1$-C$_6$ alkyl, said alkyl optionally being substituted with one to three substituents selected from halo, —C$_1$-C$_6$ alkyl, and —CF$_3$;

$R^2$ is selected from the group consisting of —C$_1$-C$_6$ alkyl, —(CR$^a{}_2$)$_r$CF$_3$, —(CR$^a{}_2$)$_r$—C$_{3-10}$cycloalkyl, and —(CR$^a{}_2$)$_r$aryl, said alkyl, cycloalkyl and aryl being optionally substituted with one to three substituents selected from halo, —C$_1$-C$_6$ alkyl and —CF$_3$;

R is independently selected from —H, —C$_1$-C$_6$ alkyl and aryl;

R$^3$ and R$^4$ are each C$_1$-C$_6$ alkyl;

m is 0, 1, 2 or 3; and r is 0, 1, 2, or 3.

8. A compound selected from the group consisting of:

| Example | IUPAC NAME |
|---|---|
| 1 | 4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one |
| 2 | 4-amino-5,5-dimethyl-2-[3-(3,3,3-trifluoropropyl)-1H-indazol-1-yl]-5,7-dihydro-6H-pyrrolo[2,3-d]pyrimidin-6-one |
| 3 | 4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one |
| 4 | 4-amino-5,5-dimethyl-2-[3-(2,3,6-trifluorobenzyl)-1H-indazol-1-yl]-5,7-dihydro-6H-pyrrolo[2,3-d]pyrimidin-6-one |
| 5 | 4-amino-2-(5-fluoro-3-hexyl-1H-indazol-1-yl)-5,5-dimethyl-5,7-dihydro-6H-pyrrolo[2,3-d]pyrimidin-6-one |
| 6 | 4-amino-2-[5-bromo-3-(2,3,6-trifluorobenzyl)-1H-indazol-1-yl]-5,5-dimethyl-5,7-dihydro-6H-pyrrolo[2,3-d]pyrimidin-6-one |
| 7 | 4-amino-5,5-dimethyl-2-[5-pyridin-4-yl-3-(2,3,6-trifluorobenzyl)-1H-indazol-1-yl]-5,7-dihydro-6H-pyrrolo[2,3-d]pyrimidin-6-one |
| 8 | 4-amino-5,5-dimethyl-2-[3-(4,4,4-trifluorobutyl)-1H-thieno[3,4-c]pyrazol-1-yl]-5,7-dihydro-6H-pyrrolo[2,3-d]pyrimidin-6-one |
| 9 | 4-amino-5,5-dimethyl-2-[3-(2,3,6-trifluorobenzyl)-1H-thieno[3,4-c]pyrazol-1-yl]-5,7-dihydro-6H-pyrrolo[2,3-d]pyrimidin-6-one |
| 10 | 4-amino-5,5-dimethyl-2-[3-(2,3,6-trifluorobenzyl)-4,6-dihydro-1H-thieno[3,4-c]pyrazol-1-yl]-5,7-dihydro-6H-pyrrolo[2,3-d]pyrimidin-6-one |
| 11 | 4-amino-2-[3-(2-cyclopentylethyl)-1H-indazol-1-yl]-5,5-dimethyl-5,7-dihydro-6H-pyrrolo[2,3-d]pyrimidin-6-one |
| 12 | 4-amino-2-[3-(2-fluorobenzyl)-1H-indazol-1-yl]-5,5-dimethyl-5,7-dihydro-6H-pyrrolo[2,3-d]pyrimidin-6-one |
| 13 | 4-amino-2-[5-chloro-3-(2-fluorobenzyl)-1H-indazol-1-yl]-5,5-dimethyl-5,7-dihydro-6H-pyrrolo[2,3-d]pyrimidin-6-one |
| 14 | 4-amino-2-[5-fluoro-3-(2-fluorobenzyl)-1H-indazol-1-yl]-5,5-dimethyl-5,7-dihydro-6H-pyrrolo[2,3-d]pyrimidin-6-one |
| 15 | 4-amino-2-[5-chloro-3-(2,3-difluorobenzyl)-1H-indazol-1-yl]-5,5-dimethyl-5,7-dihydro-6H-pyrrolo[2,3-d]pyrimidin-6-one |

-continued

| Example | IUPAC NAME |
|---|---|
| 16 | 4-amino-2-[3-(2,3-difluorobenzyl)-5-fluoro-1H-indazol-1-yl]-5,5-dimethyl-5,7-dihydro-6H-pyrrolo[2,3-d]pyrimidin-6-one |
| 17 | 4-amino-2-[3-(2,3-difluorobenzyl)-1H-indazol-1-yl]-5,5-dimethyl-5,7-dihydro-6H-pyrrolo[2,3-d]pyrimidin-6-one |
| 18 | 4-amino-2-[3-(2-fluorobenzyl)-5-phenyl-1H-indazol-1-yl]-5,5-dimethyl-5,7-dihydro-6H-pyrrolo[2,3-d]pyrimidin-6-one |
| 19 | 4-amino-2-[5-fluoro-3-(2,3,6-trifluorobenzyl)-1H-indazol-1-yl]-5,5-dimethyl-5,7-dihydro-6H-pyrrolo[2,3-d]pyrimidin-6-one |
| 20 | 4-amino-5,5-dimethyl-2-[5-pyridin-3-yl-3-(2,3,6-trifluorobenzyl)-1H-indazol-1-yl]-5,7-dihydro-6H-pyrrolo[2,3-d]pyrimidin-6-one |
| 21 | 4-amino-5,5-dimethyl-2-[5-(1-methyl-1H-pyrazol-4-yl)-3-(2,3,6-trifluorobenzyl)-1H-indazol-1-yl]-5,7-dihydro-6H-pyrrolo[2,3-d]pyrimidin-6-one |
| 22 | 4-amino-2-[5-(3,5-dimethyl-1H-pyrazol-4-yl)-3(2,3,6-trifluorobenzyl)-1H-indazol-1-yl]-5,5-dimethyl-5,7-dihydro-6H-pyrrolo[2,3-d]pyrimidin-6-one |
| 23 | 4-amino-2-[5-(3-furyl)-3-(2,3,6-trifluorobenzyl)-1H-indazol-1-yl]-5,5-dimethyl-5,7-dihydro-6H-pyrrolo[2,3-d]pyrimidin-6-one |
| 24 | 4-amino-5,5-dimethyl-2-[5-(4-methyl-3-thienyl)-3-(2,3,6-trifluorobenzyl)-1H-indazol-yl]-5,7-dihydro-6H-pyrrolo[2,3-d]pyrimidin-6-one |
| 25 | 4-amino-2-[5-cyclopropyl-3-(2,3,6-trifluorobenzyl)-1H-indazol-1-yl]-5,5-dimethyl-5,7-dihydro-6H-pyrrolo[2,3-d]pyrimidin-6-one |
| 26 | 4-amino-5,5-dimethyl-2-[5-pyridin-4-yl-3-(2,3,6-trifluorobenzyl)-1H-indazol-1-yl] -5,7-dihydro-6H-pyrrolo[2,3-d]pyrimidin-6-one |
| 27 | 4-amino-5,5-dimethyl-2-[5-phenyl-3-(2,3,6-trifluorobenzyl)-1H-indazol-1-yl]-5,7-dihydro-6H-pyrrolo[2,3-d]pyrimidin-6-one |
| 28 | 4-amino-2-[5-chloro-3-(pyrimidin-5-ylmethyl)-1H-indazol-1-yl]-5,5-dimethyl-5,7-dihydro-6H-pyrrolo[2,3-d]pyrimidin-6-one |
| 29 | 4-amino-5,5-dimethyl-2-[5-(3-thienyl)-3-(2,3,6-trifluorobenzyl)-1H-indazol-1-yl]-5,7-dihydro-6H-pyrrolo[2,3-d]pyrimidin-6-one |
| 30 | 4-amino-2-[5-(5-fluoropyridin-3-yl)-3-(2,3,6-trifluorobenzyl)-1H-indazol-1-yl]-5,5-dimethyl-5,7-dihydro-6H-pyrrolo[2,3-d]pyrimidin-6-one |
| 31 | 4-amino-2-[5-(6-fluoropyridin-3-yl)-3-(2,3,6-trifluorobenzyl)-1H-indazol-1-yl]-5,5-dimethyl-5,7-dihydro-6H-pyrrolo[2,3-d]pyrimidin-6-one |
| 32 | 4-amino-5,5-dimethyl-2-{3-(2,3,6-trifluorobenzyl)-5-[5-(trifluoromethyl)pyridin-3-yl]-1H-indazol-1-yl}-5,7-dihydro-6H-pyrrolo[2,3-d]pyrimidin-6-one |
| 33 | 4-amino-2-[3-(6-bromo-2,3-difluorobenzyl)-5-chloro-1H-indazol-1-yl]-5,5-dimethyl-5,7-dihydro-6H-pyrrolo[2,3-d]pyrimidin-6-one |
| 34 | 4-amino-2-[3-(2-cyclopentylethyl)-1H-indazol-1-yl]-5,5-dimethyl-5,7-dihydro-6H-pyrrolo[2,3-d]pyrimidin-6-one |
| 35 | 4-amino-2-(5-fluoro-3-pentyl-1H-indazol-1-yl)-5,5-dimethyl-5,7-dihydro-6H-pyrrolo[2,3-d]pyrimidin-6-one |
| 36 | 4-amino-2-[5-fluoro-3-(3,3,3-trifluoropropyl)-1H-indazol-1-yl]-5,5-dimethyl-5,7-dihydro-6H-pyrrolo[2,3-d]pyrimidin-6-one |
| 37 | 4-amino-2-[3-(2-cyclopentylethyl)-5-fluoro-1H-indazol-1-yl]-5,5-dimethyl-5,7-dihydro-6H-pyrrolo[2,3-d]pyrimidin-6-one |
| 38 | 4-amino-2-[3-(2-cyclopentylethyl)-5-fluoro-1H-indazol-1-yl]-5,5-dimethyl-5,7-dihydro-6H-pyrrolo[2,3-d]pyrimidin-6-one |
| 39 | 4-amino-2-[5-fluoro-3-(4,4,4-trifluorobutyl)-1H-indazol-1-yl]-5,5-dimethyl-5,7-dihydro-6H-pyrrolo[2,3-d]pyrimidin-6-one |
| 40 | 4-amino-2-(5-chloro-3-pentyl-1H-indazol-1-yl)-5,5-dimethyl-5,7-dihydro-6H-pyrrolo[2,3-d]pyrimidin-6-one |
| 41 | 4-amino-2-(3-butyl-5-chloro-1H-indazol-1-yl)-5,5-dimethyl-5,7-dihydro-6H-pyrrolo[2,3-d]pyrimidin-6-one |
| 42 | 4-amino-2-[5-chloro-3-(4,4,4-trifluorobutyl)-1H-indazol-1-yl]-5,5-dimethyl-5,7-dihydro-6H-pyrrolo[2,3-d]pyrimidin-6-one |
| 43 | 4-amino-2-(5-chloro-3-pent-4-en-1-yl-1H-indazol-1-yl)-5,5-dimethyl-5,7-dihydro-6H-pyrrolo[2,3-d]pyrimidin-6-one |
| 44 | 4-amino-2-(3-but-3-en-1-yl-5-chloro-1H-indazol-1-yl)-5,5-dimethyl-5,7-dihydro-6H-pyrrolo[2,3-d]pyrimidin-6-one |
| 45 | 4-amino-2-(5-chloro-3-propyl-1H-indazol-1-yl)-5,5-dimethyl-5,7-dihydro-6H-pyrrolo[2,3-d]pyrimidin-6-one |
| 46 | ethyl 3-[1-(4-amino-5,5-dimethyl-6-oxo-6,7-dihydro-5H-pyrrolo[2,3-d]pyrimidin-2-yl)-5-chloro-1H-indazol-3-yl]propanoate |
| 47 | 4-amino-2-[5-chloro-3-(3,3-dimethylbutyl)-1H-indazol-1-yl]-5,5-dimethyl-5,7-dihydro-6H-pyrrolo[2,3-d]pyrimidin-6-one |
| 48 | 4-amino-2-[3-(2,3-difluorobenzyl)-1H-thieno[3,4-c]pyrazol-1-yl]-5,5-dimethyl-5,7-dihydro-6H-pyrrolo[2,3-d]pyrimidin-6-one |
| 49 | 4-amino-2-[6-chloro-3-(2,3-difluorobenzyl)-1H-thieno[3,4-c]pyrazol-1-yl]-5,5-dimethyl-5,7-dihydro-6H-pyrrolo[2,3-d]pyrimidin-6-one |
| 50 | 4-amino-2-[5-chloro-3-(2,3-difluorobenzyl)-1H-thieno[2,3-c]pyrazol-1-yl]-5,5-dimethyl-5,7-dihydro-6H-pyrrolo[2,3-d]pyrimidin-6-one |
| 51 | 4-amino-2-[3-(2,3-difluorobenzyl)-1H-thieno[3,2-c]pyrazol-1-yl]-5,5-dimethyl-5,7-dihydro-6H-pyrrolo[2,3-d]pyrimidin-6-one |
| 52 | 4-amino-2-[5-chloro-3-(2,3,6-trifluorobenzyl)-1H-thieno[2,3-c]pyrazol-1-yl]-5,5-dimethyl-5,7-dihydro-6H-pyrrolo[2,3-d]pyrimidin-6-one |
| 53 | 4-amino-5,5-dimethyl-2-[3-(2,3,6-trifluorobenzyl)-1H-thieno[3,2-c]pyrazol-1-yl]-5,7-dihydro-6H-pyrrolo[2,3-d]pyrimidin-6-one |
| 54 | 4-amino-5,5-dimethyl-2-[5-methyl-3-(2,3,6-trifluorobenzyl)pyrazolo[4,3-c]pyrazol-1(5H)-yl]-5,7-dihydro-6H-pyrrolo[2,3-d]pyrimidin-6-one |

| Example | IUPAC NAME |
|---|---|
| 55 | 4-amino-5,5-dimethyl-2-[3-(2,3,6-trifluorobenzyl)-1H-thieno[2,3-c]pyrazol-1-yl]-5,7-dihydro-6H-pyrrolo[2,3-d]pyrimidin-6-one |
| 56 | 4-amino-5,5-dimethyl-2-[6-methyl-3-(2,3,6-trifluorobenzyl)pyrazolo[3,4-c]pyrazol-1(6H)-yl]-5,7-dihydro-6H-pyrrolo[2,3-d]pyrimidin-6-one |
| 57 | 4-amino-5,5-dimethyl-2-[3-(2,3,6-trifluorobenzyl)-1H-pyrazolo[4,3-c]pyridin-1-yl]-5,7-dihydro-6H-pyrrolo[2,3-d]pyrimidin-6-one |
| 58 | 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one |
| 59 | 4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 60 | 4-amino-2-[6-fluoro-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 61 | 4-amino-5,5-dimethyl-2-[5-(2,3,6-trifluorobenzyl)imidazo[5,1-b][1,3]thiazol-7-yl]-5,7-dihydro-6H-pyrrolo[2,3-d]pyrimidin-6-one |
| 62 | 4-amino-5,5-dimethyl-2-[1-(2,3,6-trifluorobenzyl)imidazo[1,5-a]pyridin-3-yl]-5,7-dihydro-6H-pyrrolo[2,3-d]pyrimidin-6-one |
| 63 | 4-amino-2-[3-(2,3-difluorobenzyl)imidazo[1,5-a]pyridin-1-yl]-5,5-dimethyl-5,7-dihydro-6H-pyrrolo[2,3-d]pyrimidin-6-one |
| 64 | 4-amino-2-[7-(2,3-difluorobenzyl)imidazo[1,5-b]pyridazin-5-yl]-5,5-dimethyl-5,7-dihydro-6H-pyrrolo[2,3-d]pyrimidin-6-one |
| 65 | 4-amino-2-[3-(2,3-difluorobenzyl)-6-fluoroimidazo[1,5-a]pyridin-1-yl]-5,5-dimethyl-5,7-dihydro-6H-pyrrolo[2,3-d]pyrimidin-6-one |
| 66 | 4-amino-2-[7-(2-fluorobenzyl)imidazo[1,5-b]pyridazin-5-yl]-5,5-dimethyl-5,7-dihydro-6H-pyrrolo[2,3-d]pyrimidin-6-one |
| 67 | 4-amino-2-[3-(2-fluorobenzyl)imidazo[1,5-a]pyridin-1-yl]-5,5-dimethyl-5,7-dihydro-6H-pyrrolo[2,3-d]pyrimidin-6-one |
| 68 | 4-amino-2-[6-fluoro-3-(2-fluorobenzyl)imidazo[1,5-a]pyridin-1-yl]-5,5-dimethyl-5,7-dihydro-6H-pyrrolo[2,3-d]pyrimidin-6-one |
| 69 | 4-amino-2-[6-chloro-3-(2-fluorobenzyl)imidazo[1,5-a]pyridin-1-yl]-5,5-dimethyl-5,7-dihydro-6H-pyrrolo[2,3-d]pyrimidin-6-one |
| 70 | 4-amino-2-[7-(2,3-difluorobenzyl)-2-methylimidazo[1,5-b]pyridazin-5-yl]-5,5-dimethyl-5,7-dihydro-6H-pyrrolo[2,3-d]pyrimidin-6-one |
| 71 | 4-amino-2-[6-chloro-3-(2,3-difluorobenzyl)imidazo[1,5-a]pyridin-1-yl]-5,5-dimethyl-5,7-dihydro-6H-pyrrolo[2,3-d]pyrimidin-6-one |
| 72 | 4-amino-2-(3-benzylimidazo[1,5-a]pyridin-1-yl)-5,5-dimethyl-5,7-dihydro-6H-pyrrolo[2,3-d]pyrimidin-6-one |
| 73 | 4-amino-5,5-dimethyl-2-[3-(2,3,6-trifluorobenzyl)imidazo[1,5-a]pyridin-1-yl]-5,7-dihydro-6H-pyrrolo[2,3-d]pyrimidin-6-one |
| 74 | 4-amino-5,5-dimethyl-2[6-phenyl-3-(2,3,6-trifluorobenzyl)imidazo[1,5-a]pyridin-1-yl]-5,7-dihydro-6H-pyrrolo[2,3-d]pyrimidin-6-one |
| 75 | 4-amino-2-[6-(2-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 76 | 4-amino-2-[6-(3-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 77 | 4-amino-2-[6-(4-fluorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 78 | 4-amino-2-[6-(3-chlorophenyl)-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 79 | 4-amino-5,5-dimethyl-2-[6-(3-thienyl)-3-(2,3,6-trifluorobenzyl)imidazo[1,5-a]pyridin-1-yl]-5,7-dihydro-6H-pyrrolo[2,3-d]pyrimidin-6-one |
| 80 | 4-amino-2-[6-cyclopropyl-3-(2,3,6-trifluorobenzyl)imidazo[1,5-a]pyridin-1-yl]-5,5-dimethyl-5,7-dihydro-6H-pyrrolo[2,3-d]pyrimidin-6-one |
| 81 | 4-amino-5,5-dimethyl-2-[7-(3,3,3-trifluoropropyl)imidazo[1,5-b]pyridazin-5-yl]-5,7-dihydro-6H-pyrrolo[2,3-d]pyrimidin-6-one |
| 82 | 4-amino-5,5-dimethyl-2-[3-(2,4,6-trifluorobenzyl)imidazo[1,5-a]pyridin-1-yl]-5,7-dihydro-6H-pyrrolo[2,3-d]pyrimidin-6-one |
| 83 | 4-amino-2-[3-(2-chloro-6-fluoro-3-methylbenzyl)imidazo[1,5-a]pyridin-1-yl]-5,5-dimethyl-5,7-dihydro-6H-pyrrolo[2,3-d]pyrimidin-6-one |
| 84 | 4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one |
| 85 | 4-amino-5,5-dimethyl-2-[7-(4,4,4-trifluorobutyl)imidazo[1,5-b]pyridazin-5-yl]-5,7-dihydro-6H-pyrrolo[2,3-d]pyrimidin-6-one |
| 86 | 4-amino-5,5-dimethyl-2-[3-(4,4,4-trifluorobutyl)imidazo[1,5-a]pyridin-1-yl]-5,7-dihydro-6H-pyrrolo[2,3-d]pyrimidin-6-one |
| 87 | 4-amino-5,5-dimethyl-2-{3-[2-(2-thienyl)ethyl]imidazo[1,5-a]pyridin-1-yl}-5,7-dihydro-6H-pyrrolo[2,3-d]pyrimidin-6-one |
| 88 | 4-amino-2-[3-(2-cyclopropylethyl)imidazo[1,5-a]pyridin-1-yl]-5,5-dimethyl-5,7-dihydro-6H-pyrrolo[2,3-d]pyrimidin-6-one |
| 89 | 4-amino-5,5-dimethyl-2-(3-pentylimidazo[1,5-a]pyridin-1-yl)-5,7-dihydro-6H-pyrrolo[2,3-d]pyrimidin-6-one |
| 90 | 4-amino-5,5-dimethyl-2-(7-pentylimidazo[1,5-b]pyridazin-5-yl)-5,7-dihydro-6H-pyrrolo[2,3-d]pyrimidin-6-one |
| 91 | 4-amino-5,5-dimethyl-2-[3-(3-methylbutyl)imidazo[1,5-a]pyridin-1-yl]-5,7-dihydro-6H-pyrrolo[2,3-d]pyrimidin-6-one |
| 92 | 4-amino-5,5-dimethyl-2-[3-methyl-5-(2,3,6-trifluorobenzyl)imidazo[5,1-b][1,3]thiazol-7-yl]-5,7-dihydro-6H-pyrrolo[2,3-d]pyrimidin-6-one |
| 93 | 4-amino-5,5-dimethyl-2-[2-methyl-5-(2,3,6-trifluorobenzyl)imidazo[5,1-b][1,3]thiazol-7-yl]-5,7-dihydro-6H-pyrrolo[2,3-d]pyrimidin-6-one |

-continued

| Example | IUPAC NAME |
|---|---|
| 94 | 4-amino-2-[5-(2-fluorobenzyl)imidazo[5,1-b][1,3]thiazol-7-yl]-5,5-dimethyl-5,7-dihydro-6H-pyrrolo[2,3-d]pyrimidin-6-one |
| 95 | 4-amino-5,5-dimethyl-2-[1-(3,3,3-trifluoropropyl)-1H-indazol-3-yl]-5,7-dihydro-6H-pyrrolo[2,3-d]pyrimidin-6-one |
| 96 | 4-amino-2-[5-chloro-3-(2,3,6-trifluorobenzyl)-1H-indazol-1-yl]-5,5-dimethyl-5,8-dihydropyrido[2,3-d]pyrimidin-7(6H)-one |
| 97 | 4-amino-5,5-dimethyl-2-[3-(2,3,6-trifluorobenzyl)-1H-indazol-1-yl]-5,8-dihydropyrido[2,3-d]pyrimidin-7(6H)-one |
| 98 | 4-amino-5,5-dimethyl-2-[3-(2,3,6-trifluorobenzyl)-1H-thieno[3,4-c]pyrazol-1-yl]-5,8-dihydropyrido[2,3-d]pyrimidin-7(6H)-one |
| 99 | 4-amino-5,5-dimethyl-2-[3-(2,3,6-trifluorobenzyl)-4,6-dihydro-1H-thieno[3,4-c]pyrazol-1-yl]-5,8-dihydropyrido[2,3-d]pyrimidin-7(6H)-one |
| 100 | 4-amino-2-[5-chloro-3-(3,3,3-trifluoropropyl)-1H-indazol-1-yl]-5-ethyl-5-methyl-5,7-dihydro-6H-pyrrolo[2,3-d]pyrimidin-6-one |
| 101 | 4-amino-2-[5-chloro-3-(3,3,3-trifluoropropyl)-1H-indazol-1-yl]-5-methyl-5-propyl-5,7-dihydro-6H-pyrrolo[2,3-d]pyrimidin-6-one |
| 102 | 4-amino-2-[5-chloro-3-(3,3-dimethylbutyl)-1H-indazol-1-yl]-5-ethyl-5-methyl-5,7-dihydro-6H-pyrrolo[2,3-d]pyrimidin-6-one |
| 103 | 4-amino-5-ethyl-2-[3-(2-fluorobenzyl)imidazo[1,5-a]pyridin-1-yl]-5-methyl-5,7-dihydro-6H-pyrrolo[2,3-d]pyrimidin-6-one |
| 104 | 4-amino-5,5-dimethyl-2-[3-(3,3,4,4,4-pentafluorobutyl)-1H-indazol-1-yl]-5,7-dihydro-6H-pyrrolo[2,3-d]pyrimidin-6-one |
| 105 | 4-amino-2-[5-fluoro-3-(3,3,4,4,4-pentafluorobutyl)-1H-indazol-1-yl]-5,5-dimethyl-5,7-dihydro-6H-pyrrolo[2,3-d]pyrimidin-6-one |
| 106 | 4-amino-2-[5-chloro-3-(3,3,4,4,4-pentafluorobutyl)-1H-indazol-1-yl]-5,5-dimethyl-5,7-dihydro-6H-pyrrolo[2,3-d]pyrimidin-6-one |
| 107 | 4-amino-5,5-dimethyl-2-[3-(3,3,4,4,4-pentafluorobutyl)-1H-pyrazolo[4,3-b]pyridin-1-yl]-5,7-dihydro-6H-pyrrolo[2,3-d]pyrimidin-6-one |
| 108 | 4-amino-5,5-dimethyl-2-[3-(3,3,4,4,4-pentafluorobutyl)imidazo[1,5-a]pyridin-1-yl]-5,7-dihydro-6H-pyrrolo[2,3-d]pyrimidin-6-one |
| 109 | 4-amino-2-[6-fluoro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one |
| 110 | 4-amino-2-[6-chloro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one |
| 111 | 4-amino-2-[6-chloro-1-(3,3,4,4,4-pentafluorobutyl)-1H-indazol-3-yl]-5,5-dimethyl-5,7-dihydro-6H-pyrrolo[2,3-d]pyrimidin-6-one | and the pharmaceutically acceptable salts thereof.

9. The compound of claim 8 selected from the group consisting of:
4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one;
4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one;
4-amino-5,5-dimethyl-2-[3-(2,3,6-trifluorobenzyl)-1H-thieno[3,4-c]pyrazol-1-yl]-5,7-dihydro-6H-pyrrolo[2,3-d]pyrimidin-6-one;
4-amino-2-[5-chloro-3-(2,3,6-trifluorobenzyl)-1H-thieno[2,3-c]pyrazol-1-yl]-5,5-dimethyl-5,7-dihydro-6H-pyrrolo[2,3-d]pyrimidin-6-one
4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one;
4-amino-2-[6-chloro-3-(2,3,6-trifluorobenzyl)imidazo[1,5-a]pyridin-1-yl]-5,5-dimethyl-5,7-dihydro-6H-pyrrolo[2,3-d]pyrimidin-6-one;
4-amino-2-[6-fluoro-3-(2,3,6-trifluorobenzyl)imidazo[1,5-a]pyridin-1-yl]-5,5-dimethyl-5,7-dihydro-6H-pyrrolo[2,3-d]pyrimidin-6-one;
4-amino-2-[3-(2,3-difluorobenzyl)-6-fluoroimidazo[1,5-a]pyridin-1-yl]-5,5-dimethyl-5,7-dihydro-6H-pyrrolo[2,3-d]pyrimidin-6-one;
4-amino-5,5-dimethyl-2-[3-(2,3,6-trifluorobenzyl)imidazo[1,5-a]pyridin-1-yl]-5,7-dihydro-6H-pyrrolo[2,3-d]pyrimidin-6-one;
4-amino-2-[3-(2-cyclopentylethyl)imidazo[1,5-a]pyridin-1-yl]-5,5-dimethyl-5,7-dihydro-6H-pyrrolo[2,3-c]pyrimidin-6-one;
4-amino-5,5-dimethyl-2-[3-(3,3,4,4,4-pentafluorobutyl)-1H-indazol-1-yl]-5,7-dihydro-6H-pyrrolo[2,3-c]pyrimidin-6-one;
4-amino-2-[5-fluoro-3-(3,3,4,4,4-pentafluorobutyl)-1H-indazol-1-yl]-5,5-dimethyl-5,7-dihydro-6H-pyrrolo[2,3-d]pyrimidin-6-one;
4-amino-2-[5-chloro-3-(3,3,4,4,4-pentafluorobutyl)-1H-indazol-1-yl]-5,5-dimethyl-5,7-dihydro-6H-pyrrolo[2,3-d]pyrimidin-6-one;
4-amino-5,5-dimethyl-2-[3-(3,3,4,4,4-pentafluorobutyl)imidazo[1,5-a]pyridin-1-yl]-5,7-dihydro-6H-pyrrolo[2,3-d]pyrimidin-6-one;
4-amino-2-[6-fluoro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one;
4-amino-2-[6-chloro-3-(3,3,4,4,4-pentafluorobutyl)imidazo[1,5-a]pyridin-1-yl]-5,5-dimethyl-5,7-dihydro-6H-pyrrolo[2,3-d]pyrimidin-6-one;
4-amino-2-[6-chloro-1-(3,3,4,4,4-pentafluorobutyl)-1H-indazol-3-yl]-5,5-dimethyl-5,7-dihydro-6H-pyrrolo[2,3-d]pyrimidin-6-one;
and the pharmaceutically acceptable salts thereof.

10. A method for activating soluble guanylate cyclase comprising the step of administering an amount efficacious of the compound of claim 1 or a pharmaceutically acceptable salt thereof.

11. A method for the treatment of pulmonary hypertension, comprising administering a therapeutically effective amount of the compound of claim 1 or a pharmaceutically acceptable salt thereof to a patient in need thereof.

12. A method for the treatment of hypertension comprising administering a therapeutically effective amount of the compound of claim 1 or a pharmaceutically acceptable salt thereof to a patient in need thereof.

13. A method for the treatment of heart failure comprising administering a therapeutically effective amount of the compound of claim 1 or a pharmaceutically acceptable salt thereof to a patient in need thereof.

14. A pharmaceutical composition comprised of the compound of claim 1 or a pharmaceutically acceptable salt thereof and a pharmaceutically acceptable carrier.

15. The pharmaceutical composition of claim 14 comprising one or more pharmaceutically active agents in addition to the compound of claim 1 or a pharmaceutically acceptable salt thereof.

16. The pharmaceutical composition of claim 15 wherein the one or more additional active agents is selected from the group consisting of an angiotensin converting enzyme inhibitor, an angiotensin II receptor antagonist, a neutral endopeptidase inhibitor, an aldosterone antagonist, a renin inhibitor, an endothelin receptors antagonist, a vasodilator, a calcium channel blocker, a potassium channel activator, a diuretic, a sympatholytic, a beta-adrenergic blocking drug, an alpha adrenergic blocking drug, a central alpha adrenergic agonist, a peripheral vasodilator, a lipid lowering agent and a metabolic altering agent.

17. The compound of claim 1 that is 4-amino-2-[5-chloro-3-(3,3,3-trifluoropropyl)-1H-indazol-1-yl]-5,5-dimethyl-5,7-dihydro-6H-pyrrolo[2,3-d]pyrimidin-6-one

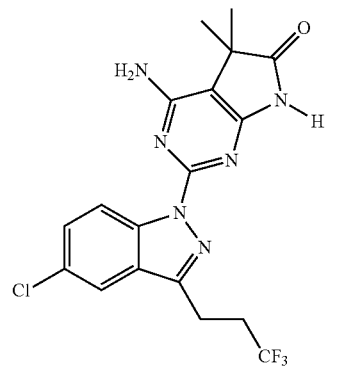 [SMILES: CC1(C)C(=O)Nc2nc(-n3nc(CCC(F)(F)F)c4cc(Cl)ccc43)nc(N)c21]

or a pharmaceutically acceptable salt thereof.

18. The compound of claim 1 that is 4-amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one

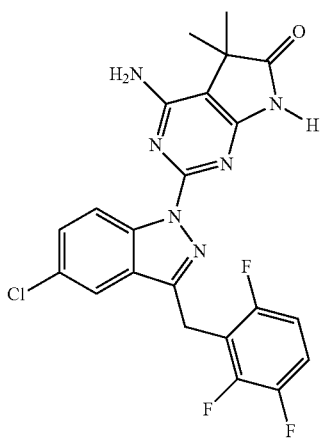 [SMILES: CC1(C)C(=O)Nc2nc(-n3nc(Cc4c(F)ccc(F)c4F)c4cc(Cl)ccc43)nc(N)c21]

or a pharmaceutically acceptable salt thereof.

19. The compound of claim 1 that is 4-amino-2-[6-chloro-3-(2,3,6-trifluorobenzyl)imidazo[1,5-c]pyridin-1-yl]-5,5-dimethyl-5,7-dihydro-6H-pyrrolo[2,3-d]pyrimidin-6-one

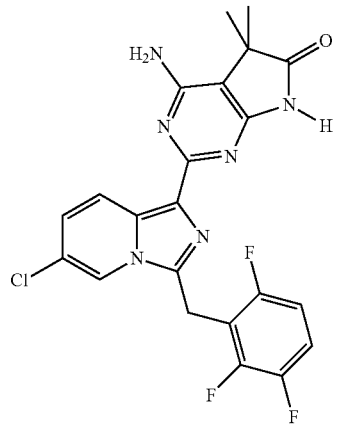 [SMILES: CC1(C)C(=O)Nc2nc(-c3nc(Cc4c(F)ccc(F)c4F)n4cc(Cl)ccc34)nc(N)c21]

or a pharmaceutically acceptable salt thereof.

20. The compound of claim 1 that is 4-amino-2-[6-fluoro-3-(2,3,6-trifluorobenzyl)imidazo[1,5-c]pyridin-1-yl]-5,5-dimethyl-5,7-dihydro-6H-pyrrolo[2,3-d]pyrimidin-6-one

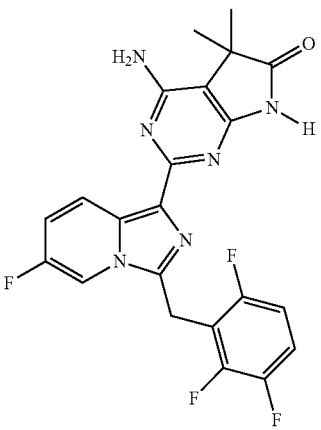 [SMILES: CC1(C)C(=O)Nc2nc(-c3nc(Cc4c(F)ccc(F)c4F)n4cc(F)ccc34)nc(N)c21]

or a pharmaceutically acceptable salt thereof.

* * * * *